(12) United States Patent
Su et al.

(10) Patent No.: US 8,706,232 B2
(45) Date of Patent: Apr. 22, 2014

(54) BILATERAL ELECTRICAL STIMULATION THERAPY FOR BLADDER DYSFUNCTION

(75) Inventors: Xin Su, Shoreview, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 50 days.

(21) Appl. No.: 13/358,100

(22) Filed: Jan. 25, 2012

(65) Prior Publication Data
US 2012/0197337 A1    Aug. 2, 2012

Related U.S. Application Data

(60) Provisional application No. 61/437,081, filed on Jan. 28, 2011.

(51) Int. Cl.
*A61N 1/36* (2006.01)

(52) U.S. Cl.
USPC ............................................. 607/40; 607/41

(58) Field of Classification Search
USPC ...................... 607/1–3, 39–41, 46, 48, 55–58
See application file for complete search history.

(56) References Cited

U.S. PATENT DOCUMENTS

| 7,369,894 | B2 | 5/2008 | Gerber | |
|---|---|---|---|---|
| 2004/0193228 | A1 | 9/2004 | Gerber | |
| 2005/0033372 | A1 | 2/2005 | Gerber | |
| 2006/0190046 | A9 | 8/2006 | Gerber | |
| 2007/0255333 | A1* | 11/2007 | Giftakis et al. | 607/39 |
| 2011/0118805 | A1* | 5/2011 | Wei et al. | 607/41 |
| 2012/0197338 | A1 | 8/2012 | Su et al. | |

* cited by examiner

*Primary Examiner* — Brian T Gedeon
(74) *Attorney, Agent, or Firm* — Shumaker & Sieffert, PA

(57) ABSTRACT

A medical device is configured to deliver a first stimulation therapy to a patient, and, upon detecting a trigger event, deliver a second stimulation therapy to the patient. In some examples, the first stimulation therapy includes bilateral stimulation in which stimulation is delivered at different times to two lateral sides of the patient and the second stimulation therapy includes substantially simultaneous bilateral stimulation therapy to two lateral sides of the patient. In some examples, the second stimulation therapy may elicit a stronger inhibitory physiological response related to incontinence (e.g., inhibition of bladder contractions) than the first stimulation therapy. The trigger event may include, for example, any one or more of detection of a physiological condition indicative of an increased possibility of an involuntary voiding event or an imminent involuntary voiding event, input from the patient, a predetermined time of day, or expiration of a timer.

42 Claims, 15 Drawing Sheets

BILATERAL ELECTRICAL STIMULATION THERAPY FOR BLADDER DYSFUNCTION

This application claims the benefit of U.S. Provisional Application Ser. No. 61/437,081 by Su et al., which was filed on Jan. 28, 2011, and is entitled "BILATERAL ELECTRICAL STIMULATION THERAPY FOR BLADDER DYSFUNCTION." U.S. Provisional Application Ser. No. 61/437,081 by Su et al. is incorporated herein by reference in its entirety

TECHNICAL FIELD

The disclosure relates to electrical stimulation therapy, and, more particularly, stimulation therapy for the management of bladder dysfunction.

BACKGROUND

Bladder dysfunction, such as an overactive bladder, urgency, or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, or urinary incontinence. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence.

In some cases, urinary incontinence can be attributed to improper sphincter function, either in the internal urinary sphincter or external urinary sphincter. Nerves running though the pelvic floor stimulate contractility in the sphincter. An improper communication between the nervous system and the urethra or urinary sphincter can result in a bladder dysfunction, such as overactive bladder, urgency, urge incontinence, urine retention disorder, or another type of urinary incontinence.

SUMMARY

In general, the disclosure is directed to managing a bladder dysfunction by delivering a first stimulation therapy to a patient, and, upon detecting a trigger event, delivering a second stimulation therapy to the patient. The first stimulation therapy includes bilateral stimulation in which stimulation is delivered at different times to two lateral sides of the patient. For example, a stimulation period during which stimulation is delivered to a first lateral side of the patient may not overlap with a stimulation period during which stimulation is delivered to a second lateral side of the patient. In some examples, the electrical stimulation signal trains (e.g., pulse trains) that elicit a therapeutic effect from the patient may be delivered to one lateral side of the patient at a time, such that the signal trains do not overlap during the first stimulation therapy. The second stimulation therapy includes substantially simultaneous bilateral stimulation therapy to the two lateral sides of the patient. For example, the electrical stimulation signal trains may be delivered to both lateral sides of the patient at the same time, such that the stimulation trains overlap. The second stimulation therapy may be selected to elicit a stronger inhibitory physiological response related to incontinence (e.g., inhibition of bladder contractions) than the first stimulation therapy.

In one aspect, the disclosure is directed to a method that comprises, with a processor, controlling a stimulation generator to deliver a first electrical stimulation therapy to a patient, wherein the first electrical stimulation therapy comprises delivery of electrical stimulation to a first lateral side of the patient and a second lateral side of the patient at different times, after initiating delivery of the first electrical stimulation therapy, detecting a trigger event, and, in response to detecting the trigger event, with the processor, controlling the stimulation generator to deliver a second electrical stimulation therapy to the patient, wherein the second electrical stimulation therapy comprises delivery of electrical stimulation substantially simultaneously to the first and second lateral sides of the patient.

In another aspect, the disclosure is directed to a system comprising a stimulation generator configured to generate and deliver electrical stimulation to a patient, and a processor configured to control the stimulation generator to deliver a first electrical stimulation therapy to the patient, detect a trigger event after initiating delivery of the first electrical stimulation therapy and, in response to detecting the trigger event, control the stimulation generator to deliver a second electrical stimulation therapy to the patient. The first electrical stimulation therapy comprises delivery of electrical stimulation to a first lateral side of the patient and a second lateral side of the patient at different times. The second electrical stimulation therapy comprises delivery of electrical stimulation substantially simultaneously to the first and second lateral sides of the patient.

In a further aspect, the disclosure is directed to a system that comprises means for delivering electrical stimulation therapy to a patient, means for detecting a trigger event after initiating delivery of the first electrical stimulation therapy, and means for controlling the means for delivering electrical stimulation therapy. The means for controlling is configured to control the means for delivering electrical stimulation therapy to deliver a first electrical stimulation therapy to a patient, where the first electrical stimulation therapy comprises delivery of electrical stimulation to a first lateral side of the patient and a second lateral side of the patient at different times. The means for controlling is further configured to, in response to detection of the trigger event, control the means for delivering electrical stimulation therapy to deliver a second electrical stimulation therapy to the patient, wherein the second electrical stimulation therapy comprises delivery of electrical stimulation substantially simultaneously to the first and second lateral sides of the patient.

In an additional aspect, the disclosure is directed to a computer-readable storage medium comprising instructions that, when executed by a processor, cause the processor to control a stimulation generator to deliver a first electrical stimulation therapy to a patient, wherein the first electrical stimulation therapy comprises delivery of electrical stimulation to a first lateral side of the patient and a second lateral side of the patient at different times, detect a trigger event after the first stimulation therapy is initiated, and control the stimulation generator to deliver a second electrical stimulation therapy to the patient in response to detecting the trigger event. The second electrical stimulation therapy comprises delivery of electrical stimulation substantially simultaneously to the first and second lateral sides of the patient.

In another aspect, the disclosure is directed to a computer-readable storage medium, which may be an article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable storage medium may be non-transitory.

The details of one or more example are set forth in the accompanying drawings and the description below. Other features, objects, and advantages will be apparent from the description and drawings, and from the claims.

DETAILED DESCRIPTION

Bladder dysfunction refers to a condition of improper functioning of the bladder or urinary tract, and may include, for example, an overactive bladder, urgency, urine retention disorder, or urinary incontinence. Urgency is a sudden, compelling urge to urinate, and may often, though not always, be associated with urinary incontinence. Urinary incontinence refers to a condition of involuntary voiding events (i.e., involuntary loss of urine in the case of urinary incontinence), and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence.

One type of therapy that has been proposed for managing bladder dysfunction (e.g., minimizing bladder contractions and/or the number of involuntary voiding events) includes delivery of electrical stimulation to a target tissue site within a patient. For example, delivery of electrical stimulation from an implantable medical device to a target tissue site proximate any one or more of a spinal nerve, a sacral nerve, a pudendal nerve, dorsal genital nerve, a tibial nerve, an inferior rectal nerve, a perineal nerve, or branches of any of the aforementioned nerves to modulate the nerve activities may provide an effective therapy for managing bladder dysfunction. As an example, electrical stimulation to modulate the activity of the sacral and/or pudendal nerve (or branches thereof) may help reduce bladder contraction frequency, which can mitigate urgency.

Figure 1:
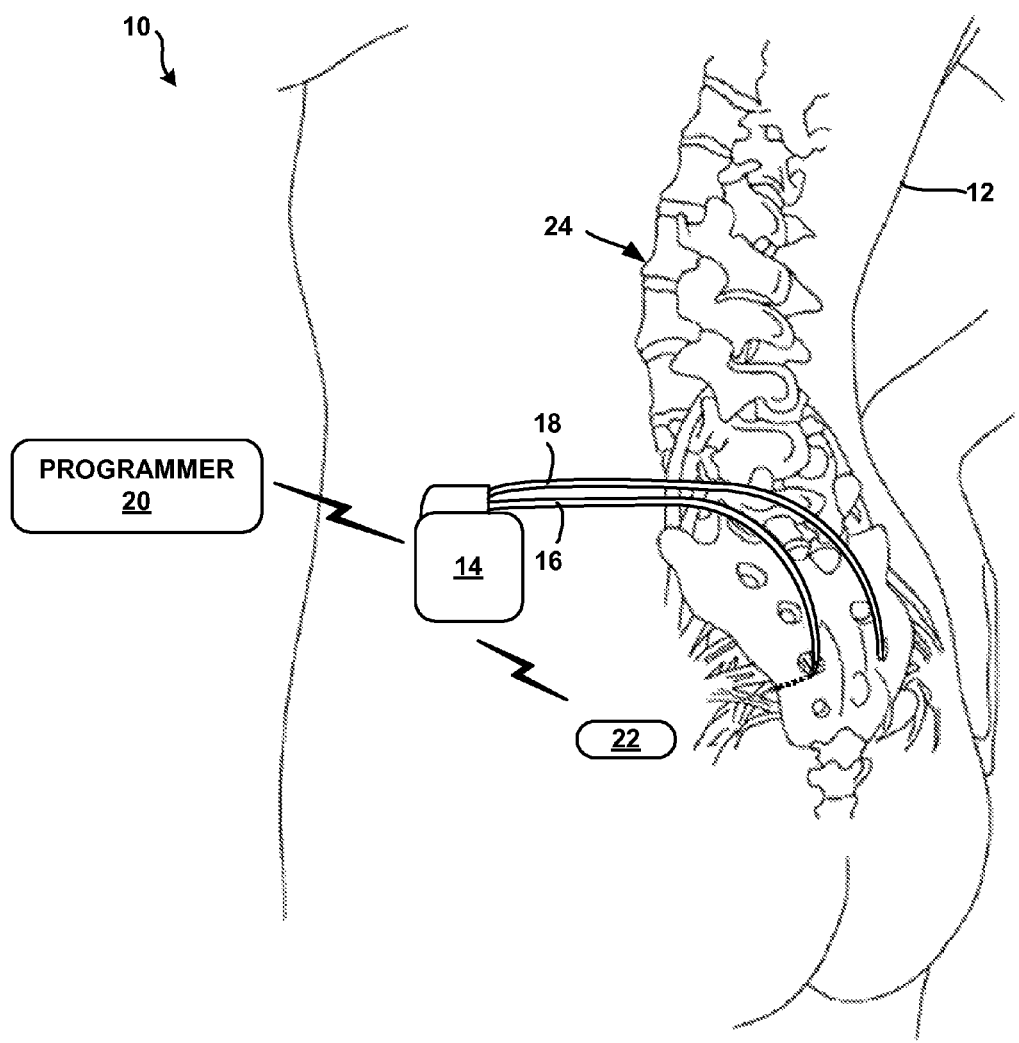
FIG. 1 is a conceptual diagram of an example therapy system that delivers a first stimulation therapy to a patient and, when triggered, a second stimulation therapy that includes substantially simultaneous bilateral stimulation.

FIG. 1 is a conceptual diagram that illustrates an example of a therapy system 10 that delivers electrical stimulation therapy to patient 12 to manage a bladder dysfunction of patient 12. As described in further detail below, in some examples, therapy system 10 delivers a first electrical stimulation therapy, and, when triggered, a second electrical stimulation therapy to manage a bladder dysfunction of patient 12. Therapy system 10 includes an implantable medical device (IMD) 14, which is coupled to leads 16, 18. System 10 also includes an external programmer 20, which communicates with IMD 14 via a wireless communication protocol, and sensor 22, which generates a signal indicative of a physiological parameter of patient 12. The physiological parameter is indicative of a condition of patient 12 related to bladder dysfunction, e.g., relating to a bladder fill level, bladder contraction or a posture or activity level of patient 12.

IMD 14 generally operates as a therapy device that delivers electrical stimulation therapy to patient 12 by generating and delivering a programmable electrical stimulation signal (e.g., in the form of electrical pulses or a continuous waveform) to target therapy sites proximate electrodes of leads 16, 18. In the example shown in FIG. 1, the electrodes of each lead 16, 18 are disposed proximate to a distal end of the respective lead 16, 18. The target tissue sites can be, for example, proximate a spinal nerve, a sacral nerve, a pudendal nerve, dorsal genital nerve, a tibial nerve, an inferior rectal nerve, a perineal nerve, or branches of any of the aforementioned nerves. The target tissue sites are selected based on the type of bladder dysfunction (or other patient condition) for which therapy system 10 is implemented to treat.

In some examples, the target tissue sites can be identified prior to implantation of leads 16, 18. For example, a device, such as an introducer or needle, can be introduced into patient 12 and a test electrical signal can be delivered to tissue of patient 12 via the device. The device may be moved within patient 12 until a desirable physiological response is elicited by the test electrical signal, which can indicate that the device (e.g., the one or more electrodes used to deliver the test stimulation) is positioned at a tissue site that captures a target nerve. In some examples, the physiological response may be detected through a motor response that may be visually detected, a sensory response as reported by the patient, or through an electrical response e.g., sensed nerve signals). Electrodes of leads 16, 18 can subsequently be positioned at the tissue site at which the test electrical signal elicited the desirable physiological response. In other examples, the test stimulation may be delivered via leads 16, 18.

IMD 14 may be surgically implanted in patient 12 at any suitable location within patient 12, such as in the side of the lower abdomen or the side of the lower back or upper buttocks, IMD 14 can include a biocompatible outer housing, which may be formed from titanium, stainless steel, a liquid crystal polymer, or the like. One or more medical leads, e.g., leads 16, 18, may be connected to IMD 14 and surgically or percutaneously tunneled to place one or more electrodes of the respective lead at a target tissue site proximate to a desired nerve or muscle, e.g., one of the previously listed target therapy sites, such as a tissue site proximate a spinal, sacral or pudendal nerve. The proximal ends of leads 16, 18 are both electrically and mechanically coupled to IMD 14 either directly or indirectly, e.g., via respective lead extensions.

Electrical conductors disposed within the lead bodies of leads 16, 18 electrically connect electrodes of the respective lead to a therapy delivery module (e.g., a stimulation generator) of IMD 14. In addition, in some examples, the electrical conductors of leads 16, 18 electrically connect the electrodes of the respective lead to a sensing module of IMD 14, which enables IMD 14 to sense a physiological parameter of patient 12 via the electrodes.

A midline of patient 12 divides a body of patient 12 into two lateral sides, which can be referred to as a left side and a right side. Spinal cord 24 of patient 12 is approximately positioned at the midline of patient 12, such that one lateral side of patient 12 may be considered to be on one side of spinal cord 24 and the other lateral side of patient 12 may be considered to be on other side of spinal cord 24. At least some of the nerves innervating the pelvic floor of patient 12, as well as other nerves of patient 12, comprise left and right branches (or portions) on respective lateral sides of patient 12. In the example shown in FIG. 1, leads 16, 18 are positioned to deliver stimulation to target tissue sites on respective lateral sides of patient 12, such that therapy system 10 is configured to deliver bilateral stimulation to patient 12 via electrodes of leads 16, 18. In this way, IMD 14 may deliver bilateral stimulation to patient 12 by delivering stimulation to target tissue sites on opposite sides of the midline of patient 12 via electrodes positioned on respective lateral sides of patient 12. For example, IMD 14 may deliver stimulation to a first lateral side of patient 12 via a first set of electrodes positioned on the first lateral side of patient (e.g., proximate a nerve or nerve branch on the first lateral side) and deliver stimulation to a second lateral side of patient 12 via a second set of electrodes (different than the first set) positioned on the second lateral side of patient (e.g., proximate a nerve or nerve branch on the second lateral side). In some examples, the target tissue sites are selected such that delivery of stimulation to the target tissue sites either at different times or substantially simultaneously provides an inhibitory physiological response related to voiding of patient 12, such as a reduction in a frequency of bladder contractions.

In some examples, when IMD 14 delivers bilateral stimulation to patient 12, IMD 14 delivers electrical stimulation to both lateral sides of patient 12 to achieve a desired therapeutic effect, such as a reduction in bladder contraction frequency. The stimulation delivered to both lateral sides of the patient works together (e.g., in a synergistic fashion) to provide a common therapeutic effect. Thus, regardless of whether IMD 14 delivers bilateral stimulation by delivering electrical stimulation to the two lateral sides of patient 12 at different times (e.g., non-overlapping pulse trains, stimulation periods, "on cycles" or any combination thereof) or at substantially simultaneously (e.g., at least partially overlapping pulse trains, stimulation periods, "on cycles" or any combination thereof), the desired therapeutic effect may be elicited by the stimulation to both lateral sides of the patient. In some cases, the desired therapeutic effect may not be elicited without the electrical stimulation delivery to both lateral sides of patient 12. In contrast to bilateral stimulation, when IMD 14 delivers unilateral stimulation, IMD 14 delivers electrical stimulation to only one lateral side of patient 14 to achieve a desired therapeutic effect. With unilateral stimulation, the therapeutic effect is elicited by the stimulation delivered to only one lateral side of the patient 12, and stimulation need not be delivered to both lateral sides of patient 12 to achieve the desired therapeutic effect.

Leads 16, 18 can be positioned to deliver stimulation to target tissue sites proximate branches of the same nerve or branches of different nerves. For example, IMD 14 can deliver bilateral stimulation to patient 12 by delivering stimulation to both the left and right nerve branches (or portions) of the same nerve and/or by delivering stimulation to a left branch of a first nerve and a right branch of a second nerve that is different than the first nerve. As an example, leads 16, 18 can be positioned to deliver electrical stimulation to tissue sites on both lateral sides of patient 12 to modulate activity of both a left and a right sacral nerve or nerve portion, both a left and a right pudendal nerve or nerve portion, and/or both a sacral nerve or nerve portion and a pudendal nerve or nerve portion on different lateral sides of patient 12. The target tissue sites on the two lateral sides of patient 12 can be target tissue sites proximate to branches of the same nerve or branches of different nerves. In addition, IMD 14 can deliver bilateral stimulation to patient 12 via a subset of electrodes of both leads 16, 18, e.g., electrodes of each lead 16, 18 can be positioned on a different lateral side of patient 12 or one or both of the leads 16, 18 can be positioned such that electrodes of the respective lead are located on both lateral sides of patient 12.

It is believed that electrical stimulation of bilateral spinal nerves may produce a stronger inhibition of bladder contractions than unilateral nerve stimulation alone. Techniques for controlling delivery of bilateral stimulation to patient 12 to manage bladder dysfunction are described herein. In some examples, IMD 14 delivers a first stimulation therapy to patient 12, and, upon detecting a trigger event, delivers a second stimulation therapy to patient 12. Thus, the second stimulation therapy is delivered to patient 12 in a closed loop or a pseudo-closed loop manner in these examples because the initiation of the delivery of the second stimulation therapy is dependent upon detection of a trigger event. As discussed in further detail below, the trigger event that triggers the delivery of the second stimulation therapy can include, for example, detection of a physiological condition indicative of an increased possibility of an involuntary voiding event (e.g., relative to a baseline or another previously determined condition) or an imminent involuntary voiding event, input from the patient (or a patient caretaker) that indicates that additional therapy to help prevent the occurrence of an involuntary voiding event is desirable, a time of day, and/or expiration of a timer. The duration of the timer can be, for example, based on a bladder fill cycle of the patient, which is discussed in further detail below. In some examples, the timer is started at a beginning of the patient's bladder fill cycle, such as immediately after patient 12 voids.

The first and second stimulation therapies both include bilateral stimulation to patient 12, but the coordination of stimulation to the lateral sides of patient 12 differs between the first and second stimulation therapies. The coordination may include, for example, the extent to which a stimulation period for electrical stimulation delivered to a first lateral side of the patient overlaps with a stimulation period for electrical stimulation delivered to a second lateral side of the patient. The stimulation period may be, for example, the period of time during which IMD 14 is actively delivering stimulation to patient 12, such as in the form of an electrical stimulation train (e.g., a waveform or pulse train). The stimulation signals during the stimulation period may not be continuous (e.g., may be delivered in bursts of continuous time signals or pulses, or in a plurality of pulses separated in time). However, the stimulation period represents the period of time during which IMD 14 is actively generating and delivering stimulation to a particular lateral side of patient 12.

In some cases, the coordination includes, for example, the extent to which electrical stimulation trains delivered to each lateral side of patient 12 overlap. In some examples, an electrical stimulation train is defined by the electrical stimulation signals delivered to patient 12 (e.g., to one lateral side of patient 12) to elicit a desired therapeutic effect. In the case of electrical stimulation pulses, the electrical stimulation signal train may be referred to as a "pulse train" and may include, for example, a plurality of pulses (e.g., at least two pulses) separated in time. The period of time between the start of consecutive pulses in the pulse train may be referred to as a pulse period. In some examples, two or more pulse periods may be considered to be part of a common pulse train, as well as part of a common stimulation period. In the case of continuous time pulses, the electrical stimulation signal train may include a plurality of stimulation signal cycles (e.g., at least two cycles, such as at least two sine waves). In some examples, two or more stimulation signal cycles may be considered to be part of a common stimulation signal train, as well as part of a common stimulation period. In either the case of continuous time signals or pulses, the electrical stimulation signal train may have a specific duration, which may be equal to, for example, a stimulation period during which IMD 14 delivers electrical stimulation to the respective lateral side of patient 12.

It is believed that the manner in which the electrical stimulation is coordinated between the lateral sides of patient 12 may affect the efficacy of the stimulation therapy, e.g., because the timing of the stimulation delivery between the two lateral sides of patient 12 may affect the strength of the physiological response elicited by the bilateral stimulation or the timing with which the physiological response is observed. This may be at least partially attributable to the spatial summation of the physiological effects of the electrical stimulation therapy. As discussed in further detail below, the second stimulation therapy may elicit a greater physiological response related to bladder dysfunction and/or a more immediate physiological response from patient 12.

The first stimulation therapy includes the delivery of bilateral stimulation to target tissue sites on both lateral sides of patient 12, where the stimulation is delivered to the lateral sides at different times (e.g., in a time interleaved manner). In the example shown in FIG. 1, the target tissue sites are selected to be a tissue site that helps manage the bladder dysfunction of patient 12. In some examples, the target tissue is proximate to at least one of a spinal nerve, a sacral nerve, a pudendal nerve, dorsal genital nerve, a tibial nerve, an inferior rectal nerve, a perineal nerve, or a branch thereof. In some examples of the first stimulation therapy, IMD 14 does not actively deliver stimulation signals to the first and second lateral sides of patient 12 at the same time. While post-stimulation effects generated by delivery of stimulation to tissue sites on the first and second lateral sides of patient 12 may be observed at substantially the same time in response to the first stimulation therapy, the stimulation trains delivered to the first and second lateral sides do not overlap in time in these examples. In these examples, IMD 14 terminates delivery of stimulation signals to one lateral side before initiating delivery of stimulation signals to the other lateral side of patient 12.

In some examples, IMD 14 delivers the first stimulation therapy by alternating delivery of stimulation to a first target tissue site on a first lateral side of patient 12 and a second target tissue site on a second lateral side of patient 12, such that IMD 14 delivers pulse trains to respective lateral sides of patient 12 at different, non-overlapping times. As an example, IMD 14 may deliver a first pulse train to a first lateral side of patient 12 during a first stimulation period, and at the end of the first stimulation period, cease delivery of stimulation to the first lateral side and initiate delivery of a second pulse train to a second lateral side of patient 12 during a second stimulation period. During the second stimulation period, IMD 14 does not deliver stimulation to the first lateral side of the patient, and during the first stimulation period, IMD 14 does not deliver stimulation to the second lateral side of the patient. Delivery of stimulation signal trains to the lateral sides of patient 12 in this non-overlapping manner may repeat for as long of a stimulation period as desired. Alternating delivery of stimulation to the lateral sides of patient 12 may help reduce the amount of stimulation delivered to a single tissue site of patient 12, which may extend the total duration of therapeutic benefit to patient 12 provided by therapy system 10, e.g., by reducing patent adaptation.

Reducing the amount of stimulation delivered to a single tissue site in patient may help reduce neuron habituation or other forms of patient adaptation to the stimulation therapy and extend an effective lifetime of the stimulation therapy (e.g., the time for which the stimulation therapy is efficacious in reducing bladder contraction frequency). It has been found that patient 12 may adapt to stimulation delivered by IMD 14 over time, such that a certain level of electrical stimulation provided to a tissue site in patient 12 may be less effective over time. This phenomenon may be referred to as "adaptation." As a result, any beneficial effects to patient 12 from the electrical stimulation may decrease over time. While the electrical stimulation levels (e.g., amplitude of the electrical stimulation signal) may be increased to overcome such adaptation, the increase in stimulation levels may consume more power, and may eventually reach undesirable levels of stimulation. Delivery of bilateral stimulation to patient 12 in an alternating fashion may help reduce the adaptation The alternating stimulation delivered to the first and target tissue sites can be substantially balanced in some examples, e.g., IMD 14 delivers stimulation having substantially similar stimulation intensities to the two lateral sides of patient 12 and/or IMD 14 delivers stimulation to both lateral sides of patient 12 for substantially equal amounts of time. Substantial similarity in the intensity of stimulation may be indicated by, for example, substantially similar stimulation signals. Stimulation intensity may be affected by, for example, a current amplitude of the stimulation signal, a voltage amplitude of the stimulation signal, a frequency of the stimulation signal, a pulse rate of the stimulation signal, a pulse width of the stimulation signal, the shape of the stimulation signal, the duty cycle of the stimulation signal, or the combination of electrodes with which IMD 14 delivers the stimulation to patient 12.

As an example of the substantially balanced bilateral stimulation delivered to patient 12 in an alternating manner, IMD 14 can deliver a pulse train (or waveform) to the first target tissue site on a first lateral side of patient 12 for a duration of time followed by delivery of the same stimulation pulse train to the second target tissue site on a second lateral side of patient 12 for the duration of time, followed by delivery of the same stimulation pulse train to the first target tissue site for the duration of time, and so forth. Other techniques for delivering substantially balanced bilateral stimulation in an alternating manner are contemplated.

In other examples, the stimulation delivered to the first and target tissue sites for the first stimulation therapy is imbalanced, e.g., the intensity of stimulation delivered to the two lateral sides of patient 12 is different, the stimulation is delivered to each lateral side of patient 12 for different durations of time (i.e., the stimulation periods for the lateral sides are different), or both. As an example of the substantially imbalanced bilateral stimulation delivered to patient 12 in an alternating manner, IMD 14 can deliver a first stimulation pulse train to the first target tissue site for a first duration of time followed by delivery of a second pulse train to the second target tissue site for a second duration of time, and so forth. In order to achieve imbalanced bilateral stimulation, the stimulation pulses of the first and second pulse trains can be the same, and the first and second durations of time may be different. In other examples, in order to achieve imbalanced bilateral stimulation, the stimulation pulses of the first and second pulse trains may be different, and the first and second durations of time may be the same or different. Other techniques for delivering imbalanced bilateral stimulation in an alternating manner are contemplated.

The second stimulation therapy includes substantially simultaneous bilateral stimulation therapy, whereby IMD 14 delivers stimulation to both lateral sides of patient 12 at substantially the same time. During substantially simultaneous bilateral stimulation therapy, the pulse trains delivered by IMD 14 to respective lateral sides of patient 12 at least partially overlap. As an example, IMD 14 may deliver a first pulse train to a first lateral side of patient 12, and, at the same time, deliver a second pulse train to a second lateral side of patient 12. IMD 14 may deliver the first and second pulse trains such that they completely overlap (e.g., start and stop at the same time, such that the stimulation periods are the same) or partially overlap (e.g., the first pulse train may be delivered for a period of time prior to delivering the second pulse train, such that the stimulation periods partially overlap). The intensity levels of the stimulation delivered to the two sides of patient are substantially equal in some examples, and are different in other examples. IMD 14 delivers stimulation to a first lateral side of patient 12 during a first stimulation period and delivers stimulation to a second lateral side of patient 12 during a second stimulation period. During the second stimulation therapy delivered by IMD 14, the first and second stimulation periods at least partially overlap, such that stimulation is delivered to the first and second lateral sides of patient 12 substantially simultaneously.

The second stimulation therapy may not consist substantially entirely of substantially simultaneous bilateral stimulation therapy. For example, IMD 14 may initiate delivery of stimulation to at least one of the first lateral side or second lateral side of patient 12 prior to initiating delivery of stimulation to the other one of the first lateral side or second lateral side of patient 12. As another example, the stimulation delivered to the first and second stimulation periods may periodically, but not entirely, overlap during the delivery of the second stimulation period. In other examples, during the second stimulation therapy delivered by IMD 14, the first and second stimulation periods substantially completely overlap, such that the second stimulation therapy consists substantially entirely of substantially simultaneous bilateral stimulation therapy. The first and second stimulation periods may be substantially the same in some examples, and may be different in other examples.

In examples in which the stimulation delivered to the lateral sides of patient 12 at substantially the same time have substantially similar intensities and are delivered for substantially similar durations of time (i.e., have substantially similar stimulation periods), the substantially simultaneous bilateral stimulation may be considered balanced. Likewise, in examples in which the stimulation delivered to the lateral sides of patient 12 at substantially the same time have at least one of different similar intensities and or different stimulation periods, the substantially simultaneous bilateral stimulation may be considered imbalanced.

In the first and second stimulation therapies, the intensity of stimulation that is delivered to patient 12 can be lower than, substantially equal to, or greater than a threshold stimulation intensity level (also referred to herein as a "threshold intensity" or "threshold intensity level") for patient 12. The threshold stimulation intensity level may be the stimulation intensity level at which an acute, physiologically significant response (also referred to herein as a threshold physiological response) of patient 12 is first observed when increasing the stimulation intensity from a low intensity to a higher intensity. Stated another way, the threshold stimulation intensity level may be defined as approximately the lowest stimulation intensity level that elicits an acute, physiologically significant response of patient 12. The acute, physiologically significant response may or may not be perceived by patient 12. In some examples, an acute response may be defined as a physiological response that occurs within about 30 seconds (e.g., about 10 seconds) of patient 12 receiving the stimulation.

The sufficiency of the stimulation in producing an acute physiological response and/or desired therapeutic effect may be a function of stimulation intensity and time for which stimulation is delivered. Stimulation intensity may be, in turn, a function of one or more parameters. In the case of stimulation pulses, stimulation intensity may be a function of current of voltage pulse amplitude, pulse rate, and pulse width. The desired therapeutic effect is different from the acute physiological response. As one illustration, the desired therapeutic effect may be a reduction in the frequency of bladder contractions in the patient, whereas the acute physiological response may be a motor function caused by the stimulation.

The physiologically significant response used to determine the threshold intensity level can be any suitable physiological response, which may be selected by, e.g., patient 12 or a clinician. The physiological response of interest may be, for example, a patient perception (e.g., the threshold intensity level may be a patient perception threshold), a motor response (e.g., the threshold intensity level may be a motor threshold), a response indicative of capture of a nerve (e.g., the threshold intensity level may be a nerve capture threshold). The nerve capture can be detected using any suitable technique, such as, e.g., sensing afferent or efferent nerve signals via electrodes implanted in patient 12 or external to patient 12 when the stimulation is delivered to patient 12. Other types of physiological responses may be detected and may be unrelated to the type of therapy for which therapy system 10 delivers therapy in some examples. For example, a toe twitch may be considered to be a physiological response that is indicative of a stimulation threshold intensity, but the toe twitch may be a response that does not provide efficacious therapy to patient 12.

In other examples, the physiological response may be related to the type of therapy for which therapy system 10 delivers therapy. For example, the physiological response may be an acute reduction in bladder contraction frequency or intensity. The threshold intensity level, however, may not be the same as a therapy threshold, e.g., a stimulation intensity at which IMD 14 provides efficacious therapy to patient 12 to manage the patient condition (e.g., to reduce bladder contraction frequency).

Whether or not a physiological response is considered to be physiologically significant can be determined by patient 12, a clinician, or another suitable person or device. As an example, the stimulation may elicit movement of a toe of patient 12, and patient 12 may define the movement of the toe as physiologically significant when the movement of the toe is perceptible or when the movement of the toe is above some arbitrary amount defined by patient 12 or the clinician.

In some examples, the first and second stimulation therapies are configured to elicit similar inhibitory physiological responses (e.g., a reduction in bladder contraction frequency) from patient 12 related to voiding, e.g., to reduce a bladder contraction frequency. However, the relative strength of the inhibitory physiological response elicited by the first and second stimulation therapies may differ. In some examples, the second stimulation therapy elicits a more immediate inhibitory physiological response compared to the first stimulation therapy, and, in some cases, a stronger inhibitory physiological response than the first stimulation therapy. Otherwise stated, the second stimulation therapy may elicit a more acute physiological response from patient 12 that helps minimize the likelihood of an occurrence of an involuntary voiding event, where the acute response may be observed in a shorter amount of time compared to the physiological response elicited from the delivery of the first stimulation therapy. In this way, the second stimulation therapy may provide more efficacious therapy than the first stimulation therapy in some situations, such as when a patient condition indicative of an increased possibility of an involuntary voiding event or an imminent involuntary voiding event is detected.

In examples in which the inhibitory physiological response includes a reduction in bladder contraction frequency, the reduction in bladder contraction frequency resulting from the delivery of the second stimulation therapy may be greater that the reduction in bladder contraction frequency resulting from delivery of the first stimulation therapy. In this way, a second inhibitory physiological response elicited by the delivery of the second stimulation therapy may be greater (or stronger) than a first inhibitory physiological response elicited by the delivery of the first stimulation therapy.

In some examples, the first stimulation therapy produces a relatively moderate inhibitory physiological response compared to the second stimulation therapy. In some examples, the inhibitory physiological response elicited by the first stimulation therapy is observed during the stimulation period (also referred to herein as a first time period) in which IMD 14 delivers the first stimulation therapy to patient 12. This physiological response may also be observed during a post-stimulation period (also referred to herein as a second time period) in some examples. IMD 14 does not deliver the first stimulation therapy to patient 12 during the post-stimulation period, and, in some examples, does not deliver any therapy to patient 12 during the post-stimulation period.

In some examples, the physiological response to stimulation may be more pronounced during the post-stimulation period that immediately follows the stimulation period. For example, the delivery of the first stimulation therapy by IMD 14 may elicit an inhibitory physiological response related to a voiding event during a stimulation period and a post-stimulation period, and the inhibitory physiological response during the post-stimulation period may be greater than the inhibitory physiological response during the stimulation period. When the inhibitory physiological response includes a reduction in bladder contraction frequency, for example, the delivery of the first stimulation therapy can reduce the bladder contraction frequency during the stimulation period and the post-stimulation period, where the reduction in bladder contraction frequency is greater during the post-stimulation period.

In other examples, the inhibitory physiological response evoked by the first stimulation therapy may not be observed immediately upon the delivery of the first stimulation therapy, but, rather, may be observed during the post-stimulation period. Thus, the first stimulation therapy may elicit an inhibitory physiological response related to voiding during a post-stimulation period, and may not elicit an inhibitory physiological response related to voiding while IMD 14 during a stimulation period.

IMD 14 may deliver the first stimulation therapy in an open loop manner in some examples, in which IMD 14 delivers the first stimulation therapy without intervention from a user or a sensor. For example, if the first stimulation therapy elicits a delayed physiological response that is observed during a second time period that immediately follows a first time period during which stimulation is delivered to patient 12, IMD 14 can deliver the first stimulation therapy to patient 12 as a periodic repetition of the first time period and second time period. In other examples, IMD 14 may deliver the first stimulation therapy in a closed loop manner. For example, IMD 14 deliver the first stimulation therapy for the first time period, and cease delivery of the first stimulation therapy until a certain bladder contraction frequency is detected. An example of closed-loop delivery of the first stimulation therapy is described below with respect to FIG. 8.

In accordance with some examples of the disclosure, IMD 14 delivers the first stimulation therapy to patient 12 over an extended period of time, e.g., chronic stimulation, and delivers the second stimulation therapy to patient 12 when a stronger therapy is needed or desirable. Thus, in some cases, the second stimulation therapy may be referred to as an acute therapy or a temporary therapy because the second stimulation therapy is delivered for only periodically relative to the first stimulation therapy, e.g., as needed, rather than on a regular basis. By limiting the delivery of substantially simultaneous bilateral stimulation therapy, the amount of therapy delivered to patient 12 is limited compared to examples in which the substantially simultaneous bilateral stimulation is delivered to patient continuously and not based on a detected trigger event. Reducing the overall amount of stimulation delivered to patient 12 may help reduce neuron habituation or other forms of patient adaptation to the stimulation therapy and extend an effective lifetime of the stimulation therapy (e.g., the time for which the stimulation therapy is efficacious in reducing bladder contraction frequency).

In some examples, IMD 14 delivers the first and second stimulation therapies in different time slots, i.e., on a time-interleaved basis, such that IMD 14 only delivers one type of stimulation therapy at a time. In these examples, IMD 14 may deliver the first stimulation therapy, and, when triggered, deactivate delivery of the first stimulation therapy and activate delivery of the second stimulation therapy. IMD 14 may deliver the second stimulation therapy for a predetermined duration of time, referred to herein as a therapy period, for a duration of time controlled by patient 12, or until a specific patient event is detected (e.g., voluntary voiding). In these examples, after delivering the second stimulation therapy, IMD 14 may revert back to delivering the first stimulation therapy until another trigger event for activating the delivery of the second stimulation therapy is detected.

As discussed above, a trigger event can include, for example, detection of a physiological condition indicative of an increased possibility of an involuntary voiding event or an imminent involuntary voiding event, input from the patient (or a patient caretaker) that indicates that additional therapy to help prevent the occurrence of involuntary voiding event is desirable, or expiration of a timer comprising a predetermined duration of time. Any one or more of the trigger events may be implemented by IMD 14 to control the timing of the second stimulation therapy. The trigger event is different from the thresholds or other parameters used to control closed loop delivery of the first stimulation therapy.

In examples in which the trigger event comprises a physiological condition of patient 12, IMD 14 may detect the physiological condition based on a physiological parameter of patient 12 sensed by, e.g., via sensor 22 or a sensing module of IMD 14. An example of a trigger event comprising a physiological condition is a bladder volume (e.g., as indicated by an impedance of the bladder of patient 12, pressure sensed at a bladder wall, the output of a strain gauge on the bladder wall, and the like) that is indicative of an increased possibility of an involuntary voiding event. Another example of a trigger event comprising a physiological condition is a bladder contraction intensity or bladder contraction frequency at or above a trigger event threshold. The trigger event threshold is selected to be a level that is indicative of an increased possibility of an involuntary voiding event, e.g., relative to a patient condition for which the first stimulation therapy is appropriate.

IMD 14 may detect contractions of bladder based on any suitable physiological parameter such as, but not limited to, bladder impedance, bladder pressure, pudendal or sacral afferent nerve signals, an electromyogram (EMG) of a relevant muscle (e.g., a urinary sphincter muscle, bladder wall or detrusor muscle), or any combination thereof. Thus, sensor 22 may include, for example, a pressure sensor positioned in patient 12 to detect changes in bladder pressure, electrodes for sensing pudendal or sacral afferent nerve signals, electrodes for sensing urinary sphincter EMG signals (or anal sphincter EMG signals in examples in which therapy system 10 provides therapy to manage fecal urgency or fecal incontinence), or any combination thereof. In examples in which IMD 14 detects bladder contractions or a bladder volume (also referred to herein as a fill level) based on an impedance through the bladder of patient 12, which varies as a function of the contraction of the bladder, IMD 14 can determine the impedance through the bladder using the sensing configuration shown and described below with respect to FIG. 16.

As shown in FIG. 1, in some examples, sensor 22 can be physically separate from IMD 14 and can wirelessly transmit signals to IMD 14. Alternatively sensor 22 may be carried on one of leads 16, 18 or an additional lead coupled to IMD 14. In some examples, sensor 22 may include one or more electrodes for sensing afferent nerve signals or one or more sense electrodes for generating an EMG of a relevant muscle.

One type of bladder contraction detection algorithm indicates an occurrence of a bladder contraction when a signal generated by sensor 22 (or a sensing module of IMD 14 or another sensing module) exhibits a certain characteristic, which may be a time domain characteristic (e.g., a mean, median, peak or lowest signal amplitude within a particular time period) or a frequency domain characteristic (e.g., an energy level in one or more frequency bands or a ratio of energy levels in different frequency bands). Another bladder contraction detection algorithm indicates the occurrence of a bladder contraction if a sensed signal substantially correlates to a signal template, e.g., in terms of frequency, amplitude and/or spectral energy characteristics. IMD 14 may use known techniques to correlate a sensed signal with a template in order to detect the bladder contraction or detect the bladder contraction based on the frequency domain characteristics of a sensed signal. Other bladder contraction techniques may be used.

In addition to or instead of the previously discussed physiological conditions, the trigger event can be a patient activity level (e.g., an indication of the level of motion or movement of one or more of the patient's limbs or trunk) or patient posture state that is indicative of an increased probability of an occurrence of an involuntary voiding event. Sensor 22 may comprise, for example, a patient motion sensor, such as a two-axis accelerometer, three-axis accelerometer, one or more gyroscopes, pressure transducers, piezoelectric crystals, or other sensor that generates a signal that changes as patient activity level or posture state changes. In some examples, IMD 14 controls the delivery of the second stimulation therapy to patient 12 upon detecting a patient activity level exceeding a particular threshold based on the signal from the motion sensor. The patient activity level that is greater than or equal to a threshold (which may be stored in a memory of IMD 14, programmer 20 or another device) may indicate that patient 12 is engaging in an activity that may increase the possibility of an occurrence of an involuntary voiding event, and, therefore, the greater inhibition of bladder contraction frequency provided by the second stimulation therapy may be desirable while patient 12 is engaging in the activity. In this way, the second stimulation therapy provided by IMD 14 may be useful for providing responsive stimulation therapy that adapts the intensity of stimulation to the circumstances that may affect patient incontinence and provide an additional layer of therapy to help prevent the occurrence of an involuntary voiding event.

Instead of or in addition to the activity level of patient 12, IMD 14 can control the delivery of the second stimulation therapy to patient 12 upon detecting a posture state associated with a relatively high probability of an occurrence of an involuntary voiding event (compared to other posture states) based on the signal from sensor 22. For example, patient 12 may be more prone to an involuntary voiding event when patient 12 is in an upright posture state compared to a lying down posture state. IMD 14 may, for example, store a plurality of motion sensor signals and associate the signals with particular patient posture states using any suitable technique. IMD 14 may flag some of the posture states as being posture states for which additional therapy (e.g., delivery of the second stimulation therapy) to help prevent the occurrence of an incontinence event is desirable.

In some examples, the delivery of the second stimulation therapy is initiated based on a time of day, which can be predetermined and stored by IMD 14. The time of day at which IMD 14 initiates the delivery of the second stimulation therapy can be, for example, associated with a time of day at which patient 12 is more active, such that the additional layer of therapy to help prevent in involuntary voiding event may be desirable. As an example, IMD 14 may deliver the first stimulation therapy while patient 12 is sleeping (the sleep times can be associated with predetermined times of day in some examples or the sleep can be detected based on one or more patient parameters), and then initiate the delivery of the second stimulation therapy when patient 12 is awake. In other examples, the times of day at which IMD 14 initiates the delivery of the second stimulation therapy may be selected to be at regular or irregular time intervals. In addition, in other examples, the times of day at which IMD 14 initiates the delivery of the second stimulation therapy can be selected to be a time at which the patient's pelvic floor muscles may be more tired, which may increase the possibility of in an occurrence of an involuntary voiding event, such that the additional bladder dysfunction therapy may be desirable.

Another trigger event for initiating the delivery of the second stimulation therapy can be the expiration of a timer. The tinier used to trigger the second stimulation therapy can be based on, for example, the bladder fill cycle of patient 12. In these examples, IMD 14 can restart the tinier upon receiving an indication that the bladder fill cycle of patient 12 has been restarted, e.g. restarted by occurrence of a voiding event, which can be voluntary, hut, in some cases, involuntary. At the beginning of a bladder fill cycle, the bladder of patient 12 is substantially empty or low, and fills throughout the cycle. The bladder fill cycle restarts upon emptying of the bladder. The duration of the tinier may be selected such that IMD 14 delivers the second stimulation therapy when the bladder fill level of patient 12 is approximated to be at a level in which additional therapy delivery may be desirable to help reduce the possibility of the occurrence of an involuntary voiding event. For example, the duration of the timer may be about 50% to about 75% of the way through the bladder fill cycle for patient 12, although other durations can be used and can depend upon the severity of the patient's bladder dysfunction.

The bladder fill cycle that is used to select the timer duration can be specific to patient 12 or based on a plurality of patients, e.g., with similar bladder dysfunction disorders. In some examples, the duration of the tinier is selected based on the mean, median, or shortest bladder fill cycle duration of patient 12 during a certain period of time (e.g., on the order of hours, days, or weeks), which can be prior to any delivery of stimulation to patient 12, or a time period immediately preceding the time at which the timer duration is selected.

In some examples, instead of or in addition to a trigger event detected based on input from sensor 22 or expiration of a tinier, the trigger event can include patient input. Thus, IMD 14 may deliver the second stimulation therapy in response to receiving patient input. For example, patient 12 can interact with programmer 20 to provide input that causes IMD 14 to deliver the second stimulation therapy. In this way, patient 12 may control delivery of the second stimulation therapy. Patient 12 may initiate the delivery of the second stimulation therapy for any suitable reason. In some cases, patient 12 may be afflicted with urgency or urge incontinence, and upon perceiving an urge to void, patient 12 may provide input that causes IMD 14 to deliver the second stimulation therapy. In this way, therapy system 10 may provide patient 12 with direct control of the bladder dysfunction therapy.

Programmer 20 is a device configured to communicate with IMD 14, and can be, for example, a key fob or a wrist watch, handheld computing device, computer workstation, or networked computing device. Programmer 20 includes a user interface that receives input from a user (e.g., patient 12, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 20 can additionally or alternatively include a peripheral pointing device, such as a mouse, via which a user may interact with the user interface. In some examples, a display of programmer 20 may include a touch screen display, and a user may interact with programmer 20 via the display. It should be noted that the user may also interact with programmer 20 and/or ICD 16 remotely via a networked computing device.

A user, such as a physician, technician, surgeon, electrophysiologist, or other clinician, may also interact with programmer 20 or another separate programmer (not shown), such as a clinician programmer, to communicate with IMD 14. Such a user may interact with a programmer to retrieve physiological or diagnostic information from IMD 14. The user may also interact with programmer 20 to program IMD 14, e.g., select values for the stimulation parameter values with which IMD 14 generates and delivers stimulation and/or the other operational parameters of IMD 14. For example, the user may use programmer 20 to retrieve information from IMD 14 regarding the bladder contraction frequency of patient 12, bladder cycle durations, and/or voiding events. As another example, the user may use a programmer to retrieve information from IMD 14 regarding the performance or integrity of IMD 14 or other components of system 10, such as leads 16, 18, or a power source of IMD 14. In some examples, this information may be presented to the user as an alert if a system condition that may affect the efficacy of therapy is detected.

In some examples, patient 12 may interact with programmer 20 to control IMD 14 to deliver the second stimulation therapy, to manually abort the delivery of the second stimulation therapy by IMD 14 while IMD 14 is delivering the second stimulation therapy or is about to deliver the second stimulation therapy, or to inhibit the delivery of stimulation therapy by IMD 14, e.g., during voluntary voiding events.

In addition to or instead of interacting with programmer 20 to control therapy delivery, in some examples, patient 12 may interact directly with IMD 14 to control IMD 14 to deliver the second stimulation therapy, manually abort the delivery of the second stimulation therapy, or inhibit the delivery of the stimulation therapy. For example, a motion sensor can be integrated into or on a housing of IMD 14, and the motion sensor can generate a signal that is indicative of patient 12 tapping IMD 14 through the skin. The number, rate, or pattern of taps may be associated with the different programming capabilities, and MD 14 may identify the tapping by patient 12 to determine when patient input is received.

In some examples, programmer 20 provides a notification to patient 12 when the first and/or second stimulation therapies are being delivered or notify patient 12 of the prospective delivery of the first and/or second stimulation therapies to provide patient 12 with the opportunity to manually abort either the first and/or second stimulation therapy. In such examples, programmer 20 may display a visible message, emit an audible alert signal or provide a somatosensory alert (e.g., by causing a housing of programmer 20 to vibrate). After generating the notification, programmer 20 may wait for input from patient 12 prior to delivering the stimulation therapy. Patient 12 may enter input that either confirms delivery of the first or second stimulation therapy is permitted or desirable, or manually aborts the prospective delivery of the first and/or second stimulation therapy. In the event that no input is received within a particular range of time, programmer 20 may, for example, wirelessly transmit a signal that indicates the absence of patient input to IMD 14. IMD 14 may then elect to deliver or not to deliver the stimulation therapy based on the programming of IMD 14.

In examples in which programmer 20 is configured to inhibit delivery of the second stimulation therapy, and, in some cases, the first stimulation therapy, when patient 12 is voluntarily voiding, patient 12 may use programmer 20 to enter input that indicates the patient will be voiding voluntarily. When IMD 14 receives the input from programmer 20, IMD 14 may suspend delivery of the relevant stimulation therapy for a predetermined period of time, e.g., two minutes, to allow patient 12 to voluntarily void. In some examples, the input from patient 12 that indicates the voluntary voiding may also be used to determine a duration of a bladder fill cycle of patient 12 and control the delivery of the first stimulation therapy, as described with respect to FIG. 6.

IMD 14 and programmer 20 may communicate via wireless communication using any techniques known in the art. Examples of communication techniques may include, for example, low frequency or radiofrequency (RF) telemetry, but other techniques are also contemplated. In some examples, programmer 20 may include a programming head that may be placed proximate to the patient's body near the IMD 14 implant site in order to improve the quality or security of communication between IMD 14 and programmer 20.

In some examples, either IMD 14 or programmer 20 may track when IMD 14 delivers the second stimulation therapy to patient 12. Frequent delivery of the second stimulation therapy may be undesirable because, for example, muscle fatigue or adaptation to the stimulation therapy may result. Frequent delivery of the second stimulation therapy may indicate that, as another example, the patient's bladder is full. Programmer 20 can provide a notification to patient 12 when the second stimulation therapy is triggered too frequently. The notification may be triggered based on any suitable criteria, which may be determined by a clinician or automatically programmed into IMD 14 or programmer 20. For example, in the event that the second stimulation therapy is triggered five times within five minutes, programmer 20 may provide a notification to patient 12 indicating the same. This may allow patient 12 to proceed to a bathroom before a leaking episode occurs. The notification provided by programmer 20 may also direct patient 12 to voluntarily void.

Figure 2:
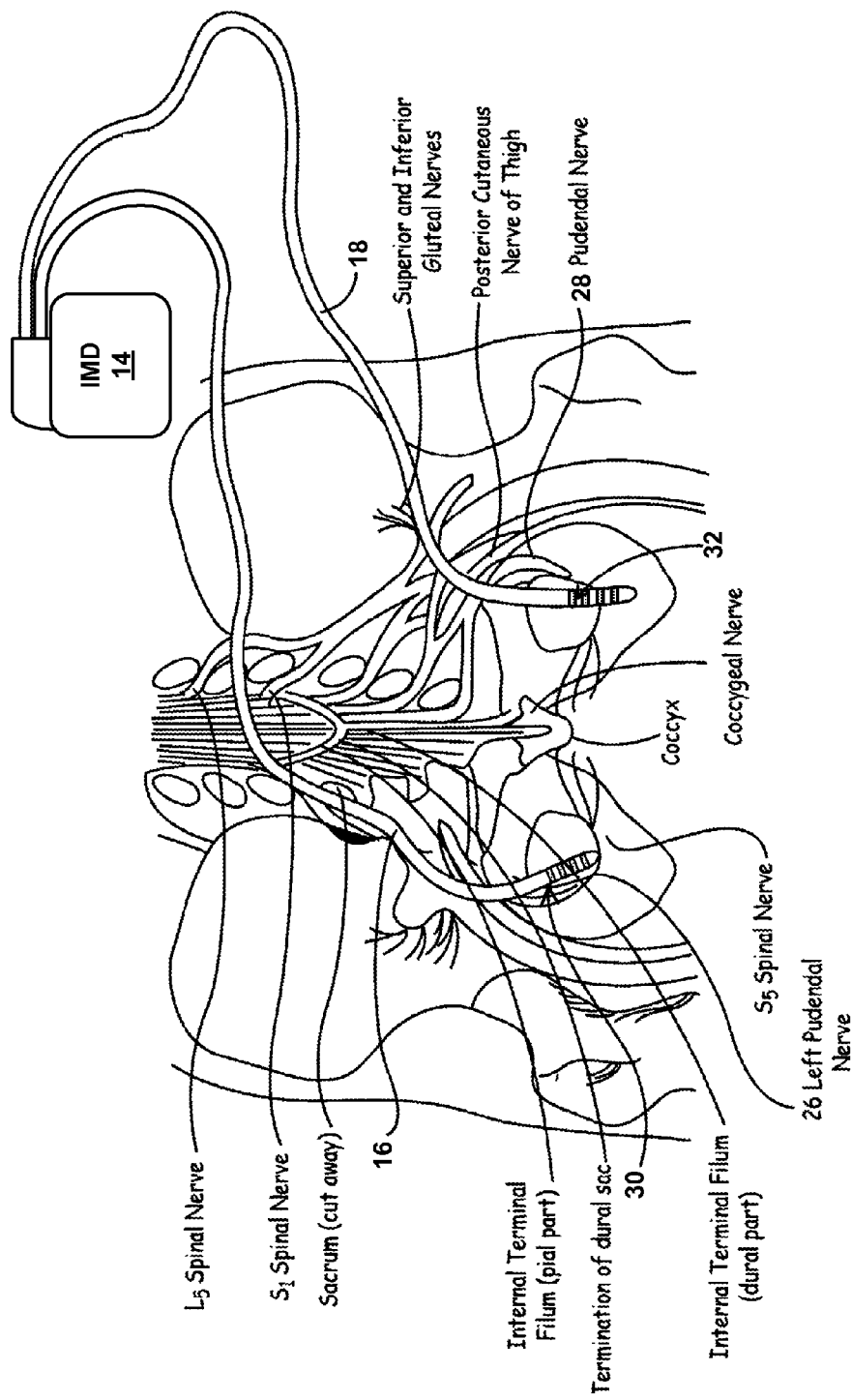
FIG. 2 illustrates a conceptual anatomical view of portions of a pelvic floor of a female patient, and an implanted therapy system that is configured to deliver bilateral stimulation to tissue sites proximate at least one nerve of the pelvic floor.

FIG. 2 is shows a simplified anatomical view of the pelvic floor of a female human patient, the locations of the left and right pudendal nerves 26, 28, respectively, and associated nerves therein, the positioning of IMD 14 and leads 16, 18 such that the distal portions of leads 16, 18 are located near left and right pudendal nerves 26, 28. As shown in FIG. 2, pudendal nerve or nerve portion 26 innervates the pelvic floor muscle and sphincters. Leads 16, 18 are positioned to provide bilateral stimulation to patient 12. In the example shown in FIG. 2, electrodes 30 of lead 16 are positioned to deliver stimulation to modulate activity of left pudendal nerve or nerve portion 26 and electrodes 32 of lead 18 are positioned to deliver stimulation to modulate activity of right pudendal nerve or nerve portion 28. In other examples, electrodes 30, 32 of leads 16, 18, respectively, can be positioned to deliver electrical stimulation to tissue sites proximate other nerves, such as a sacral nerve, and can each be positioned proximate to different nerves or branches of different nerves.

In the example shown in FIGS. 1 and 2, leads 16, 18 are cylindrical. Electrodes 30, 32 of leads 16, 18, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 16, 18. In some examples, segmented electrodes may be useful for targeting different fibers of the same or different nerves to generate different physiological effects. In other examples, one or more of leads 16, 18 may be, at least in part, paddle-shaped (i.e., a "paddle" lead), and may include an array of electrodes on a common surface, which may or may not be substantially flat.

In some examples, one or more of electrodes 30, 32 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12 that results from the delivery of electrical stimulation therapy. An electrical field may define the volume of tissue that is affected when the electrodes 30, 32 are activated. An activation field represents the neurons that will be activated by the electrical field in the neural tissue proximate to the activated electrodes.

System 10 shown in FIGS. 1 and 2 is merely one example of a therapy system that is configured to deliver the first and second stimulation therapies described herein to patient 12, e.g., to generate an inhibitory physiological response in patient 12 to manage a bladder dysfunction of patient 12. Systems with other configurations of leads, electrodes, and sensors are possible. For example, in other implementations, IMD 14 may be coupled to additional leads or lead segments having one or more electrodes positioned at different locations proximate the spinal cord or in the pelvic region of patient 12. The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples. In addition, sensor 22 can be external to patient 12 or incorporated into a common housing as IMD 14 in some examples, and multiple sensors can be used to sense a physiological parameter of patient 12.

As another example configuration, a therapy system can include one or more microstimulators in addition to IMD 14 and leads 16, 18. The microstimulators can have a smaller form factor than IMD 14 and may not be coupled to any separate leads. Rather, the microstimulators can be leadless and configured to generate and deliver electrical stimulation therapy to patient 12 via one or more electrodes on an outer housing of the microstimulators. The microstimulators can be implanted at various locations within the pelvic floor and at different target tissue sites within patient 12, which are selected such that one or more microstimulators can deliver stimulation therapy to target tissue sites on different lateral sides of patient 12. IMD 14 or another microstimulator may act as a "master" module that coordinates the delivery of stimulation to patient 12 via the plurality of microstimulators.

Although a female patient is depicted with reference to FIG. 2, in other examples, the therapy system and regimen described herein may also be used to treat male patients.

Figure 3:
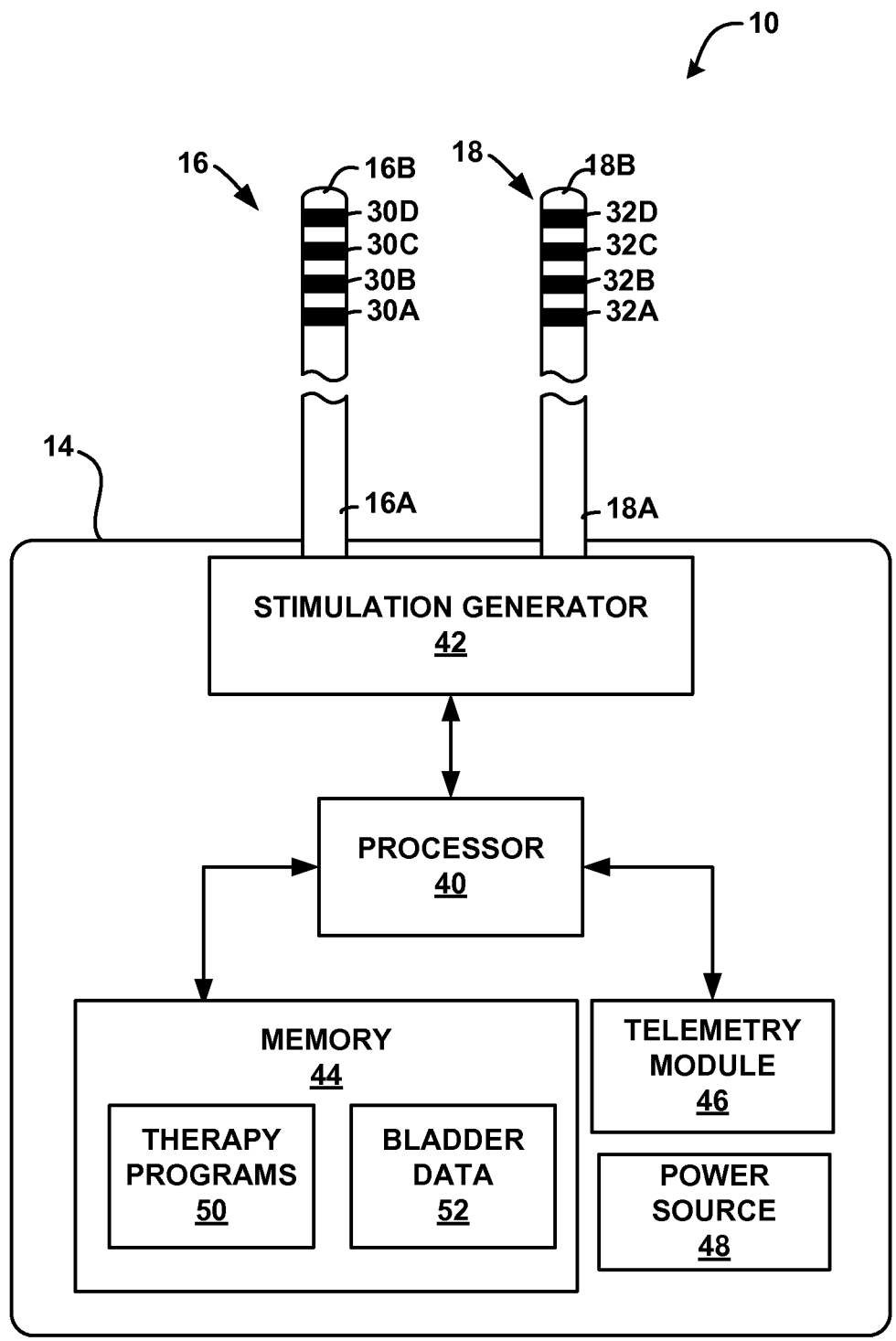
FIG. 3 is a block diagram illustrating an example configuration of an implantable medical device (IMD), which may be utilized in the systems shown in FIGS. 1 and 2.

FIG. 3 is a block diagram illustrating example components of IMD 14. In the example of FIG. 3, IMD 14 includes processor 40, stimulation generator 42, memory 44, telemetry module 46, and power source 48. In other examples, IMD 14 may include a fewer or greater number of components. For example, in some examples, sensor 22 can be a part of IMD 14 and substantially enclosed within the same outer housing as stimulation generator 42.

In the example shown in FIG. 3, leads 16, 18 are electrically coupled to stimulation generator 42, such that stimulation generator 42 can deliver electrical stimulation signals to patient 12 via any subset of electrodes 30A-30D (collectively referred to as "electrodes 30") of lead 16 and electrodes 32A-32D (collectively referred to as "electrodes 32") of lead 18. In some examples, as described above with respect to FIG. 1, each set of electrodes 30, 32 is positioned on opposite sides of a midline of patient 12 to deliver electrical stimulation to respective lateral sides of patient 12. A proximal end 16A, 18A of each lead 16, 18, respectively, extends from the housing of IMD 14 and a distal end 16B, 18B of each lead 16, 18, respectively, extends to a target therapy site. If therapy system 10 is used to treat bladder dysfunction, the target tissue sites can be, for example, proximate a sacral nerve, a pudendal nerve, a tibial nerve, a dorsal genital nerve, an inferior rectal nerve, a perineal nerve, a hypogastric nerve, a urinary sphincter, or any combination thereof.

In general, IMD 14 comprises any suitable arrangement of hardware, alone or in combination with software and/or firmware, to perform the techniques attributed to IMD 14 and processor 40, stimulation generator 42, and telemetry module 46 of IMD 14. In various examples, processor 40 can include any one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may also include a memory 44, which include any volatile or non-volatile media, such as a random access memory (RAM), read only memory (ROM), non-volatile RAM (NYRAM), electrically erasable programmable ROM (EEPROM), flash memory, and the like. Although processor 40, stimulation generator 42, and telemetry module 46 are described as separate modules, in some examples, processor 40, stimulation generator 42, and telemetry module 46 can be functionally integrated. In some examples, processor 40, stimulation generator 42, telemetry module 46 correspond to individual hardware units, such as ASICs, DSPs, FPGAs, or other hardware units.

Memory 44 stores stimulation therapy programs 50 that specify stimulation parameter values for the stimulation therapy provided by IMD 14. In some examples, stimulation therapy programs 50 include stimulation therapy programs for the first stimulation therapy and the second stimulation therapy. In some examples, memory 44 also stores bladder data 52, which processor 40 may use for controlling the timing of the delivery of the stimulation therapy. For example, bladder data 52 can include parameters for detecting bladder conditions (e.g., volume or contractions) and trigger events, e.g., patient conditions for which the delivery of the second stimulation therapy is desirable. Example values include, for example, threshold values or baseline values for at least one of bladder impedance, bladder pressure, sacral or pudendal afferent nerve signals, bladder contraction frequency, or external urinary sphincter EMG templates. As described in further detail below, the threshold values and baseline values may indicate a particular event, such as a bladder contraction or a condition indicative of a voiding-related physiological condition (e.g., a patient state in which there is a relatively high likelihood of an involuntary voiding event). Other example values that processor 40 can use to detect trigger events include a time of day or a timer duration, which, as described above with respect to FIG. 1, can be based on a bladder fill cycle of patient 12.

Bladder data 52 can also include information related to sensed bladder contractions, bladder impedance and/or posture of patient 12, which may be recorded for long-term storage and retrieval by a user, or used by processor 40 for adjustment of stimulation parameters, such as amplitude, pulse width, and pulse rate. Memory 44 may also store instructions for execution by processor 40, in addition to stimulation therapy programs 50 and bladder data 52. In some examples, memory 44 includes separate memories for storing instructions, electrical signal information, stimulation therapy programs, and bladder data.

Stimulation generator 42 delivers electrical stimulation to tissue of patient 12 via selected electrodes 30, 32 carried by leads 16, 18, respectively. In some examples, processor 40 controls stimulation generator 42 by selectively accessing and loading at least one of stimulation therapy programs 50 from memory 44 to stimulation generator 42. In some cases, a clinician or patient 12 may select a particular one of stimulation therapy programs 50 from a list using a programming device, such as programmer 20 or a clinician programmer. Processor 40 may receive the selection via telemetry module 46. In the example shown in FIG. 1 in which one IMD 14 delivers bilateral stimulation to patient 12 at different times or at substantially the same time, stimulation generator 42 can include at least two independently controllable stimulation channels. The independently controllable channels permits stimulation delivered to the lateral sides of patient 12 can be unilaterally adjusted as needed. In other examples, such as examples in which separate IMDs deliver stimulation to respective lateral sides of patient 12, the IMD can include one or more independently controllable stimulation channel.

Stimulation generator 42 generates and delivers stimulation therapy, i.e., electrical stimulation, according to stimulation parameters. In some examples, stimulation generator 42 delivers therapy in the form of electrical pulses. In such examples, relevant stimulation parameters may include a voltage amplitude, a current amplitude, a pulse rate, a pulse width, a duty cycle, or the combination of electrodes 30, 32 with which stimulation generator 42 delivers the stimulation signals to tissue of patient 12. In other examples, stimulation generator 42 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 30, 32 with which stimulation generator 42 delivers the stimulation signals to tissue of patient 12.

In some examples, the stimulation parameters for the stimulation programs 50 may be selected to relax the patient's bladder, e.g., to reduce a bladder contraction frequency. An example range of stimulation parameter values for the stimulation therapy that are likely to be effective in treating bladder dysfunction, e.g., when applied to the spinal, sacral, pudendal, tibial, dorsal genital, inferior rectal, or perineal nerves, are as follows:

1. Frequency or pulse rate: between about 0.1 Hertz (Hz) and about 20 Hz.
2. Amplitude: between about 0.1 volts and about 50 volts, such as between about 0.5 volts and about 2.0 volts, or between about 1 volt and about 10 volts. For some patients, the threshold intensity level may be at an amplitude level less than or equal to about 2 volts to about 4 volts, though this may differ between patients. For current controlled systems, the amplitude may be between about 0.1 milliamps (mA) and about 50 mA, such as between about 0.5 mA and about 20 mA, or between about 1 mA and about 10 mA.

3. Pulse Width: between about 100 microseconds (μs) and about 400 μs.

Additionally, in some examples, the stimulation parameters for the first stimulation therapy may include the parameters that define the therapy cycle, which includes a first time period ("on" periods) during which IMD 14 actively delivers a stimulation signal to patient 12 and a second time period ("off" periods), during which IMD 14 does not deliver any stimulation to patient 12. When stimulation generator 42 delivers the first stimulation therapy according to such a therapy cycle, a stimulation signal is not continuously delivered to patient 12, but periodically delivered (e.g., only during the first time period). As described in further detail below, in some examples, the therapy cycle defines a schedule by which stimulation generator 42 delivers the first stimulation therapy in an open loop manner.

In some examples, the first and second time periods discussed herein may have durations on the order of minutes. For example, the first time period, during which IMD 14 delivers the first stimulation therapy, may be between about 5 minutes and about 20 minutes, such as about 10 minutes. In some examples, the second time period, during which IMD 14 ceases to deliver the first stimulation therapy, is at least about five minutes, such as between about five minutes and about 30 minutes or between about 10 minutes and about 20 minutes. In some examples, the relative lengths of the first and second time periods may be selected to provide advantageous battery life to IMD 14 compared to an IMD 14 that delivers stimulation therapy substantially continuously.

The stimulation parameter values for the first stimulation therapy can be selected, e.g., from the parameter values listed above, such that the first stimulation therapy elicits a first inhibitory physiological response related to voiding of patient 12 during the first time period and a second inhibitory physiological response related to voiding of patient 12 during the second time period. In some examples, the first and second inhibitory physiological responses related to voiding include a reduction in a bladder contraction frequency, and may differ from each other by the percentage by which the bladder contraction frequency is reduced. Depending on the stimulation parameter values, the second physiological response related to voiding of patient 12 elicited by the first stimulation therapy during the second time period can be greater than the first physiological response of patient 12. In this way, in some examples, the first stimulation therapy delivered by stimulation generator 42 may elicit a post-stimulation inhibitory effect that extends beyond the first time period, into the second time period.

In some examples, the stimulation parameters are selected such that the first stimulation therapy elicits substantially no inhibitory physiological response related to voiding of patient 12 during the first time period. In other words, the physiological response of patient 12 may be substantially similar during the first time period and during a time period prior to the first time period during which stimulation generator 42 does not deliver stimulation therapy to patient 12.

At least some of stimulation therapy programs 50 define the first stimulation therapy delivered by IMD 14. Stimulation generator 42 may generate the stimulation signals for the first stimulation therapy based on one stimulation therapy program 50, such that stimulation is delivered to each lateral side of patient 12 according to the same therapy program, or based on multiple therapy programs that differ from each other by at least one therapy parameter value. For example, stimulation generator 42 may deliver stimulation to a first lateral side of patient 12 according to a first therapy program and deliver stimulation to a second lateral side of patient 12 at different times according to a second therapy program that differs from the first therapy program by at least one therapy parameter value.

Stimulation therapy programs 50 also include therapy programs with which stimulation generator 42 generates and delivers the second stimulation therapy delivered by IMD 14. In some examples, stimulation generator 42 generates and delivers stimulation signals to both lateral sides of patient 12 at the same time based on one stimulation therapy program 50. In other examples, stimulation generator 42 generates and delivers stimulation signals to a first lateral side of patient 12 according to one stimulation therapy program 50 and to the other lateral side of patient 12 according to a different stimulation therapy program 50 at substantially the same time.

As discussed above, in some examples, stimulation generator 42 generates and delivers the first stimulation therapy in an open loop manner. In these examples, at least some of stimulation therapy programs 50 define values for the durations of the first and second time periods. In such cases, stimulation generator 42 delivers stimulation to patient 12 during each of the first time periods according to the same stimulation parameter values. Additionally, the first and second time periods alternate and each first time period has the same duration and each second time period has the same duration. In some examples, stimulation generator 42 continues to deliver stimulation therapy to patient 12 according to these stimulation parameters until receiving an instruction from processor 40 to interrupt therapy delivery. In some examples, processor 40 may issue such an instruction to stimulation generator 42 in response to detecting a trigger event that causes processor 40 to control stimulation generator 42 to generate and deliver the second stimulation therapy.

In other examples, stimulation generator 42 delivers the first stimulation therapy to patient 12 in a closed loop manner. As described below with respect to FIG. 8, in closed loop stimulation therapy, processor 40 controls stimulation generator 42 to deliver the first stimulation therapy to patient 12 based on at least one feedback, e.g., a signal representative of a physiological response of patient 12 sensed by at least one of sensor 22 or a subset of electrodes 30, 32 of leads 16, 18. For example, processor 40 may control stimulation generator 42 to deliver the first stimulation therapy to patient 12 upon detecting a bladder contraction frequency of patient 12 that is greater than or equal to a threshold bladder contraction frequency or a baseline contraction frequency. Accordingly, the control of stimulation therapy delivery by processor 40 or stimulation generator 42 may include controlling a duration of the second time period during which stimulation generator 42 does not deliver the first stimulation therapy to patient 12. In these examples, bladder data 52 can include a baseline contraction frequency and/or a threshold contraction frequency for patient 12.

In some examples, an inhibitory physiological response of patient 12 to the first stimulation therapy may be observed during a post-stimulation period (also referred to herein as a second time period), in these examples, processor 40 can control stimulation generator 42 to deliver the first stimulation therapy to patient 12 during a first time period (which can be predetermined) and cease delivering the first stimulation therapy for a second time period. Processor 40 can then determine when to resume delivery of the first stimulation therapy, i.e., to restart the first time period, by comparing a monitored bladder contraction frequency to a threshold contraction frequency or a baseline contraction frequency.

For example, when the bladder contraction frequency is one of equal to the baseline contraction frequency, within a certain range of the baseline contraction frequency, or is greater than or equal to the threshold contraction frequency, processor 40 controls stimulation generator 42 to deliver the first stimulation therapy to patient 12. As an example, processor 40 may compare the determined bladder contraction frequency and the baseline contraction frequency to determine a difference between the determined contraction frequency and the baseline contraction frequency. In some examples, when the difference is less than or equal to a specified value (e.g., a threshold difference value), processor 40 may control stimulation generator 42 to initiate delivery of the first stimulation therapy to patient 12. In other words, processor 40 may end the second time period and initiate the first time period based on the difference between the determined contraction frequency and the baseline contraction frequency.

In some examples, bladder data 52 stores parameters with which processor 40 detects a bladder contraction of patient 12 based on a sensed physiological parameter, which can be sensed via sensor 22 or another sensor (e.g., a sensing module of IMD 14). In some examples, processor 40 monitors impedance of a bladder of patient 12 to detect a bladder contraction. An example of a therapy system that is configured to determine an impedance of a bladder of patient 12 is described with respect to FIG. 16. Thus, bladder data 52 can include a threshold impedance value that is indicative of the bladder contraction. Processor 40 may, for example, determine an impedance of the bladder and compare the determined impedance value to a threshold impedance value stored in memory 44 as bladder data 52. When the determined impedance value is less than the threshold impedance value stored in bladder data 52, processor 40 detects a bladder contraction. Processor 40 can determine a bladder contraction frequency by, for example, monitoring impedance of the bladder for a predetermined duration of time to detect bladder contractions, and determining a number of bladder contractions in the predetermined duration of time.

In other examples, sensor 22 may be a pressure sensor and processor 40 may detect bladder contractions based on changes in bladder pressure indicated by the pressure sensor. Thus, in some examples, bladder data 52 includes a pressure value or a pressure change that is indicative of a bladder contraction. Processor 40 may determine a pressure value based on signals received from sensor 22 and compare the determined pressure value to a threshold value stored in bladder data 52 to determine whether the signal is indicative of a bladder contraction. Processor 40 can monitor bladder pressure to detect bladder contractions for a predetermined duration of time, and determine a bladder contraction frequency by determining a number of contractions of bladder in the predetermined time period.

In some cases, sensor 22 may be an EMG sensor, and processor 40 can detect bladder contractions based on an EMG of a muscle that is being monitored. The muscle is selected to be a muscle that is activated (e.g., contracts) when the patient's bladder contracts, and can be, for example, a bladder wall, a detrusor muscle, or a urinary sphincter muscle. Thus, in some examples, bladder data 52 includes an EMG template or a threshold signal characteristic value (e.g., an amplitude value) that is indicative of a bladder contraction. Processor 40 may compare a characteristic of a sensed EMG signal or the signal waveform itself to the threshold signal characteristic value or EMG template stored in bladder data 52 to determine whether the signal is indicative of a contraction of bladder.

In examples in which stimulation generator 42 generates and delivers the first stimulation therapy in a closed loop manner, bladder data 52 stores at least one parameter for controlling the closed loop therapy delivery. As discussed above, example parameters include a threshold contraction frequency and a baseline contraction frequency. A baseline contraction frequency may be bladder contraction frequency at a time prior to delivery of stimulation therapy by stimulation generator 42. For example, the baseline bladder contraction frequency may be determined by processor 40 after implantation of IMD 14 in patient 12, but before stimulation generator 42 delivers any stimulation therapy to patient 12. In some examples, the baseline bladder contraction frequency may represent the patient state when no therapeutic effects from delivery of stimulation by IMD 14 are present.

Processor 40 may determine the baseline bladder contraction frequency utilizing signals representative of physiological parameters received from at least one of sensor 22 or by sensing module of IMD 14 (not shown in FIG. 3), which can sense a physiological parameter of patient 12 via a subset of electrodes 30, 32 of leads 16, 18, respectively, or via a different set of electrodes. In some implementations, processor 40 may, automatically or under control of a user, determine the threshold bladder contraction frequency based on a baseline bladder contraction frequency. For example, the threshold contraction frequency can be a predetermined percentage of the baseline bladder contraction frequency or a percentage of the baseline bladder contraction frequency input by a user via programmer 20. As one example, the threshold frequency may be between approximately 75% and approximately 100% of the baseline bladder contraction frequency.

In other examples, the threshold bladder contraction frequency may not be based on a baseline bladder contraction frequency of patient 12, and may instead be based on clinical data collected from a plurality of patients. For example, the threshold contraction frequency may be determined based on an average bladder contraction frequency of a plurality of patients during a bladder filling time period, e.g., during a time period in which the plurality patients are not experiencing a voluntary or involuntary voiding event. In any case, the threshold contraction frequency may be stored in bladder data 52, and, in some examples, processor 40 may utilize the threshold contraction frequency when delivering stimulation therapy in a closed loop manner to patient 12.

In other examples, instead of utilizing a threshold bladder contraction frequency or a baseline bladder contraction frequency, processor 40 may control closed-loop delivery of the first stimulation therapy based on an EMG template, EMG characteristics (e.g., an amplitude or frequency value of an EMG), or bladder pressure value, which can each indicate a bladder state in which delivery of the first stimulation therapy is desirable. Thus, bladder data 52 can include an EMG template, EMG characteristics, or threshold bladder pressure value in some examples. The EMG template, EMG characteristics, and bladder pressure values can be determined using any suitable technique. In some cases, processor 40 may generate the EMG template or determine the threshold bladder pressure value based on received signals generated by sensor 22 after implantation of IMD 14, but before stimulation generator 42 delivers any stimulation therapy to patient 12. The stored pressure value, EMG template or EMG characteristics with which processor 40 controls the delivery of the first stimulation therapy can indicate a bladder contraction intensity that is indicative of a patient condition in which the first stimulation therapy is desirable, e.g., to reduce the bladder contraction frequency or otherwise reduce the possibility of an occurrence of an involuntary voiding event.

In examples in which sensor 22 includes an EMG sensor, processor 40 may compare an EMG collected during the second time period to an EMG template stored as bladder data 52 to determine whether the contractions of bladder are indicative of a predetermined characteristic which causes processor 40 to control stimulation generator 42 to initiate delivery of the first stimulation therapy. The predetermined characteristic may be a frequency of contractions of bladder, an amplitude of the signal (representative of intensity of contractions of bladder), or the like. For example, the EMG may indicate whether the bladder contractions of patient 12 have returned to a baseline contraction frequency or pattern, such that delivery of the first stimulation therapy is desirable.

Closed loop therapy may allow processor 40 and stimulation generator 42 to deliver more efficacious therapy to patient 12 by timing the delivery of stimulation to respond to a specific physiological state (e.g., a particular bladder contraction frequency or bladder contraction intensity) of patient 12. For example, based on the determined bladder contraction frequency, processor 40 may cause stimulation generator 42 to initiate delivery of the first stimulation therapy to patient 12 prior to the end of the second time period specified in the selected one of therapy programs 50. In this manner, closed loop therapy may reduce or substantially eliminate an amount of time that a bladder contraction frequency is at a baseline level (e.g., a level substantially similar to the contraction frequency of bladder prior to delivery of any stimulation therapy). In examples in which delivery of the first stimulation therapy generates a delayed inhibitory physiological response, timing the delivery of the first stimulation therapy to occur prior to observation of the baseline bladder contraction frequency may help provide sufficient time for the first stimulation therapy to generate the desired inhibitory physiological response.

Stimulation generator 42 delivers the first stimulation therapy to patient 12, and upon detecting a trigger event, processor 40 controls stimulation generator 42 to cease delivery of the first stimulation therapy and deliver the second stimulation therapy to patient 12, which includes substantially simultaneous bilateral stimulation. As discussed with respect to FIG. 1, the trigger event can include, for example, detection of a physiological condition indicative of an increased possibility of an involuntary voiding event or an imminent involuntary voiding event, a time of day, expiration of a timer, and/or input from the patient (or a patient caretaker).

In examples in which the trigger event is based on a physiological parameter of patient 12 sensed by sensor 22 (or another sensor), bladder data 52 can store values for detecting the trigger event based on a signal generated by sensor 22. One example of a trigger event is a bladder volume greater than or equal to a trigger event threshold bladder volume. As a volume of the patient's bladder increases, so may the possibility of an involuntary voiding event, such that at the threshold bladder volume, delivery of the more acute therapy provided by the second stimulation therapy may be desirable to provide efficacious therapy to patient 12. A bladder volume can be determined based on, for example, an impedance of a pathway through the bladder.

Another example of a trigger event is a bladder contraction frequency or intensity that is greater than or equal to a trigger event threshold. A relatively high bladder contraction frequency or bladder contraction intensity can indicate an increased possibility of an involuntary voiding event. In some examples, the bladder contraction frequency or intensity increases as the patient's bladder volume increases. Bladder data 52 can include the trigger event threshold, which processor 40 can later reference to detect the trigger event. Any of the techniques described above can be used to determine bladder contraction frequency or intensity. The trigger event threshold may be different than that used to control closed loop delivery of the first stimulation therapy. With respect to bladder contraction frequency and bladder contraction intensity, the trigger event threshold for initiating the delivery of the second stimulation therapy is greater than the threshold used to initiate the delivery of the first stimulation therapy (i.e., restart the first time period). Because the second stimulation therapy is used as a secondary therapy that supplements the first stimulation therapy, the thresholds for triggering the delivery of the second stimulation therapy are higher, such that the second stimulation therapy is used less often and only when the additional layer of therapy is desirable to help prevent the occurrence of an involuntary voiding event.

Another example of a trigger event is an activity or posture state. In this example, bladder data 52 can include the output of sensor 22 (or another sensor) that is indicative of a patient activity level or patient posture state associated with an increased probability of an occurrence of an involuntary voiding event. Memory 44 may associate patient posture states or activity levels with the second stimulation therapy, such that when processor 40 detects a posture state or activity level associated with the second stimulation therapy, processor 40 controls stimulation generator 42 to generate and deliver the second stimulation therapy to patient 12.

Processor 40 can determine an activity level of patient 12 based on a motion sensor that generates a signal that changes as a function of patient activity level using any suitable technique. For example, processor 40 may determine an activity level of patient 12 by sampling the signal from the motion sensor (e.g., sensor 22 in some examples) and determine a number of activity counts during a sample period, where a plurality of activity levels are associated with respective activity counts. In one example, processor 40 compares the signal generated by the motion sensor to one or more amplitude thresholds stored within memory 44, and identifies each threshold crossing as an activity count. Processor 40 may determine a patient posture state based on a signal from the motion sensor using any suitable technique. In one example, a posture state may be defined as a three-dimensional space (e.g., a posture cone or toroid), and whenever a posture state parameter value, e.g., a vector from a three-axis accelerometer of the motion sensor resides within a predefined space, processor 40 indicates that patient 12 is in the posture state associated with the predefined space.

In examples in which processor 40 controls the delivery of the second stimulation therapy based on a time of day, bladder data 52 can store the one or more times of day at which processor 40 initiates the delivery of the second stimulation therapy. Processor 40 can include a clock that tracks the time of day.

in examples in which a timer is used to control the timing of the delivery of the second stimulation therapy, bladder data 52 can store the duration of the timer. As discussed above with respect to FIG. 1, in some examples, the duration of the tinier is based on the bladder fill cycle of patient 12. In some examples, processor 40 selects the duration of the timer and stores it as bladder data 52, or a clinician can select the duration of the timer and transmit the duration to IMD 14 (e.g., via programmer 20) for storage as bladder data 52.

Other trigger events, such as other the trigger events that indicate a physiological condition indicative of an increased possibility of an involuntary voiding event or an imminent involuntary voiding event, are contemplated. Moreover, any of the trigger events described herein can be used in any suitable combination to initiate the delivery of the second stimulation therapy.

The threshold values (also referred to as threshold levels) or templates (e.g., indicating a signal indicative of an imminent voiding event) stored in memory 44 as bladder data 52 may be determined using any suitable technique. In some examples, the threshold values may be determined during implantation of IMD 14 or during a trial period in a clinician's office following implant of IMD 14. The trigger event threshold values, times of day, or timer durations may be adapted over time based on user input, e.g., via external programmer 20. As an example, patient 12 may indicate, via programmer 20, when an involuntary voiding event takes place. When the patient input is received, processor 40 may determine a bladder impedance value during the event or immediately prior to the event based in signals received from sensor 22. A new trigger event threshold value may be determined using this impedance value. As another example, the trigger event threshold value stored as bladder data 52 may based on a running average of bladder impedance values measured during involuntary voiding events.

in some examples, stimulation generator 42 delivers the second stimulation therapy for a predetermined therapy period, the duration of which may be stored in memory 44 and/or a memory of another device (e.g., programmer 20). The therapy period may be, for example, approximately 10 seconds to approximately 60 seconds, although other therapy periods are contemplated. The predetermined period of time can be determined by a clinician in some examples and stored in memory 44 of IMD.

In some examples, in addition to or instead of the predetermined therapy period, stimulation generator 42 delivers the second stimulation therapy for a therapy period controlled by patient 12. In such examples, patient 12 may interact with programmer 20 to control the delivery time. As an example, stimulation generator 42 may deliver the second stimulation therapy as long as patient 12 presses a button on a keypad or touch screen of programmer 20. As another example, processor 40 controls stimulation generator 42 to initiate the delivery of the second stimulation therapy upon receiving a first input from patient 12 (e.g., by presses a button on a keypad or touch screen of programmer 20) and controls stimulation generator 42 to terminate the delivery of the second stimulation therapy upon receiving a second subsequent input from patient 12 indicating the second stimulation therapy should be terminated. In operation, processor 40 can receive the patient input via telemetry module 46 and control stimulation generator 42 to deliver therapy according to the received input.

If processor 40 controls the duration of the therapy period of the second stimulation therapy based on both a predetermined period of time and the patient input, processor 40 can, for example, control stimulation generator 42 to deliver the second stimulation therapy for the longer of the predetermined period of time or the period of time determined based on patient input, or, in other examples, the shorter of those two periods of time.

In other examples, processor 40 controls the duration of the therapy period during which stimulation generator 42 delivers the second stimulation therapy based on a physiological condition of patient 12. For example, in examples in which stimulation generator 42 initiates the delivery of the second stimulation therapy based on a sensed patient condition, stimulation generator 42 delivers the second stimulation therapy until the condition is no longer detected. As an example, processor 40 can control stimulation generator 42 to initiate the delivery of the second stimulation therapy in response to detecting a bladder impedance less than or equal to a predetermined trigger event threshold and continue delivering the second stimulation therapy until the bladder impedance is greater than the predetermined trigger event threshold. This threshold may be different than that used to detect a bladder contraction. When processor 40 detects a bladder impedance that is greater than the predetermined termination threshold, processor 40 may determine that the volume of the patient's bladder has decreased (e.g., due to voluntary voiding by patient 12), such that termination of the second stimulation therapy is appropriate. In the foregoing example, stimulation generator 42 delivers the second stimulation therapy until a relatively low bladder fill level of patient 12 is detected.

A relatively low bladder level of patient 12 that causes stimulation generator 42 to terminate delivery of the second stimulation therapy can be detected using other techniques. In some examples, as described with respect to FIG. 6, processor 40 detects a relatively low bladder fill level of patient 12 based on patient input that is provided after patient 12 voluntarily voids. Processor 40 can receive the input from an input device separate from IMD 12 (e.g., programmer 20) via telemetry module 46 or from a sensor that is coupled to processor 40 (e.g., a motion sensor that detects tapping of IMD 14 by patient 12).

Telemetry module 46 includes any suitable hardware, firmware, software or any combination thereof for communicating with another device, such as programmer 20 (FIG. 1). Generally, processor 40 controls telemetry module 46 to exchange information with medical device programmer 20 and/or another device external to IMD 14. Under the control of processor 40, telemetry module 46 may receive downlink telemetry, e.g., patient input, from and send uplink telemetry, e.g., an alert, to programmer 20 with the aid of an antenna, which may be internal and/or external. Processor 40 may provide the data to be uplinked to programmer 20 and the control signals for the telemetry circuitry within telemetry module 46, and receive data from telemetry module 46. Processor 40 may transmit operational information and receive stimulation programs or stimulation parameter adjustments via telemetry module 46. Also, in some examples, IMD 14 may communicate with other implanted devices, such as stimulators, control devices, or sensors, via telemetry module 46.

Processor 40 monitors patient input received via telemetry module 46 and takes appropriate action. As previously described, in some examples, telemetry module 46 may receive an indication from programmer 20 that patient 12 provided input indicative of an imminent voiding event or a request for delivery of the second stimulation therapy. Upon receiving the patient input via telemetry module 46, processor 40 may control stimulation generator 42 to generate and deliver the second stimulation for a predetermined amount of time or until a particular patient condition is detected, to manually abort the second stimulation therapy, or inhibit the second stimulation therapy during voluntary voiding.

Telemetry module 46 can also receive patient input indicating a voluntary voiding event. In response to receiving the input, processor 40 may suspend delivery of the second stimulation therapy, and, in some examples, the first stimulation therapy, for a pre-determined period of time, e.g., 2 minutes. During this time period, processor 40 may ignore signals indicative of the patient parameter, such as signals generated by sensor 22. Processor 40 may ignore these signals for a predetermined period of time, such as approximately two minutes. After two minutes has elapse, processor 40 may resume the first stimulation therapy if the first stimulation therapy was suspended, and continue monitoring patient 12 to detect trigger events. As discussed above, the input indicative of the voluntary voiding event can also be used to control the duration of the second stimulation therapy.

Power source 60 delivers operating power to the components of IMD 14. Power source 60 may include a battery and a power generation circuit to produce the operating power. In some examples, the battery may be rechargeable to allow extended operation.

Figure 4:
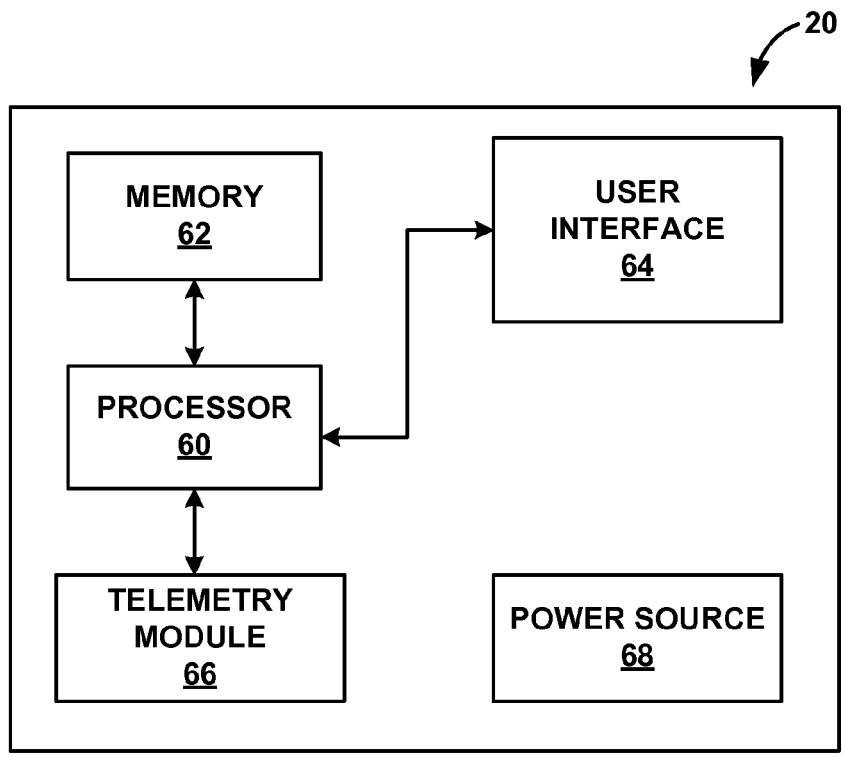
FIG. 4 is a block diagram illustrating an example configuration of an external programmer which may be utilized in the systems shown in FIGS. 1 and 2.

FIG. 4 is a block diagram illustrating example components of external programmer 20. While programmer 20 may generally be described as a hand-held computing device, the programmer may be a notebook computer, a cell phone, or a workstation, for example. As illustrated in FIG. 4, external programmer 20 may include a processor 60, memory 62, user interface 64, telemetry module 66, and power source 68. Memory 62 may store program instructions that, when executed by processor 60, cause processor 60 and external programmer 20 to provide the functionality ascribed to external programmer 20 throughout this disclosure.

In general, programmer 20 comprises any suitable arrangement of hardware, alone or in combination with software and/or firmware, to perform the techniques attributed to programmer 20, and processor 60, user interface 64, and telemetry module 66 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 62, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although processor 60 and telemetry module 66 are described as separate modules, in some examples, processor 60 and telemetry module 66 are functionally integrated.

Memory 62 may store program instructions that, when executed by processor 60, cause processor 60 and programmer 20 to provide the functionality ascribed to programmer 20 throughout this disclosure. In some examples, memory 62 may further include therapy information, e.g., therapy programs defining the first stimulation therapy and second stimulation therapy, similar to those programs 50 (FIG. 3) stored in memory 44 of IMD 14, and bladder data similar to bladder data 52 stored by IMD 14. The stimulation programs and/or bladder data 42 stored in memory 62 may be downloaded into memory 44 of IMD 14 or vice versa.

User interface 64 may include a button or keypad, lights, a speaker for voice commands, a display, such as a LCD, LED, or CRT. In some examples the display may be a touch screen. As discussed in this disclosure, processor 60 may present and receive information relating to stimulation therapy via user interface 64. For example, processor 60 may receive patient input via user interface 64. The input may be, for example, in the form of pressing a button on a keypad or selecting an icon from a touch screen.

Processor 60 may also present information to patient 12 (or a patient caretaker) in the form of alerts related to delivery of the stimulation therapy to patient 12 via user interface 64. Telemetry module 66 supports wireless communication between IMD 14 and programmer 20 under the control of processor 60. Telemetry module 66 may also be configured to communicate with another computing device via wireless communication techniques, or direct communication through a wired connection. Telemetry module 66 may be substantially similar to telemetry module 46 described above, providing wireless communication via an RF or proximal inductive medium. In some examples, telemetry module 66 may include an antenna, which may take on a variety of forms, such as an internal or external antenna. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 20 without needing to establish a secure wireless connection.

An external antenna that is coupled to programmer 20 may correspond to a programming head that may be placed over IMD 14. Although not shown, programmer 20 may additionally or alternatively include a data or network interface to another computing device, to facilitate communication with the other device, and presentation of information relating to first and second stimulation therapies via the other device.

IMD 14 and/or programmer 20 may control of the timing of the delivery of the first stimulation therapy and the second stimulation therapy that generate one or more physiological responses to manage bladder dysfunction of patient 12. If external programmer 20 controls the stimulation, programmer 20 may transmit therapy programs for implementation by processor 40 to IMD 14. Alternatively, programmer 20 may transmit a signal to IMD 14 indicating that processor 40 should execute locally stored programs or therapy routines. In such a manner, control over the electrical stimulation may be distributed between IMD 14 and external programmer 20, or may reside in either one alone.

In one example, patient 12 may control the second stimulation therapy delivered by IMD 14 via programmer 20. For example, patient 12 may initiate and/or terminate delivery of the second stimulation therapy by IMD 14 via user interface 64. In this way, patient 12 may use programmer 20 to deliver the second stimulation therapy "on demand," such as when patient 12 senses the onset of a leakage episode or undertakes an activity in which an additional measure of therapy to help prevent the occurrence of an involuntary voiding event is desirable.

In some examples, patient 12 may indicate an intent to void via user interface 64, and processor 60 may implement a blanking interval through communication of the indication to IMD 14 via telemetry module 66. For example, processor 60 may transmit a command signal to IMD 14 that indicates processor 40 of IMD 14 should temporarily suspend delivery of the second stimulation therapy or both the first and second stimulation therapies so that the stimulation does not interfere with the patient's ability to void. In some examples, patient 12 can indicate the length of time for a voiding event by pressing and holding down a button of user interface 64 for the duration of a voiding event, pressing a button a first time to initiate voiding and a second time when voiding is complete. In other times, programmer 20 or IMD 14 automatically determinates a duration of a voiding event based on a predetermined period of time following the indication of voluntary voiding provided by patient 12. In each case, programmer 20 causes IMD 14 to temporarily suspend the relevant stimulation therapy so that voluntary voiding is possible.

In examples in which patient 12 provides input, via user interface 64, indicative of the completion of a voluntary voiding event, processor 60 may transmit a signal to processor 40 of IMD 14 via the respective telemetry modules 66, 46. Processor 40 of IMD 14 may then, as described above, control the duration of the second stimulation therapy to patient 12 based on this input, such as by terminating the delivery of the second stimulation therapy upon receiving the input indicative of the completion of a voluntary voiding event.

Power source 68 delivers operating power to the components of programmer 20. Power source 68 may include a battery and a power generation circuit to produce the operating power. In some examples, the battery may be rechargeable to allow extended operation.

Figure 5:
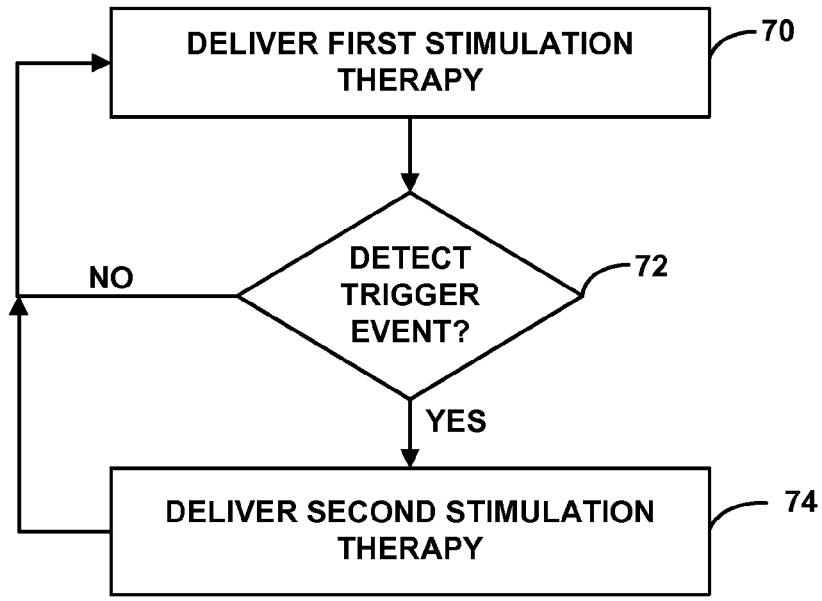
FIG. 5 is a flow diagram that illustrates an example technique for delivering stimulation therapy to a patient, where the therapy includes a first stimulation therapy and a second stimulation therapy.

FIG. 5 is a flow diagram illustrating an example technique implemented by a therapy system, such as therapy system 10 (FIG. 1), to reduce the likelihood of incontinence events. While FIGS. 5-8 are described with respect to therapy system 10, in other examples, the techniques for the first and second stimulation therapies described herein may be implemented by other therapy systems, which may include different components or configurations than therapy system 10. In addition, while processor 40 is primarily referred to in FIGS. 5-8, in other examples, a processor of another device (e.g., programmer 20), alone or in combination with processor 40, can perform the techniques shown in FIGS. 5-8.

In the technique shown in FIG. 5, under control of processor 40, stimulation generator 42 of IMD 14 delivers the first stimulation therapy to patient 12 (70). In some examples, processor 40 initiates the delivery of the first stimulation therapy by stimulation generator 42 upon activation of chronic therapy delivery by the clinician. Stimulation generator 42 delivers stimulation to target tissue sites on respective lateral sides of patient 12 at different times (e.g., in a time interleaved manner). In some examples, the target tissues are each proximate at least one of a spinal nerve, a sacral nerve, a pudendal nerve, dorsal genital nerve, a tibial nerve, an inferior rectal nerve, a perineal nerve, or a branch thereof on the respective lateral side of patient 12.

In one example, stimulation generator 42 delivers the first stimulation by delivering substantially balanced bilateral stimulation to patient 12, whereby the stimulation delivered to a first target tissue site on a first lateral side of patient 12 is substantially similar in intensity and/or duration as the stimulation delivered to a second target tissue site on a second lateral side of patient 12. In other examples, for the first stimulation therapy, the stimulation delivered to the two lateral sides of patient 12 is imbalanced, e.g., due to different stimulation intensities and/or stimulation periods in which IMD 14 is actively delivering stimulation to patient 12.

Figure 8:
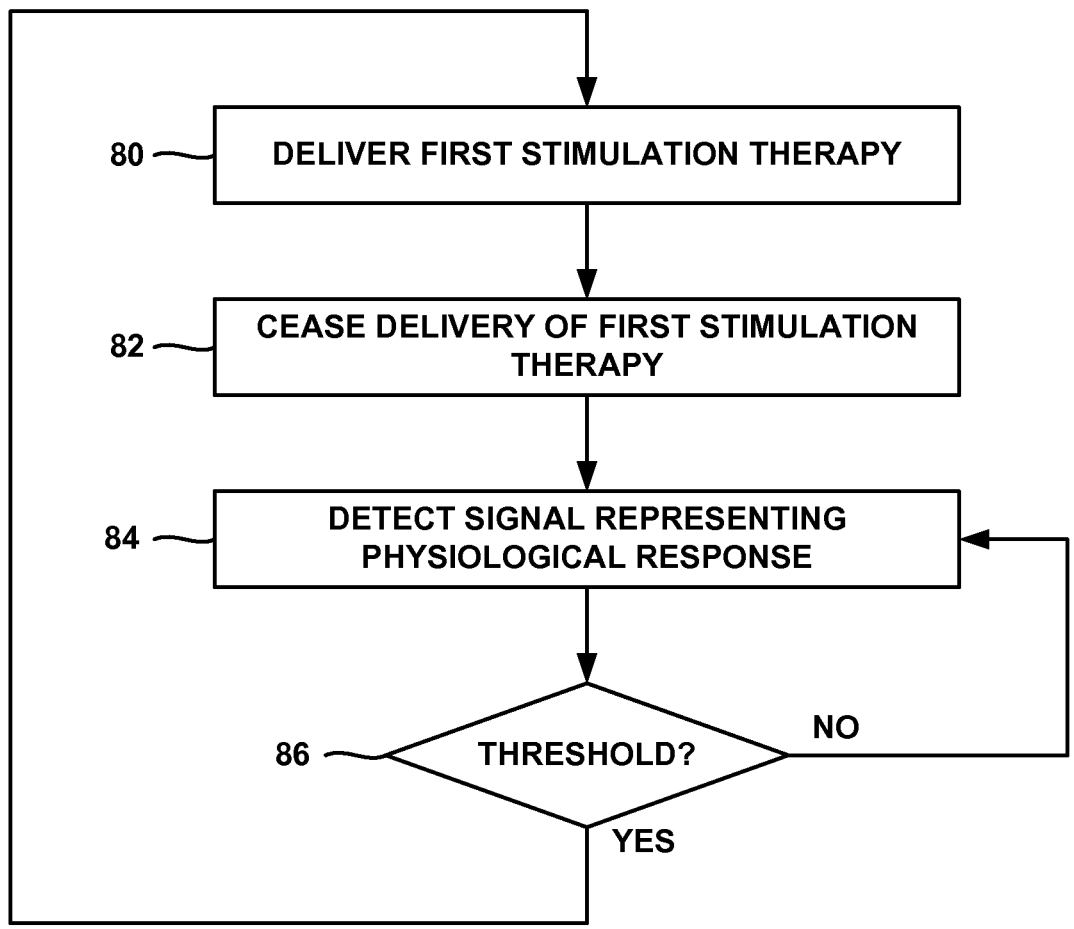
FIG. 8 is a flow diagram that illustrates an example technique for delivering a first stimulation therapy in a closed loop manner.

Processor 40 controls stimulation generator 42 to generate and deliver the first stimulation therapy to patient 12 in an open loop manner, or, as discussed in further detail with respect to FIG. 8, in a closed loop manner. In either example, the first stimulation therapy can be configured to provide an immediate inhibition of a physiological response related to voiding (e.g., a reduction in bladder contraction frequency) or a more delayed response, in which the physiological response is not observed until after stimulation generator 42 delivers stimulation to patient 12.

Processor 40 determines whether a trigger event is detected (72). Examples of trigger events that may be detected include, but are not limited to, bladder contraction or intensity level exceeding (e.g., greater than or equal to) a trigger event threshold level, abnormal detrusor muscle activities (e.g., as indicated by an EMG), patient activity level exceeding a threshold level, a particular patient posture state or activity level, a time of day, expiration of a timer, and patient input. As previously described, processor 40 may monitor bladder impedance, bladder pressure, pudendal or sacral afferent nerve signals, a urinary sphincter EMG, or any combination thereof to detect changes in bladder contraction and/or intensity level. These physiological parameters may be sensed by, for example, sensor 22 or another sensor (e.g., a sensing module that is a part of IMD 14).

The steps of delivering the first stimulation therapy and detecting a rigger event are illustrated in FIG. 5 as being sequential, but it should be understood that these steps may be performed simultaneously instead of sequentially. For example, processor 40 can detect the trigger event while the first stimulation therapy is being delivered to patient 12.

If processor 40 does not detect a trigger event after initiating delivery of the first stimulation therapy ("NO" branch of block 72), stimulation generator 42 continues to deliver the first stimulation therapy (70) without delivering the second stimulation (70). On the other hand, if processor 40 detects a trigger event after initiating delivery of the first stimulation therapy ("YES" branch of block 72), processor 40 controls stimulation generator 42 to deliver the second stimulation therapy by at least delivering stimulation substantially simultaneously to both lateral sides of patient 12 (74). As previously described, the second stimulation therapy is selected to have a different physiological effect on patient 12 than the first stimulation therapy, such as a more immediate decrease in bladder contraction frequency or a more drastic decrease e.g., greater decrease) in bladder contraction frequency. In the example shown in FIG. 5, the first and second stimulation therapies are delivered at different times. The substantially simultaneous bilateral stimulation can be substantially balanced between the lateral sides of patient 12 in some examples and can be imbalanced in other examples.

In one example, the trigger event is a bladder fill level at or above a threshold fill level. The trigger event can be detected, for example, when processor 40 detects a bladder impedance value that is less than a trigger event threshold impedance value stored in memory 44 as bladder data 52 (FIG. 3). Other techniques for determining a bladder fill level are contemplated, such as based on a strain gauge sensor (which can be, for example, sensor 22) on a bladder surface. In another example, the trigger event is a bladder contraction frequency greater than or equal to a trigger even threshold value. Any suitable technique, such as those described above, can be used to detect a bladder contraction. In another example, the trigger event is a bladder contraction intensity greater than or equal to a trigger even threshold value. The bladder contraction intensity can be determined using any suitable technique, such as, but not limited to, a pressure value sensed by sensor 22. In another example, the trigger event is a predetermined patient posture state or activity level, which can be stored in memory 44 (FIG. 3) of IMD 14 or memory of another device.

In addition to or instead of the trigger events that are based on a sensed patient parameter, the trigger event can be patient input. Patient 12 may provide the patient input via user interface 64 of programmer 20, e.g., by activating a button on a keypad or select an icon using a touch screen of programmer 20. Programmer 20 wirelessly communicates the patient input to IMD 14 via the respective telemetry modules 66, 46. In other examples, patient 12 may provide input indicating the delivery of the second stimulation therapy is desirable by directly interacting with IMD 14. For example, IMD 14 may include a motion sensor that detects movement of IMD 14 and patient 12 may provide input by tapping the skin proximate IMD 14 in a predetermined pattern, such that processor 40 detects the movement and characterizes the movement as patient input.

In another example, the trigger event is an expiration of a timer that processor 40 starts upon receiving an indication that patient 12 has voluntarily voided, thereby reducing the bladder fill level or even emptying the bladder. The duration of the timer can be, for example, selected to be a duration of time that is expected to pass before the bladder of patient 12 is filled to a level that increases the possibility of an involuntary voiding event. Thus, at the expiration of the timer, the bladder of patient 12 is at a volume for which an additional layer of therapy provided by the second stimulation therapy is desirable to help prevent the occurrence of an involuntary voiding event. Processor 40 can receive an indication that patient 12 has voluntarily voided using any suitable technique, e.g., receiving input from patient 12 (or a patient caretaker) via programmer 20 or by directly interacting with IMD 14 or based on a physiological parameter sensed by IMD 14 or sensor 22 that indicates a bladder volume.

In some examples, stimulation generator 42 delivers the second stimulation therapy (74) for a therapy period duration controlled by patient 12. For example, patient 12 may control the duration of the therapy period for the second stimulation therapy by interacting with programmer 20, e.g., by pressing a button on a keypad or a touch screen to terminate the second stimulation therapy or set a duration of time for the second stimulation therapy, or by interacting directly with IMD 14 (e.g., by tapping skin superior to the implanted IMD 14). IMD 14 can be programmed with a maximum duration for the second stimulation therapy, such that patient 12 is provided with limited control of the duration of the second stimulation therapy. The maximum duration for the second stimulation therapy can be, for example, approximately 3 minutes, although other durations of time are contemplated.

In addition to or instead of determining the therapy period duration based on patient input, stimulation generator 42 can deliver the second stimulation therapy (74) for a predetermined period of time, e.g., about 10 seconds to about 50 seconds, immediately following the detection of the trigger event. The duration of the predetermined period of time may be selected such that an imminent involuntary voiding event is suppressed. After the predetermined period of time, processor 40 controls stimulation generator 42 to resume delivery of the first stimulation therapy (70), unless some intervening input is received that causes stimulation generator 42 to suspend delivery of stimulation therapy to patient 12.

After terminating the delivery of the second stimulation therapy to patient 12, stimulation generator 42 continues to deliver the first stimulation therapy (70) and the technique shown in FIG. 5 is repeated as necessary. Thus, IMD 14 delivers the first stimulation therapy and, when triggered, delivers the second stimulation therapy for a limited duration of time (e.g., shorter in duration than the duration of time that the first stimulation therapy is delivered).

Figure 6:
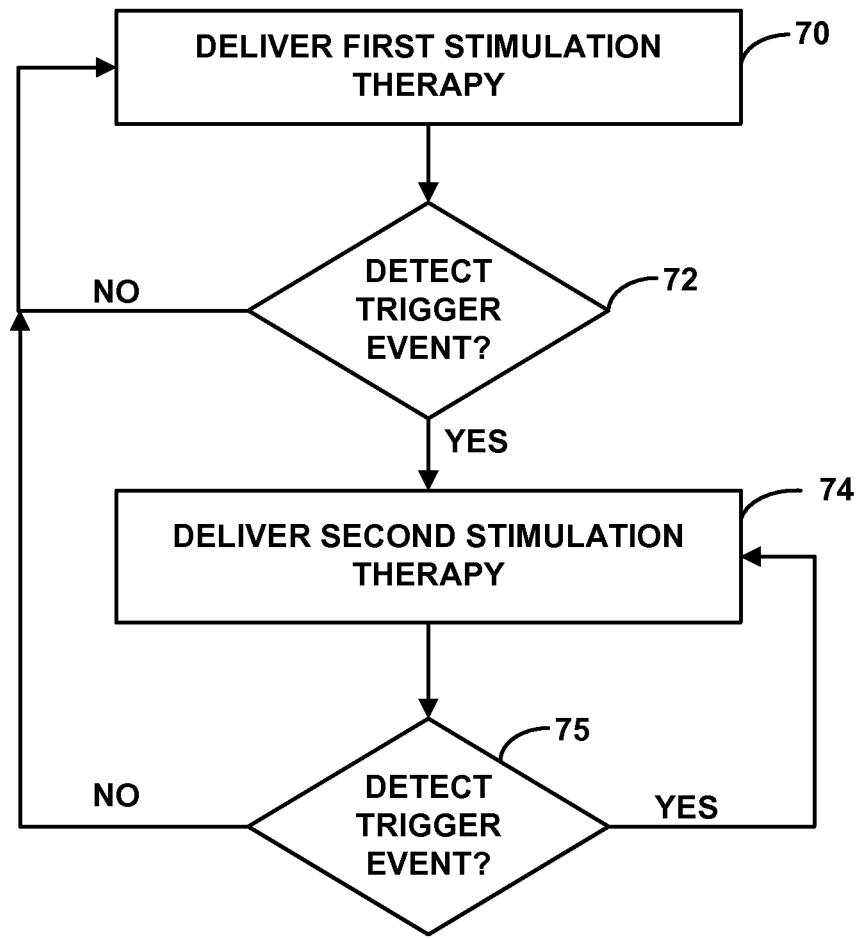
FIG. 6 is a flow diagram of another example technique for delivering first and second stimulation therapies to a patient.

FIG. 6 is a flow diagram of another technique with which processor 40 can control stimulation generator 42 to generate and deliver the first and second stimulation therapies. As shown in the flow diagram of FIG. 6, after stimulation generator 42 delivers the second stimulation therapy for a predetermined period of time, processor 40 can determine whether the trigger event is still present (75) using any of the techniques described above with respect to FIG. 5. For example, if the trigger event is the detection of a particular patient condition, processor 40 can determine whether the patient condition that triggered the delivery of the second stimulation therapy is still observed. As an example, processor 40 may determine whether the bladder contractions are still greater than or equal to a trigger event threshold value. As another example, if the trigger event is patient input, processor 40 can determine whether the patient has provided additional input that indicates delivery of the second stimulation therapy is desirable.

If the trigger event is still detected after the delivery of the second stimulation therapy ("YES" branch of block 75), processor 40 may control stimulation generator 42 to deliver the second stimulation therapy (74) again for another predetermined period of time. This technique may be repeated in some examples until the trigger event is no longer detected. If the trigger event is not detected after delivery of the second stimulation therapy for a predetermined duration of time ("NO" branch of block 75), processor 40 can cease delivery of the second stimulation therapy and resume delivery of the first stimulation therapy (74). In other examples, processor 40 can cease delivery of the second stimulation therapy and resume the first stimulation therapy when a feedback indicates the first stimulation therapy is desirable, e.g., the first stimulation therapy can be controlled in a closed loop manner. A closed loop technique with which processor 40 may control the first stimulation therapy is described with respect to FIG. 8.

Figure 7:
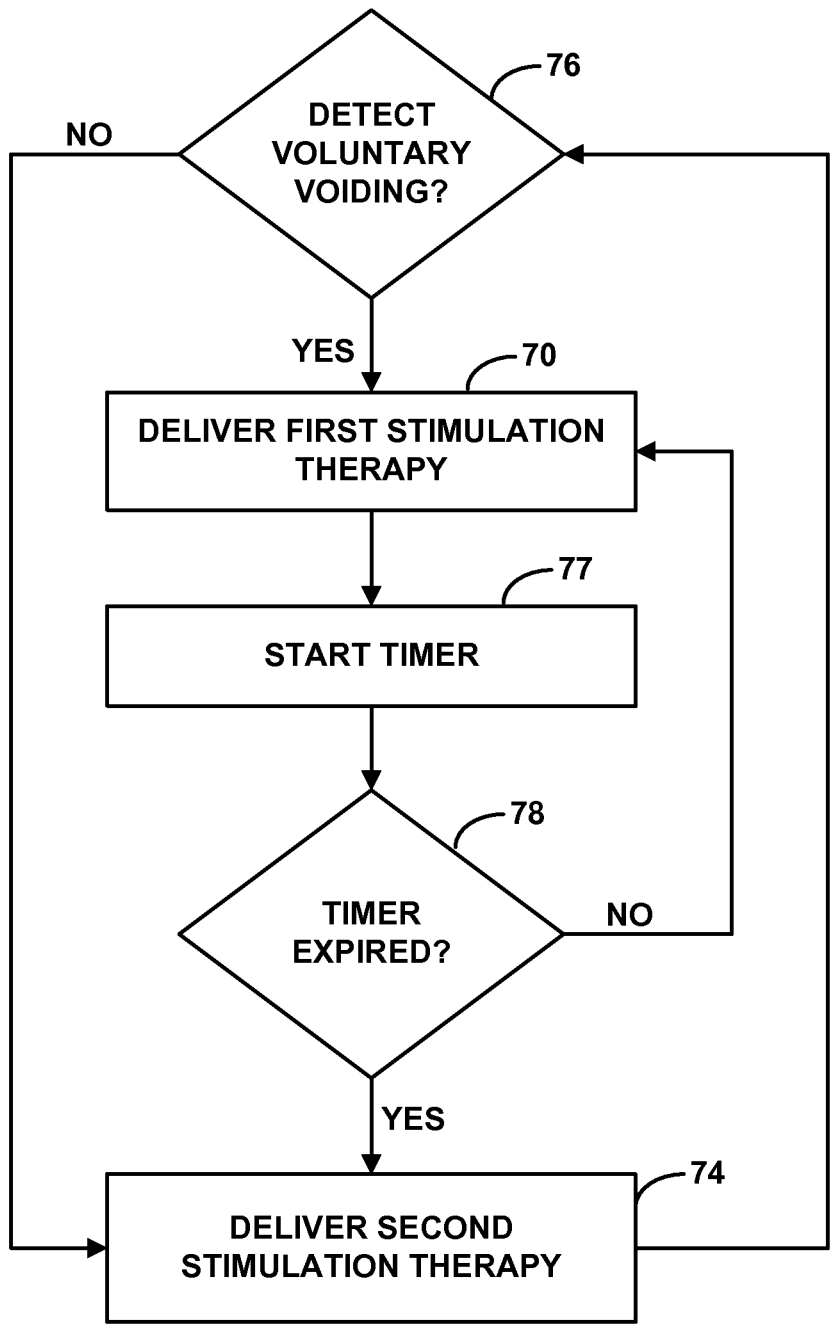
FIG. 7 is a flow diagram of another example technique for delivering first and second stimulation therapies to a patient, which includes delivering the second stimulation therapy until a voluntary voiding event of the patient is detected.

FIG. 7 is a flow diagram of another technique with which processor 40 can control stimulation generator 42 to generate and deliver the first and second stimulation therapies. In the technique shown in FIG. 7, stimulation generator 42 delivers the second stimulation therapy to patient 12 for a therapy period that has a duration that is based on voiding by patient 12. The technique shown in FIG. 7 is performed in a closed loop manner.

To initiate of the delivery of therapy to patient 12, processor 40 detects a voiding event ("YES" branch of block 76), in which patient 12 voids and decreases the fill level of the bladder. The voiding event is voluntary in the example shown in FIG. 7 examples. Processor 40 can detect voiding by patient 12 using any suitable technique. In some examples, processor 40 receives input from patient 12 (or a patient caretaker) indicating the occurrence of a voluntary voiding event. Patient 12 can provide input to programmer 20 or another external device, which may then transmit an indication of the input to processor 40, or patient 12 may interact directly with IMD 14 (e.g., by tapping skin superior to the implant site of IMD 14).

In other examples, processor 40 detects an occurrence of a voiding event based on a sensed physiological parameter of patient 12. For example, processor 40 can detect the occurrence of a voluntary voiding event based on an EMG of the urinary sphincter muscle of patient 12 or another muscle that activates during voiding. Sensor 22 (FIG. 1) may generate the EMG in some examples, or processor 40 may sense the EMG of the muscle via a subset of electrodes 30, 32 of leads 16, 18 (FIG. 3). In some examples, memory 44 of IMD 14 (FIG. 3) stores an EMG template or threshold values (e.g., a signal amplitude or frequency value) that is associated with a voluntary voiding event, and processor 40 compares a sensed EMG to the stored template or threshold to detect the voluntary voiding event. For example, when a sensed EMG substantially matches the stored template, processor 40 may determine that patient 12 is purposefully activating the monitored muscle to voluntarily void. A voluntary voiding event can also be detected based on other physiological parameters, such as a bladder pressure, urinary sphincter pressure, and the like. In addition, other techniques for detecting a voluntary voiding event may be used. Similar techniques can be used to detect an involuntary voiding event and processor 40 can be configured to distinguish between voluntary and involuntary voiding events.

After detecting a voluntary voiding event, processor 40 controls stimulation generator 42 to deliver the first stimulation therapy (70) and starts a timer (77). As discussed above, the duration of the timer is predetermined and stored in memory 44 of IMD 14 and/or a memory of another device. The timer duration may be based on a bladder fill cycle of patient 12. As shown in FIG. 7, stimulation generator 42 continues to deliver the first stimulation therapy to patient 12 until the timer expires. Upon expiration of the timer ("YES" branch of block 78), processor 40 controls stimulation generator 42 to terminate delivery of the first stimulation therapy and deliver the second stimulation therapy to patient 12 (74). In the example shown in FIG. 7, processor 40 delivers the second stimulation therapy to patient 12 until a voluntary voiding event is detected ("NO" branch of block 76). When the voluntary voiding event is detected, processor 40 may terminate the delivery of the second stimulation therapy, and, in some cases, resume the first stimulation therapy at that time, or at a later time, such as when a patient condition indicative of a desirability for the first stimulation therapy is detected.

The technique shown in FIG. 7 adapts the timing of the second stimulation therapy to the bladder fill cycle of patient 12. A bladder fill cycle begins immediately after the patient voluntarily voids. As time passes since the patient's last voluntary voiding event, the patient's bladder fills, such that the possibility of the occurrence of an involuntary voiding event may be increase through the bladder fill cycle because, at least with some patients, the bladder contraction frequency may increase as the fill level of the patient's bladder increases. In this way, the second stimulation therapy, which may provide a greater inhibitory physiological response that reduces the bladder contraction frequency of patient 12 compared to the first stimulation therapy, may be more desirable as the bladder fill cycle of patient 12 progresses, e.g., some period of time after a voluntary voiding event of patient 12.

Upon detecting a voluntary voiding event ("YES" branch of block 76), processor 40 may terminate the delivery of the second stimulation therapy and initiate the delivery of the first stimulation therapy (70), thereby restarting the therapy cycle shown in FIG. 7. In examples in which the first stimulation therapy is delivered according to a therapy cycle that includes a first time period in which stimulation is delivered to patient 12 and a second time period in which no stimulation is delivered to patient 12, processor 40 can initiate the delivery of the first stimulation therapy in the first time period or the second time period. For example, processor 40 can terminate the delivery of the second stimulation therapy and deliver electrical stimulation to patient until a patient condition for which the first stimulation therapy is desirable is detected, e.g., using the technique shown in FIG. 8.

After patient 12 voluntarily voids, the bladder fill cycle of patient 12 restarts, such that the possibility of the occurrence of an involuntary voiding event is reduced, thereby meriting delivery of the first stimulation therapy, which provides a less intense inhibitory physiological response. As discussed above, patient 12 may exhibit a relatively tow bladder contraction frequency at the beginning of the bladder fill cycle that may gradually increase throughout the bladder fill cycle.

Using the techniques shown in FIGS. 5-7, IMD 14 can provide responsive stimulation to patient 12 to manage bladder dysfunction. Delivering the second stimulation therapy upon detection of a trigger event, rather than on a substantially regular basis, may help reduce muscle fatigue by limiting the amount of the second stimulation therapy, which has a higher intensity than the first stimulation therapy. In addition, implementing the second stimulation therapy only when needed may help conserve power of power source 48 (FIG. 3) of IMD 14. Conserving power may help elongate the useful life of IMD 14.

FIG. 8 is a flow diagram illustrating an example technique for delivering the first stimulation therapy in a closed loop manner. The therapy cycle for the closed loop therapy shown in FIG. 8 includes a first time period during which stimulation generator 42 delivers stimulation to patient 12 and a second time period during which stimulation generator 42 does not deliver stimulation to patient 12. In the example illustrated in FIG. 8, the duration of the second time period may be adjusted by processor 40 in response to an input received from sensor 22 or another sensor. In other examples, the duration of the second time period may be adjusted in response to another input, e.g., from a user such as patient 12 or a clinician or another sensing module of therapy system 10. In some examples, in addition to or as an alternative to adjusting the duration of the second time period, the duration of the first time period may be adjusted based on an input received by processor 40.

Processor 40 controls stimulation generator 42 to deliver the first stimulation therapy to patient 12 via a subset of electrodes 30, 32, where the stimulation is defined by a therapy program (80). As described above, the first stimulation therapy delivered during the first time period according to the therapy program may elicit substantially no inhibitory physiological response related to voiding in patient 12 during the first time period, or may elicit a first inhibitory physiological response related to voiding in patient 12 during the first time period. In some examples, the first inhibitory physiological response related to voiding includes a reduction in bladder contraction frequency.

At the end of the first time period, processor 40 controls stimulation generator 42 to cease delivering stimulation (82) and detects a signal indicative of a physiological response of patient 12 to the stimulation delivery according to the therapy program during the first time period (84). In the example shown in FIG. 8, the physiological response is determined based on a bladder contraction frequency of patient 12. In the example shown in FIG. 8, processor 40 compares the bladder contraction frequency, to a threshold value, such as contraction frequency or a baseline contraction frequency (86). When processor 40 determines that the bladder contraction frequency of patient 12 is above the threshold value or within a predetermined amount of the baseline contraction frequency ("YES" branch of block 86), processor 40 controls stimulation generator 42 to initiate delivery of the first stimulation to patient 12 (80). This restarts the first period of time of the therapy cycle. However, when processor 40 determines that the bladder contraction frequency of bladder of patient 12 is below the threshold value or within a predetermined amount of the baseline contraction frequency ("NO" branch of block 86), processor 40 may continue to detect the signal representing the physiological response (84) until the bladder contraction frequency of interest is detected.

The steps of delivering the first stimulation therapy and monitoring patient 12 to detect contractions of bladder are illustrated in FIG. 8 as being sequential, but it should be understood that these steps may be performed simultaneously instead of sequentially. For example, processor 40 may detects a signal representing a physiological response (84) while controlling stimulation generator 42 to deliver the first stimulation therapy (80) and after controlling stimulation generator 42 to cease delivery of the first stimulation therapy (82).

Figure 9A:
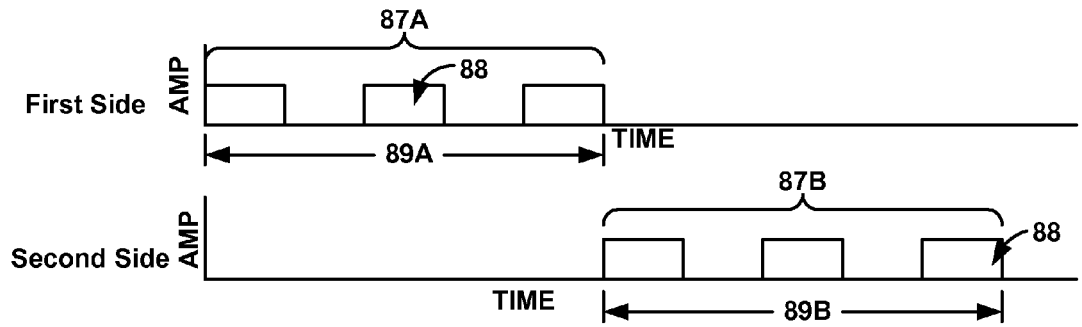
FIGS. 9A-9C are schematic illustrations of example stimulation signals delivered to the first and second sides of a patient during the first electrical stimulation therapy.
Figure 9B:
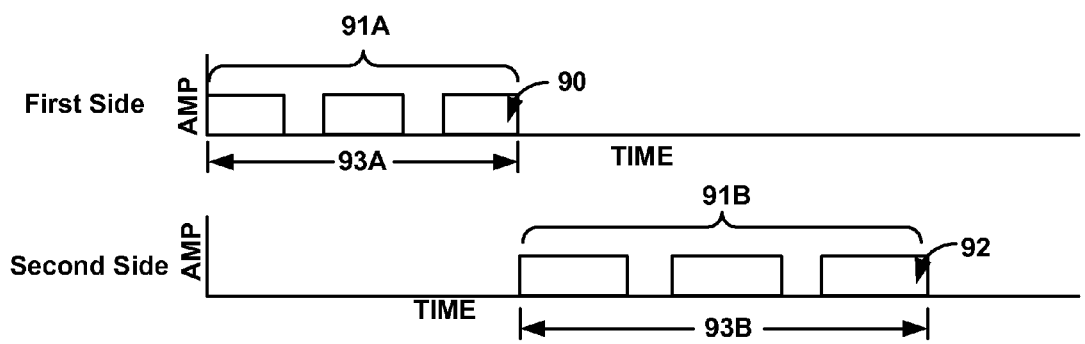
Figure 9C:
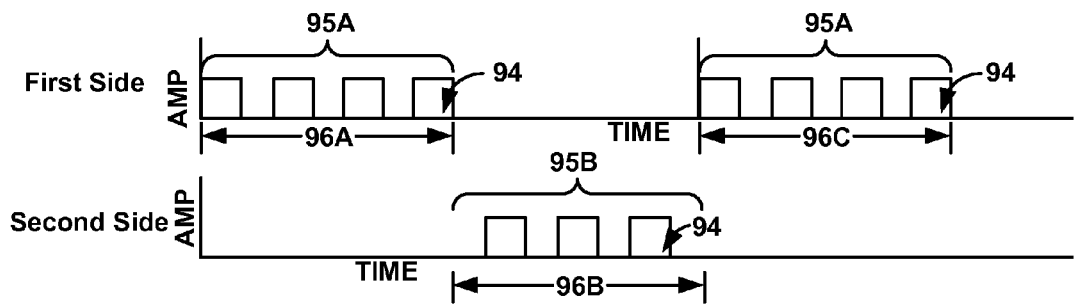

FIGS. 9A-9C are schematic illustrations of stimulation signals delivered to the first and second lateral sides of patient 12 during the first electrical stimulation therapy. The first and second lateral sides can be, for example, the left and right sides of patient 12, where the left and right sides are demarcated by spinal cord 24 in FIG. 1. While FIGS. 9A-9C, as well as FIGS. 10A-10F, illustrate stimulation pulses, in other examples, IMD 14 may generate and deliver continuous time signals. Substantially similar stimulation regimes as those shown in FIGS. 9A-10F can be adapted for use with continuous time signals.

In the examples shown in FIGS. 9A-9C, when stimulation generator 42 of IMD 14 delivers stimulation signals to the first and second lateral sides of patient 12 at different times, the stimulation signals do not overlap in time. FIG. 9A illustrates a stimulation pulse regime in which IMD 14 delivers the first stimulation therapy to patient 12 by delivering stimulation pulses to the first and second lateral sides of patient 12 in an alternating fashion (e.g., a time interleaved manner). In the example pulse regime shown in FIG. 9A, each stimulation pulse 88 has substantially the same pulse width and amplitude, such that the first and second lateral sides of patient 12 receive substantially similar intensities of stimulation. In this way, FIG. 9A illustrates a substantially balanced bilateral stimulation therapy in which the first and second lateral sides of patient 12 receive stimulation signals in alternating time slots.

As shown in FIG. 9A, IMD 14 delivers a first pulse train 87A to a first lateral side of patient 12 during a first stimulation period 89A, where pulse train 87A includes a plurality of electrical stimulation pulses 88. After first stimulation period 89A, IMD 14 stops delivery of stimulation to the first lateral side of patient 12 and initiates delivery of second pulse train 87B to a second lateral side of patient 12 during a second stimulation period 89B. Second pulse train 87B also includes a plurality of pulses 88. Second stimulation period 89B immediately follows first stimulation period 89A. Although not shown in FIG. 9A, after second stimulation period 89B, IMD 14 may stop delivery of stimulation to the second lateral side of patient 12 and initiate delivery of another pulse train 87A for a third stimulation period that is equal in duration to first stimulation period 87A. Thereafter, IMD 14 may deliver pulse train 87B to second lateral side of patient 12 for a stimulation period equal to stimulation period 89B, and so on and so forth. This alternating delivery of stimulation to the lateral sides of patient 12 may continue as long as desired.

As shown in FIG. 9A, during first stimulation period 89A, IMD 14 does not deliver electrical stimulation to the second lateral side of patient 12, and during second stimulation period 89B, IMD 14 does not deliver electrical stimulation to the first lateral side of patient 12. As discussed in further detail below, stimulation periods 89A, 89B may be substantially equal (e.g., equal or nearly equal) in some examples, and may be different in other examples. In addition, pulse trains 87A, 88A may be substantially equal number of pulses 88 (e.g., equal or nearly equal) in some examples, and may have a different number of pulses in other examples.

FIG. 9B illustrates an example of an imbalanced first stimulation therapy in which the first and second lateral sides of patient 12 receive different stimulation pulses, and in which the stimulation periods and pulse train lengths differ for each lateral side. IMD 14 also delivers stimulation pulses to the first and second lateral sides of patient 12 in an alternating fashion in the example shown in FIG. 9B. In particular, IMD 14 delivers pulse train 91A including a plurality of stimulation pulses 90 to a first side of patient 12 during first stimulation period 93A, and, after the end of first stimulation period 93A, IMD 14 stops delivery of stimulation to the first lateral side of patient 12 and initiates delivery of second pulse train 91B including a plurality of stimulation pulses 92 to a second lateral side of patient 12 during second stimulation period 93B. Second stimulation period 93B does not overlap with first stimulation period 93A. Although not shown in FIG. 9B, after second stimulation period 939, IMD 14 may stop delivery of stimulation to the second lateral side of patient 12 and initiate delivery of another pulse train 91A for a third stimulation period that is equal in duration to first stimulation period 93A. This alternating delivery of stimulation to the lateral sides of patient 12 may continue as long as desired.

Stimulation pulses 90, 92 have substantially similar amplitudes, but have different pulse widths. In other examples, stimulation pulses delivered to different lateral sides of patient 12 may have substantially similar pulse widths, but different pulse amplitudes. Due to the different stimulation pulses 90, 92, different pulse train 91A, 91B, and different stimulation periods 93A, 93B, the first and second lateral sides of patient 12 receive different intensities of stimulation, such that the bilateral stimulation therapy shown in FIG. 9B is imbalanced. In other examples, imbalanced stimulation first stimulation therapy may be achieved using other techniques, such as with similar stimulation period durations, but different pulse trains.

FIG. 9C illustrates another example of an imbalanced first stimulation therapy. IMD 14 delivers stimulation pulses 94 to the first and second lateral sides of patient 12 at different times in the example shown in FIG. 9C. While each stimulation pulse 94 delivered to the lateral sides of patient 12 is substantially similar, the imbalance in the stimulation delivered to the first and second lateral sides of patient 12 shown in FIG. 9C is achieved by delivering stimulation to the first lateral side of patient 12 for a longer duration of time than the second lateral side of patient 12. In particular, in the example shown in FIG. 9C, IMD 14 delivers pulse train 95A including four stimulation pulses 94 to the first lateral side of patient 12 during stimulation period 96A, and, after the end of stimulation period 96A, IMD 14 stops delivering stimulation to the first lateral side of patient and initiates delivery of second pulse train 95B to the second lateral side of patient 12 during second stimulation period 96B. Second pulse train 95B includes three stimulation pulses 94. As shown in FIG. 9C, during second stimulation period, IMD 14 As shown in FIG. 13C, at the beginning of second stimulation period, due to the configuration of pulse train 95B, IMD 14 does not immediately deliver a pulse 94, but waits a period of time (e.g., equal to the difference in time between the end of one pulse 124 and the beginning of another pulse 94 in pulse train 95B) prior to delivering a pulse 94. In other examples, IMD 14 immediately delivers a pulse 94 at the beginning of second stimulation period 95B.

In other examples, stimulation pulses delivered to the first lateral side of patient 12 may have a longer pulse width than the stimulation pulses delivered to the second lateral side of patient 12, or a different amplitude.

Stimulation periods 96A, 96B are substantially equal in the example shown in FIG. 9C, such that IMD 14 actively delivers stimulation to the first and second lateral sides of patient 12 for the same durations of time (though at different, non-overlapping times). However, during active delivery of stimulation to the first lateral side, IMD 14 delivers a pulse train 95A including more pulses compared to during active delivery of stimulation to the second lateral side. Pulse train 95A includes four pulses whereas pulse train 95B includes three pulses. The number of pulses in pulse trains 95A, 95B shown in FIG. 9C (as well as the other figures) is only one example. Pulse trains 95A, 95B may have any suitable size in other examples.

As shown in FIG. 9C, after IMD 14 delivers second pulse train 95B to the second lateral side of patient 12, IMD 14 may stop delivery of stimulation to the second lateral side and initiate delivery of pulse train 95A to the first lateral side of patient for a third stimulation period 96C. Stimulation period 96C may have the same duration as stimulation periods 96A, 96B in some examples. In addition, stimulation periods 96A, 96B, 96C do not overlap in the example of the first stimulation therapy shown in FIG. 9C.

In other examples, a combination of the regimes shown in FIGS. 9A-9C can be used to deliver an imbalanced bilateral stimulation therapy to patient 12 when IMD 14 delivers the first stimulation therapy to patient 12. Moreover, other types of stimulation regimes that include delivering stimulation to the first and second lateral sides of patient 12 at different times may be used.

FIGS. 10A-10F are schematic illustrations of stimulation signals delivered to the first and second lateral sides of patient 12 during the second electrical stimulation therapy. As shown in FIGS. 10A-10F, when stimulation generator 42 of IMD 14 delivers stimulation signals to the first and second lateral sides of patient 12 at different times, the stimulation signals at least partially overlap in time. The at least partial overlap can be, for example, a substantially completely overlap in time (FIGS. 10A and 10B) or partial overlap in time (FIGS. 10C-10F).

Figure 10A:
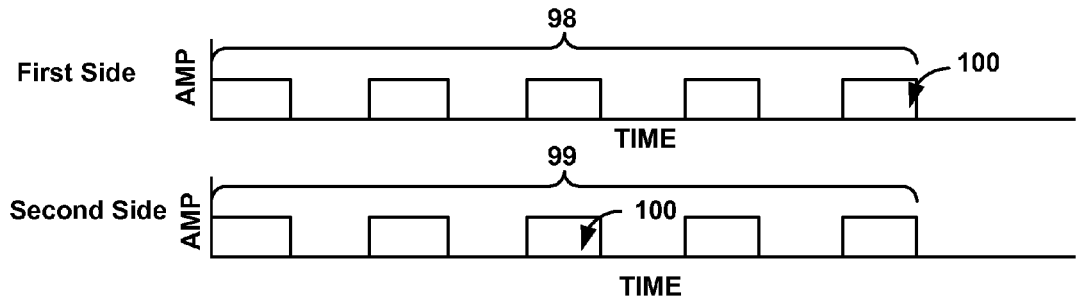
FIGS. 10A-10F are schematic illustrations of example stimulation signals delivered to the first and second sides of a patient during the second electrical stimulation therapy.

FIG. 10A illustrates a stimulation pulse regime in which IMD 14 delivers the second stimulation therapy to patient 12 by substantially simultaneously delivering stimulation pulses 100 to the first and second lateral sides of patient 12 (e.g., a time overlapping manner). Stimulation pulse train 98 including a plurality of stimulation pulses 100 is delivered to the first lateral side of patient 12 and pulse train 99 including a plurality of stimulation pulses 100 is delivered to the second lateral side of patient 12. In the example shown in FIG. 10A, the pulse trains 98, 99 delivered by IMD 14 to the first and second lateral sides of patient 12, respectively, completely overlap, such that IMD 14 delivers pulse trains 98, 99 to patient 12 during substantially overlapping stimulation periods. Rather than stopping therapy to one lateral side of patient 12, as described with respect to FIG. 9A, IMD 14 simultaneously delivers stimulation to both lateral sides of patient 12 in the example shown in FIG. 10A. In addition, in the example pulse regime shown in FIG. 10A, each stimulation pulse 100 has substantially the same pulse width and amplitude, such that the first and second lateral sides of patient 12 receive substantially similar intensities of stimulation. In this way, FIG. 10A illustrates a substantially balanced bilateral stimulation therapy in which the first and second lateral sides of patient 12 receive stimulation signals during substantially overlapping (e.g., completely overlapping) time slots.

Figure 10B:
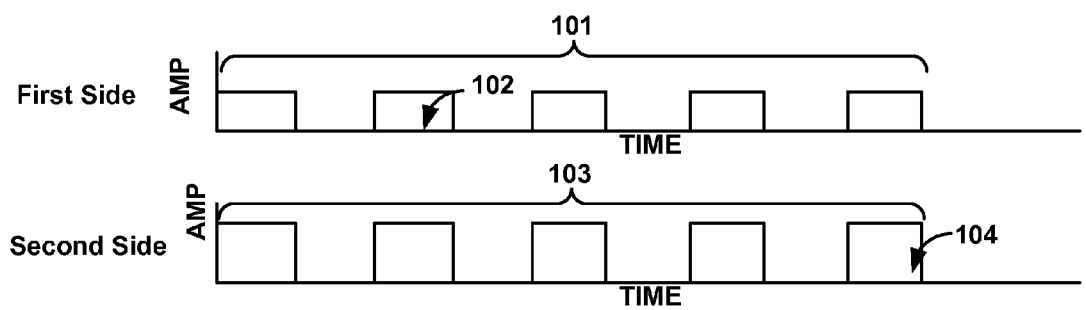

FIG. 10B illustrates an example of an imbalanced second stimulation therapy in which the first and second lateral sides of patient 12 receive different stimulation pulses 102, 104 at substantially the same time (e.g., during substantially overlapping stimulation periods). In particular, in the example shown in FIG. 10B, IMD 14 substantially simultaneously delivers a first pulse train 101 including a plurality of stimulation pulses 102 to a first lateral side of patient 12 and delivers a second pulse train 103 including a plurality of stimulation pulses 104 to a second lateral side of patient 12. Stimulation pulses 102, 104 have substantially similar pulse widths, but have different amplitudes. In this way, the first and second lateral sides of patient 12 receive different intensities of stimulation, such that the bilateral stimulation therapy shown in FIG. 10B is imbalanced. The pulses 102, 104 having substantially similar pulse widths substantially overlap in time, such that in the example shown in FIG. 10B, IMD 14 delivers stimulation to the first and second lateral sides of patient 12 in phase. In the example shown in FIG. 10B, the pulse trains 101, 103 delivered by IMD 14 to the first and second lateral sides of patient 12 substantially overlap.

Figure 10C:
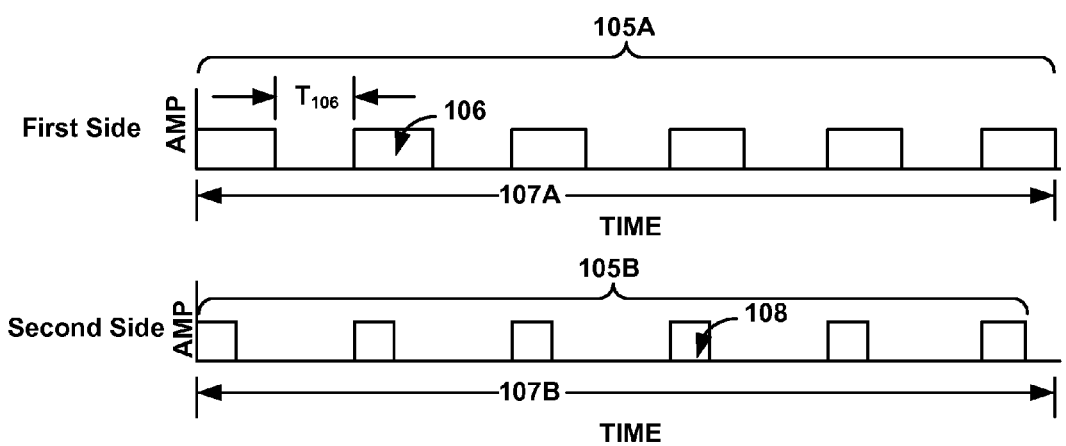

FIG. 10C illustrates another example of an imbalanced second stimulation therapy in which the pulse trains 105A, 105B delivered to the first and second lateral sides of patient 12 include different stimulation pulses 106, 108, respectively. Pulse trains 105A, 105B are delivered to patient 12 in an overlapping manner such that IMD 14 delivers substantially simultaneous bilateral stimulation to patient 12, and such that the pulses 106, 108 within the pulse trains 105A, 105B, respectively, partially overlap in time. Pulses 106, 108 have substantially similar amplitudes, but pulses 108 have approximately half of the pulse width as pulses 106 in the example shown in FIG. 10C. As a result, although IMD 14 may deliver pulse train 105A including stimulation pulses 106 to a first lateral side of patient 12 and deliver pulse train 105B including stimulation pulses 108 to a second lateral side of patient 12 in an overlapping manner (such that there is substantially simultaneous bilateral stimulation), the stimulation pulses 106, 108 delivered to the first and second lateral sides of patient 12 only partially overlaps in time. Thus, substantially simultaneous bilateral stimulation may be delivered to patient 12 despite a mismatch in time of stimulation pulses 106, 108.

In addition, in the example shown in FIG. 10C, IMD 14 delivers pulse train 105A to a first lateral side of patient 12 during first stimulation period 107A and delivers pulse train 105B to a second lateral side of patient 12 during second stimulation period 107B, where second stimulation period 107B is shorter than first stimulation period 107A. However, stimulation periods 107A, 107B partially overlap, such that IMD 14 delivers substantially simultaneous bilateral stimulation to patient 12 during at least the overlapping portions of stimulation periods 107A, 107B. After stimulation period 107A, IMD 14 stops delivery of stimulation therapy to the first lateral side of patient 12. In addition, after stimulation period 107B, IMD 14 stops delivery of the stimulation therapy to the second lateral side of patient 12. The example stimulation period 107A, 107B durations and pulse train 105A, 105B lengths shown in FIG. 10C are only one example. In other examples, stimulation periods 107A, 107B may have any suitable duration and pulse trains 105A, 105B may have any suitable lengths (e.g., any suitable number of pulses).

In some examples, pulses 106 may each have a pulse width of about 100 µs and pulses 108 may each have a pulse width of about 50 µs, and the time between subsequently delivered pulses 106 ($T_{106}$) may be about 50 µs to about 100 µs. Other examples of substantially simultaneous stimulation with mismatching pulses may also be used in accordance with the techniques herein. For example, although pulses 108 have approximately half the pulse width of pulses 106 in the example shown in FIG. 10C, in other examples, pulses 106, 108 may have any percentage of the width as each other, as long as IMD 14 delivers pulses 106, 108 to patient 12 such that they at least partially overlap in time.

Figure 10D:
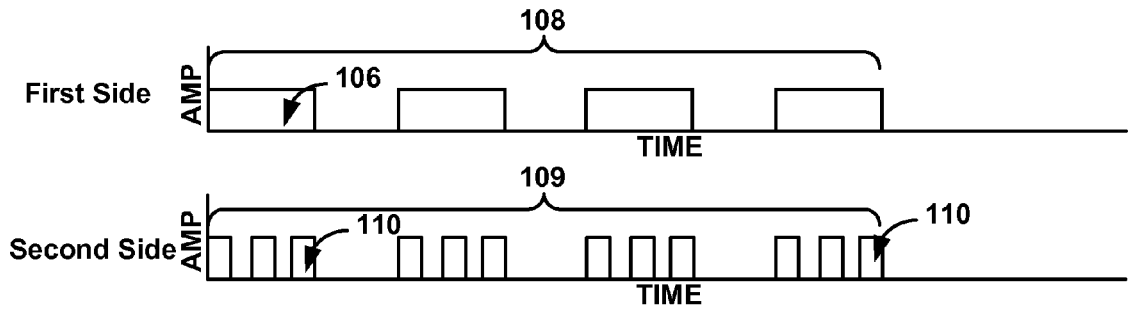

FIG. 10D illustrates another example of an imbalanced second stimulation therapy in which the first and second lateral sides of patient 12 receive different stimulation pulses 106, 110, where each pulse 106 partially overlaps in time with each pulse 110. In the example shown in FIG. 10D, IMD 14 delivers first pulse 108 train including pulses 106 to a first lateral side of patient 12 and second pulse train 109 including pulses 110 to a second lateral side of patient, where first and second pulse trains 108, 109 substantially overlap in time, such that IMD 14 delivers substantially simultaneous bilateral stimulation to patient 12. Pulse train 109 includes a plurality of bursts of pulses 110 separated in time. Pulses 110 have approximately 25% of the pulse width as each of the pulses 106 in the example shown in FIG. 10D, such that although IMD 14 may substantially simultaneously deliver pulse train 108 including stimulation pulses 106 to a first lateral side of patient 12 and deliver pulse train 109 including stimulation pulses 110 to a second lateral side of patient 12, the stimulation pulses delivered to the first and second lateral sides of patient 12 only partially overlaps in time. In the example shown in FIG. 10D, the stimulation period during which IMD 14 delivers pulse train 108 to the first lateral side of patient 12 is the same as the stimulation period during which IMD 14 delivers pulse train 110 to the second lateral side of patient 12.

Figure 10E:
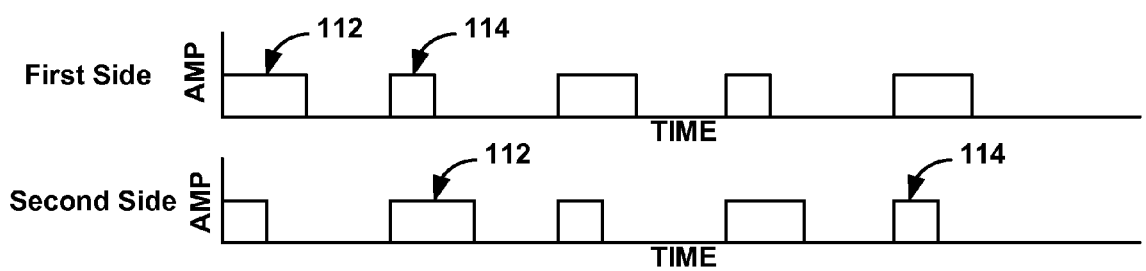

FIG. 10E illustrates another example of an imbalanced second stimulation therapy in which IMD 14 delivers identical pulse trains including stimulation pulses 112, 114 to the first and second lateral sides, respectively, of patient 12 such that the pulse trains are out-of-phase. As a result, pulses 112, 114 are delivered to the lateral sides of patient 12 at different times. In particular, IMD 14 delivers the pulse train to a first lateral side of patient 12 and to the second lateral side of patient 12 such that when IMD 14 delivers stimulation pulse 112 to the first lateral side of patient 12, IMD 14 delivers stimulation pulse 114 to the second lateral side of patient 12, such that stimulation pulses 112, 114 at least partially overlap in time. In addition, when IMD 14 delivers stimulation pulse 114 to the first lateral side of patient 12, IMD 14 delivers stimulation pulse 112 to the second lateral side of patient 12, such that stimulation pulses 112, 114 at least partially overlap in time. Because the pulse trains overlap, patient 12 receives substantially simultaneous bilateral stimulation that is imbalanced.

Figure 10F:
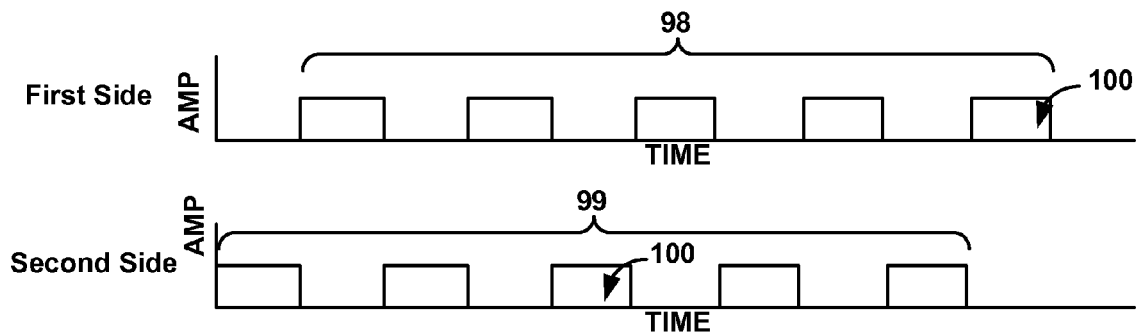

FIG. 10F illustrates an example of balanced second stimulation therapy in which IMD 14 delivers identical pulse trains 98, 99 including stimulation pulses 100 to patient 12 out of phase, such that pulses 100 are delivered to patient 12 at different times. Pulse trains 98, 99 shown in FIG. 10F are the same as the pulse trains shown in FIG. 10A. In FIG. 10A, IMD 14 delivers pulse trains 98, 99 to the respective lateral sides of patient 12 such that pulses 100 are in phase and completely overlap. In contrast, in FIG. 10F, IMD 14 delivers pulse trains 98, 99 such that pulses 100 are out of phase and do not overlap. As a result, there is a pulse mismatch between pulses 100 of the pulse train delivered to the first lateral side of patient 12 and pulses 100 of the pulse train delivered to the second lateral side of patient 12. As discussed in further detail below with respect to FIGS. 15A and 15B, experimental results indicate that, in some cases, a substantially equal efficacy may be achieved by the stimulation regime shown in FIG. 10A (pulse match) and the stimulation regime shown in FIG. 10F (pulse mismatch).

IMD 14 may deliver pulse trains 98, 99 such that pulses 100 are out of phase using any suitable technique. In the example shown in FIG. 10F, IMD 14 starts the delivery of pulse train 98 to the first lateral side of patient 12 after the start of delivery of pulse train 99 to patient 12. The delay may be, for example, equal to the pulse width of a pulse 100 of pulse train 98. In other examples, IMD 14 may initiate delivery of pulse trains 98, 99 to patient 12 at the same time, and pulse train 98 may be configured such that no pulse 100 is immediately delivered upon the beginning of the stimulation period in which IMD 14 actively delivers stimulation to the first lateral side of patient 12, and pulse train 99 may be configured such that a pulse 100 is immediately delivered upon the beginning of the stimulation period in which IMD 14 actively delivers stimulation to the second lateral side of patient 12.

In other examples, a combination of the regimes shown in FIGS. 10B-10F can be used to deliver an imbalanced bilateral stimulation therapy to patient 12 when IMD 14 delivers the second stimulation therapy to patient 12. Moreover, other types of stimulation regimes that include delivering stimulation to the first and second lateral sides of patient 12 substantially simultaneously may be used.

FIGS. 11-15B are graphs that illustrate a change in bladder contraction frequency in response to electrical stimulation. The data illustrated in FIGS. 11-15B was obtained from a plurality of tests performed on anesthetized female laboratory rats weighing approximately 200 grams to about 300 grams. During the tests, the body temperatures of the subjects were maintained at approximately 37° C. and bladder contractions of one or more test subjects were observed during an approximately 40 minute period (e.g., −15 minutes to 25 minutes shown along the time axis in FIGS. 11-13). During the observation period, there was an approximately 15 minute control period, followed by a 10 minute stimulation period (which is indicated by stimulation period 116 in each of FIGS. 11-13, 14A, and 15A), and a 20 minute post-stimulation period. During the stimulation period, electrical stimulation was delivered to an L6 spinal nerve of each subject for about ten minutes. An exposed portion of wire electrode (a Teflon-coated, 40-gauge, stainless steel wire available from Cooner Wire, Inc. of Chatsworth, Calif.) was placed under the L6 spinal nerve unilaterally or bilaterally. The electrode was connected to a S88 pulse stimulator (available from Grass Technologies of West Warwick, Rhode Island) through a stimulation isolation unit, which generated biphasic stimulation pulses having pulse widths of about 0.1 ms and a frequency of about 10 Hz. A needle electrode served as the ground.

A cannula was placed into the bladder of each subject via the urethra and the urethra was ligated to ensure an isovolumetric bladder. To induce bladder rhythmic contractions in the subject, saline was infused into the bladder of the subject via the cannula at a rate of about 50 microliters (μL) per minute to induce a micturition reflex, which was defined in these experiments to be a bladder contraction of a magnitude greater than about 10 millimeters of mercury (mmHg). Thereafter, the infusion rate was reduced to about 10 μL a minute and continued until about three to about five consecutive contractions were established. After that time, the bladder rhythmic contractions continued until the saline infusion was terminated. The control period for determining the bladder contraction frequency control value was about 15 minutes. The bladder contractions were recorded using a pressure transducer connected to the cannula placed in the bladder of the subject. The pressure transducer input into an ADInstrument data acquisition system, which is commercially available from ADInstruments of Colorado Springs, Colo.

For each test run (i.e., each 40 minute observation), a frequency of bladder contractions was determined at approximately 5 minute intervals. The determined frequencies of bladder contractions were then normalized (i.e., divided by) by a frequency of bladder contractions of the test subject at the time indicated by "−5 minutes" in the figures. The normalized bladder contraction frequencies are graphed in FIGS. 11-13, 14A, and 15A. The graphs illustrated in FIGS. 11-13, 14A, and 15A each plots frequency versus time. Frequency (normalized %) indicates a frequency of bladder contraction relative to the frequency of bladder contractions of the test subject at time −5 minutes. Frequency (normalized %) ranges from 0% to 120%. The results of the experiments shown in FIGS. 11-15B were analyzed with GraphPad Prism 4 software (available from GraphPad Software, Inc. of San Diego, Calif.).

For each of the subjects in the experiments conducted to generate the data shown in FIGS. 11-15B, the threshold intensity level was determined by determining the lowest current level at which the first visually discernable muscle contraction was evoked.

Figure 11:
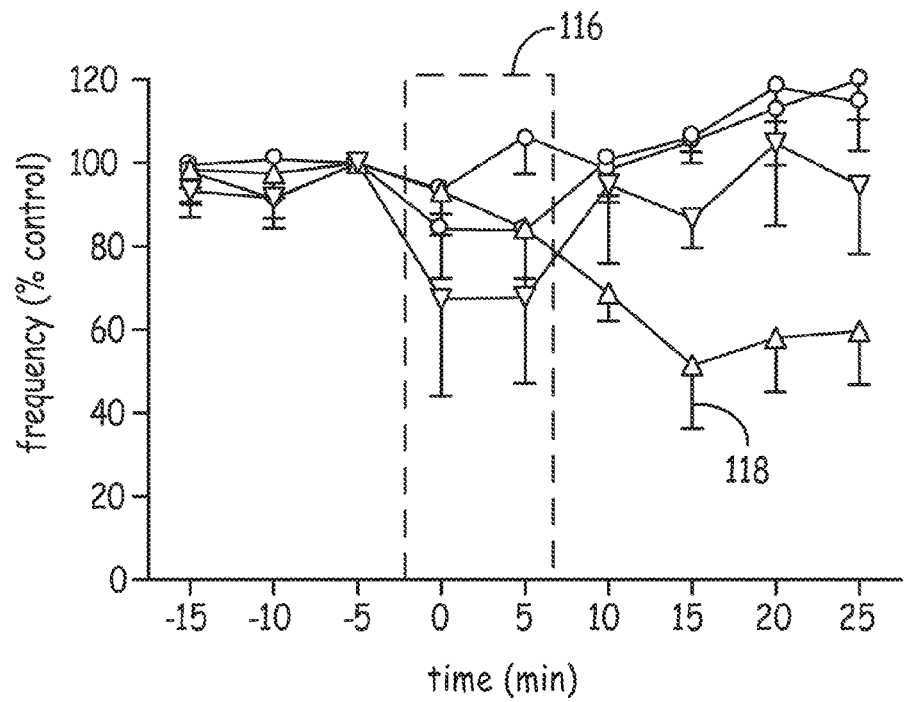
FIGS. 11-13 are graphs that illustrate examples of changes in bladder contraction frequency of test subjects in response to unilateral stimulation, bilateral stimulation delivered at different times to two lateral sides of the subjects, and substantially simultaneous bilateral stimulation.
Figure 12:
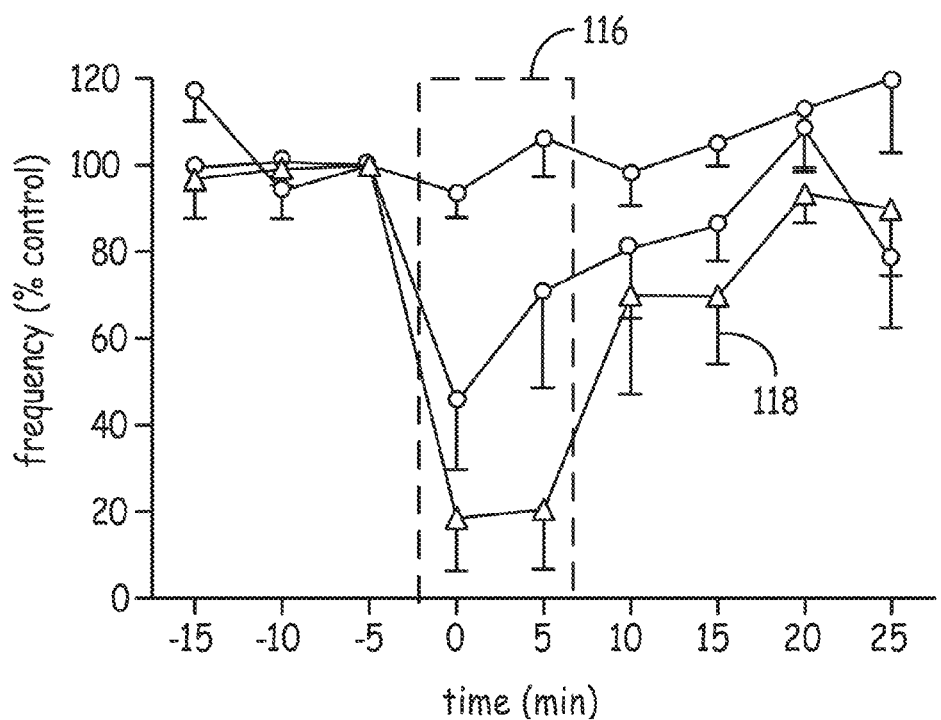
Figure 13:
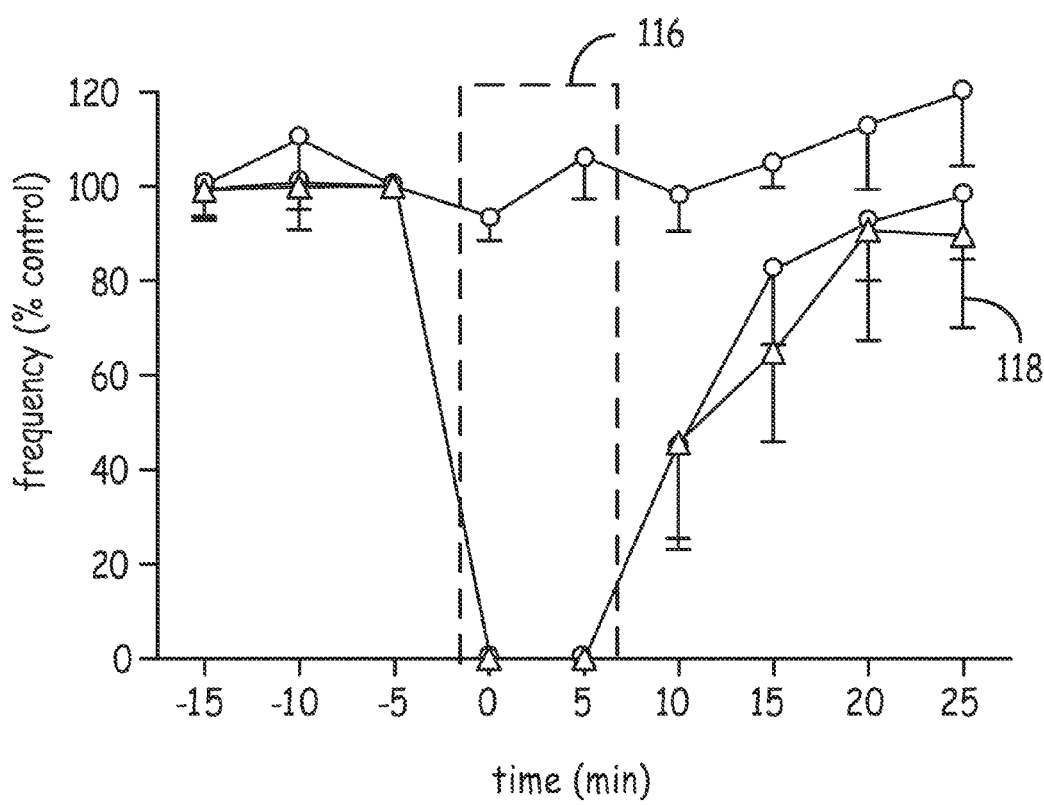

The type of stimulation delivered to the test subject is indicated by the shape of the data point illustrated in FIGS. 11-13. Each of the data points (i.e., open circles, solid circles, triangular data points that include a single vertex at the top, and inverted triangular data points that include two vertices at the top) shown in FIGS. 11-13 include an amount of variation. The variation bars, e.g., illustrated in one example as variation bar 118 in FIG. 11, are included to show variations among measurements.

The open circle data points in FIGS. 11-13 indicate measurement of bladder contraction frequency in subjects that did not receive electrical stimulation (the control group). Accordingly, the open circle data points represent a bladder contraction frequency at approximately 100% normalized frequency. The solid circle data points in FIGS. 11-13 indicate measurement of bladder contraction frequency in subjects that received unilateral electrical stimulation, which consisted of electrical stimulation at a target tissue site proximate a pelvic floor nerve on only one lateral side of the subject's body. The unilateral stimulation was delivered at a threshold intensity level, which varied by subject and tissue site. The mean threshold intensity level for the subjects used for the unilateral stimulation therapy was characterized by a current amplitude of about 0.2 mA (with a variation of about 0.07 mA), a frequency of about 10 Hz, and a pulse width of about 100 µs.

The triangular data points that include a single vertex at the top (e.g., pointing in a direction furthest from the x-axis) indicate the measurement of bladder contraction frequency in subjects that received the second stimulation therapy, whereby stimulation was delivered substantially simultaneously to one lateral side of the subject at a threshold intensity level, which varied by subject, and to the other lateral side of the subject at a stimulation intensity below the threshold intensity level. The mean threshold intensity level for the subjects used for the second stimulation therapy was characterized by a current amplitude of about 0.10 mA (with a variation of about 0.02 mA), a frequency of about 10 Hz, and a pulse width of about 100 µs.

The inverted triangle data points (shown in FIG. 11) that include two vertices at the top indicate the measurement of bladder contraction frequency in subjects that received the first stimulation therapy, whereby stimulation was delivered to the two lateral sides of the subject at alternating times. The stimulation was delivered at a threshold intensity level, which varied by subject. The mean threshold intensity level for the subjects used for the first stimulation therapy was characterized by a current amplitude of about 0.10 mA (with a variation of about 0 mA a frequency of about 10 Hz, and a pulse width of about 100 µs.

In FIG. 11, the solid circle data points indicate a bladder contraction frequency of the subjects decreased during stimulation period 116 in response to the delivery of the unilateral stimulation, but then gradually increased in the time period following stimulation period 116, when no stimulation was being delivered to the subjects (e.g., after about 5 minutes in the time course shown in FIG. 11). Thus, it was observed that the unilateral stimulation therapy reduced bladder contraction frequency as the stimulation was being delivered to the subject, but upon cessation of the unilateral stimulation therapy, the bladder contraction frequency began to increase and recovers toward the control frequency, i.e., toward the bladder contraction frequency observed when no stimulation therapy is delivered. The solid circle data points indicate that reduction in bladder contraction frequency is not pronounced, but may be present, during stimulation period 116. Accordingly, the test results indicate that unilateral stimulation therapy may reduce bladder contraction frequency by a moderate amount while the stimulation is being delivered to the subject.

In FIG. 11, the trajectory of the inverted triangle data points (with the two vertices at the top) over time indicates that the bladder contraction frequency of the subjects decreased in response to the delivery of the first electrical stimulation therapy, which in the tests included delivery of stimulation to the lateral sides of the subject in an alternating fashion. The trajectory of the inverted triangle data points also indicate that the bladder contraction frequency of the subjects increased towards the control bladder contraction frequency in the post-stimulation period immediately following stimulation period 116. In particular, the bladder contraction frequency decreased from about 100% of the control to about 60% to about 70% of the control during stimulation period 116, and increased to between then to between about 80% to about 100% about 5 minutes after stimulation period 116. The reduction in bladder contraction frequency observed during stimulation period 116 in response to the delivery of the first stimulation therapy is of a magnitude that may provide efficacious bladder dysfunction therapy to patient 12.

In FIG. 11, the trajectory of the triangular data points with the single vertex at the top over time indicates that the bladder contraction frequency of the subjects decreased in response to the delivery of the second electrical stimulation therapy, which included substantially simultaneous imbalanced bilateral stimulation, even during the time period following stimulation period 116. In particular, the bladder contraction frequency decreased from about 100% of the control to about 80% during stimulation period 116, and then to between about 60% to about 80% about 5 minutes after stimulation period 116, and then to about 40% to about 60% about 10 minutes after stimulation period 116. About 10 minutes after the cessation of the second stimulation therapy, the bladder contraction frequency of the subjects began to gradually increase towards the control frequency, but remained significantly below the control frequency even 20 minutes after stimulation period 116. The reduction in bladder contraction frequency observed during both stimulation period 116 and the post stimulation period in response to the delivery of the first bilateral stimulation therapy is of a magnitude that may provide efficacious bladder dysfunction therapy to patient 12.

The test results shown in FIG. 11 indicate that the delivery of bilateral stimulation therapy, whether delivered to the two lateral sides of the subject substantially simultaneously or at different times, elicited a stronger inhibitory physiological response from the subjects, and, in particular, a stronger inhibition of bladder contractions, than the unilateral stimulation (associated with the solid circle data points) alone.

The test results shown in FIG. 11 also indicate that the delivery of the second stimulation therapy that included substantially simultaneous bilateral stimulation therapy elicited a delayed inhibition of bladder contractions relative to the first stimulation therapy. Moreover, the inhibition of bladder contractions appeared to be more pronounced with the substantially simultaneous bilateral stimulation therapy compared to the alternating bilateral stimulation therapy, e.g., based on the comparison of the lowest frequency indicated by the data points with a single vertex at the top to the lowest frequency indicated by the inverted triangular data points (with two vertices at the top).

The test results shown in FIG. 12 indicate that bilateral stimulation generated a stronger inhibitory physiological effect in the subjects compared to the unilateral stimulation at a stimulation amplitude of about 0.6 mA and a frequency of about 0.5 Hz and delivered for about 10 minutes. While the test results in FIG. 12 only illustrate the test results from the second stimulation therapy (including substantially simultaneous bilateral stimulation), the test results shown in FIG. 11 indicate that bilateral stimulation that includes delivery of stimulation to the lateral sides of the subject in an alternating fashion, also elicited a stronger inhibitory physiological effect in the subjects compared to the unilateral stimulation.

In FIG. 12, the unilateral stimulation elicited a bladder contraction frequency that was about 40% to about 50% of the control bladder contraction frequency at the time the stimulation was delivered (at about the beginning of stimulation period 116), but during stimulation period 116, the bladder contraction frequency began to increase from that bladder contraction frequency towards the control. At cessation of the unilateral stimulation therapy, the bladder contraction frequency increased to about 60% to about 80% of the control, and about 15 minutes after the unilateral stimulation was delivered to patient 12 (i.e., at about the 20 minute mark in FIG. 12), the bladder contraction frequency of the subjects increased to greater than or equal to the control frequency.

In contrast, in the test results shown in FIG. 12, the bilateral stimulation elicited a elicited a bladder contraction frequency that was about 20% of the control bladder contraction frequency during stimulation period 116. In addition, while the bladder contraction frequency increased in the post-stimulation period, the bladder contraction frequency remained below the control, as well as below the bladder contraction frequency in the post-stimulation period elicited by the unilateral stimulation.

In the tests conducted to generate the test results shown in FIG. 13, the unilateral electrical stimulation (delivered at a stimulation amplitude of about 0.6 mA and a frequency of about 0.5 Hz and delivered for about 10 minutes) and bilateral electrical stimulation elicited substantially similar results during stimulation period 116.

Based on at least the test results shown FIGS. 11-13, it is believed that the unilateral stimulation therapy, substantially simultaneous bilateral stimulation therapy, and the bilateral stimulation therapy that included delivery of stimulation to the lateral sides of the subject at different times can each generate different inhibitory physiological responses from a patient. The test results further indicate that the substantially simultaneous bilateral stimulation therapy may elicit a greater decrease in bladder contraction frequency compared to the unilateral stimulation therapy and the alternating bilateral stimulation therapy. Moreover, the test results shown in FIG. 11 indicate that substantially simultaneous bilateral stimulation therapy generated a stronger inhibitory physiological response from the subjects compared to the alternating bilateral stimulation therapy, such that the substantially simultaneous bilateral stimulation therapy may be useful as a supplementary therapy (in combination with the alternating bilateral stimulation therapy) that is delivered to patient 12 when a stronger therapeutic effect is desirable.

Figure 14A:
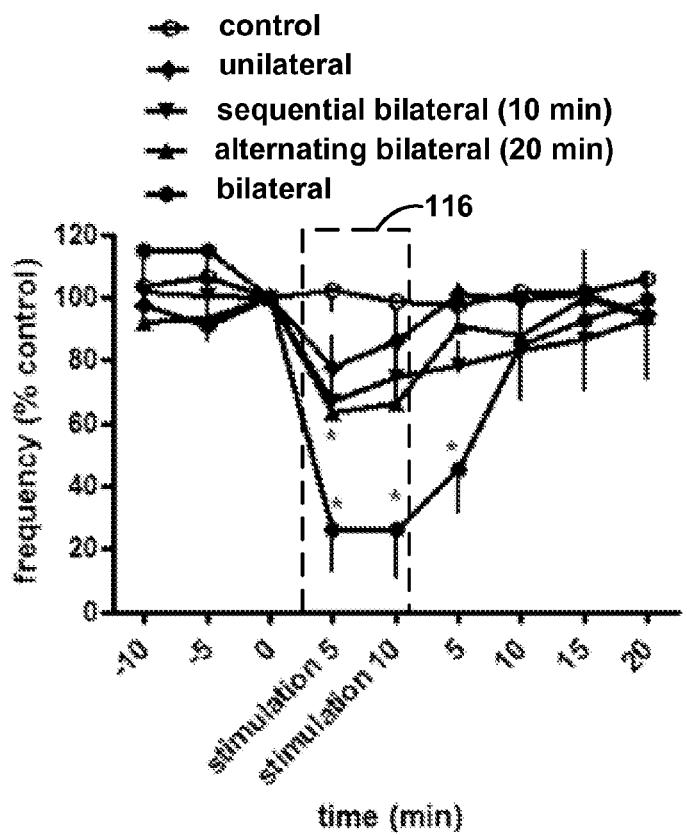
FIGS. 14A and 14B are additional graphs that illustrate examples of changes in bladder contraction frequency of test subjects in response to unilateral stimulation, bilateral stimulation delivered at different times to two lateral sides of the subjects, and substantially simultaneous bilateral stimulation.
Figure 14B:
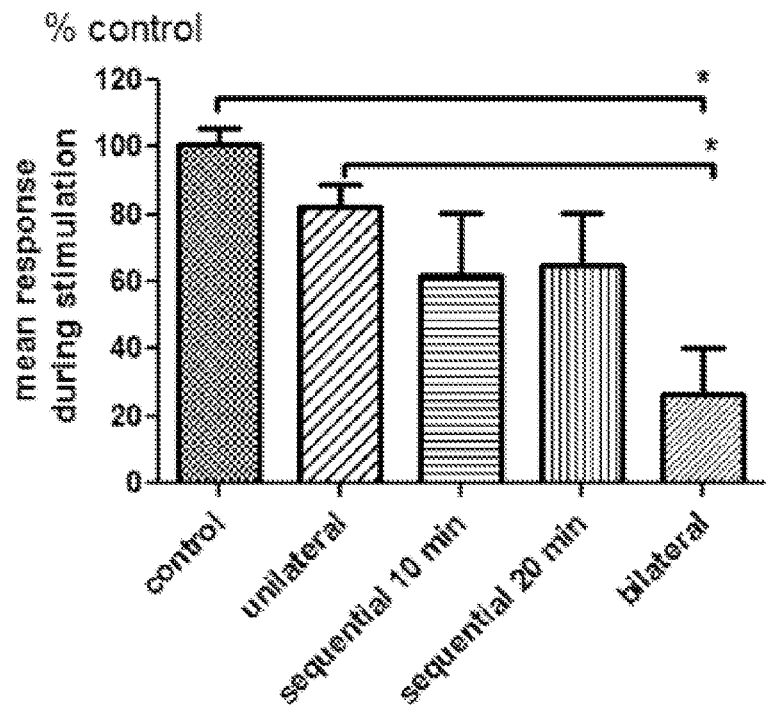

FIGS. 14A and 14B are graphs that illustrate example time courses of responses of bladder contractions to unilateral stimulation, alternating bilateral stimulation for approximately 10 minutes, alternating bilateral stimulation for approximately 20 minutes, and substantially simultaneous bilateral stimulation. As with FIGS. 11-13, the data illustrated in FIGS. 14A and 14B was obtained from a plurality of tests performed on laboratory rats. During the tests, bladder contractions of one or more test subjects were observed during an approximately 40 minute period (i.e., a pre-stimulation period, a 10 minute stimulation period 116, and then a post-stimulation period, which are shown along the time axis in FIG. 14A). During this observation period, electrical stimulation was delivered to an L6 spinal nerve of each subject for about ten minutes, which is indicated by stimulation period 116 in FIG. 14A. For each test run (i.e., each 40 minute observation), a frequency of bladder contractions was determined at approximately 5 minute intervals. The determined frequencies of bladder contractions were then normalized (i.e., divided by) by a frequency of bladder contractions of the test subject at the time indicated by "−5 minutes" in the figures. The normalized bladder contraction frequencies are graphed in FIG. 14A. The graphs illustrated in FIG. 14A each plots frequency versus time. Frequency (normalized %) indicates a frequency of bladder contraction relative to the frequency of bladder contractions of the test subject at time −5 minutes. Frequency (normalized %) ranges from 0% to 120%.

The type of stimulation delivered to the test subject is indicated by the shape of the data point illustrated in FIG. 14A. As with FIGS. 11-13, each of the data points shown in FIG. 14A include an amount of variation, which is illustrated by a respective variation bar. The open circle data points in FIG. 14A indicate the mean normalized bladder contraction frequencies of 21 subjects that did not receive electrical stimulation (the control group), such that the open circle data points represent a bladder contraction frequency at approximately 100% normalized frequency. The diamond shaped data points in FIG. 14A indicate the mean normalized bladder contraction frequencies of 15 subjects that received unilateral electrical stimulation, which consisted of electrical stimulation at a target tissue site proximate a L6 spinal on only one lateral side of the subject's body. The unilateral stimulation was delivered to the one side of each subject at a threshold intensity level for approximately ten minutes, where the threshold intensity level varied by subject and tissue site. The mean threshold intensity level for the subjects used for the unilateral stimulation therapy was characterized by a current amplitude of about 0.15 mA (with a variation of about 0.03 mA), a frequency of about 10 Hz, and a pulse width of about 100 μs.

The inverted triangular data points, which include two vertices at the top, indicate the mean normalized bladder contraction frequencies of 7 subjects that received the first stimulation therapy for approximately 10 minutes, whereby stimulation was delivered in an alternating manner to the two lateral sides of the subject at the subject at a threshold intensity level, which varied by subject. For each subject, the stimulation was first delivered to a first lateral side of the subject for approximately 5 minutes, followed by stimulation delivery to the second lateral side of the subject for approximately 5 minutes. Stimulation was stopped after stimulation delivery to the second lateral side. The mean threshold intensity level for the subjects used for the first stimulation therapy was characterized by about 0.14 mA (with a variation of about 0.04 mA), a frequency of about 10 Hz, and a pulse width of about 100 μs.

The triangular data points that include a single vertex at the top (e.g., pointing in a direction furthest from the x-axis) indicate the mean normalized bladder contraction frequencies of 11 subjects that received the first stimulation therapy for approximately 20 minutes, whereby, for each subject, stimulation was delivered in an alternating matter to the lateral sides of the subject at a threshold intensity level, which varied by subject. The stimulation was first delivered to a first lateral side of the subject for approximately 5 minutes, followed by stimulation delivery to the second lateral side of the subject for approximately 5 minutes, followed by stimulation delivery to the first lateral side of the subject for approximately 5 minutes, followed by stimulation delivery to the second lateral side of the subject for approximately 5 minutes. Stimulation was stopped after the second course of stimulation delivery to the second lateral side. The mean threshold intensity level for the subjects used for the second stimulation therapy was characterized by a current amplitude of about 0.04 mA (with a variation of about 0.01 mA), a frequency of about 10 Hz, and a pulse width of about 100 μs.

In order to show the results of the alternating bilateral stimulation therapy for approximately 20 minutes and compare it to the results of the unilateral stimulation for approximately 10 minutes and the alternating bilateral stimulation for approximately 10 minutes, the approximately 20 minute stimulation period was scaled to fit into the 10 minute stimulation period 116 shown in FIG. 14A. As a result, the triangular data point shown at time "stimulation 5" in FIG. 14A corresponds to the mean bladder contraction frequency value after stimulation was delivered to the first lateral side of the subject for approximately 5 minutes and subsequently delivered to the second lateral side of the subject for approximately 5 minutes, and the triangular data point shown at time "stimulation 10" in FIG. 14A corresponds to the mean bladder contraction frequency value after stimulation was subsequently delivered to the first lateral side of the subject for approximately 5 minutes and then to the second lateral side of the subject for approximately 5 minutes.

In FIG. 14A, the solid circle data points indicate the mean normalized bladder contraction frequencies of 10 subjects that received the second stimulation therapy, which was imbalanced substantially simultaneous bilateral stimulation therapy. In these examples, for each subject, stimulation was delivered substantially simultaneously to a first lateral side of the subject at a threshold intensity level, which varied by subject, and to the other lateral side of the subject at a stimulation intensity below the threshold intensity level. The mean threshold intensity level for the subjects used for the second stimulation therapy was characterized by a current amplitude of about 0.06 mA (with a variation of about 0.03 mA), a frequency of about 10 Hz, and a pulse width of about 100 μs.

The data shown in FIG. 14A indicates that a bladder contraction frequency of the subjects decreased during the stimulation period 116 in response to the unilateral stimulation (diamond data points), alternating bilateral stimulation for approximately 10 minutes (inverted triangular data points), alternating bilateral stimulation for approximately 20 minutes (triangular data points), and imbalanced substantially simultaneous bilateral stimulation (solid circle data points). However, the decrease in bladder contraction frequency during stimulation period 116 was most pronounced for the substantially simultaneous bilateral stimulation compared to the unilateral stimulation, alternating bilateral stimulation for approximately 10 minutes, or alternating bilateral stimulation for approximately 20 minutes. The data further indicates that the bladder contraction frequency of the subjects decreased more during stimulation period 116 in response to the alternating bilateral stimulation for approximately 20 minutes compared to the unilateral or alternating bilateral stimulation for approximately 10 minutes, and that the bladder contraction frequency of the subjects decreased more during stimulation period 116 in response to the alternating bilateral stimulation for approximately 10 minutes compared to the unilateral stimulation.

In addition, the data shown in FIG. 14A indicates that the bladder contraction frequency of the subjects remained relatively low compared to the control (open circle data points) for the unilateral stimulation (diamond data points), alternating bilateral stimulation thr approximately 10 minutes (inverted triangular data points), and alternating bilateral stimulation for approximately 20 minutes (triangular data points) both during stimulation period 116 and after stimulation period 116. However, with the unilateral, alternating bilateral stimulation for approximately 10 minutes, alternating bilateral stimulation for approximately 20 minutes, and substantially simultaneous bilateral stimulation, the bladder contraction frequency of the subjects increased toward the bladder contraction frequency observed when no stimulation therapy was delivered in the time period immediately following stimulation period 116. As shown in FIG. 14A, the alternating bilateral stimulation for approximately 20 minutes appeared to result in a greater increase in bladder contraction frequency during the time period immediately following stimulation period 116 compared to the alternating bilateral stimulation for approximately 10 minutes. This may indicate, for example, the alternating bilateral stimulation for approximately 10 minutes may have longer lasting affects compared to the alternating bilateral stimulation for approximately 20 minutes.

In FIG. 14A, the trajectory of the diamond data points over time indicates that the bladder contraction frequency of the subjects decreased in response to the delivery of the unilateral stimulation. The trajectory of the diamond data points indicate that the bladder contraction frequency of the subjects decreased from about 100% of the control to about 75% to about 80% of the control during stimulation period 116, and then increased to between about 100% of the control about 5 minutes immediately after stimulation period 116. During stimulation period 116, the mean reduction in bladder contraction frequency in response to the unilateral stimulation was about 82.04%±7% (p>0.05) of the control. The control was about 98.52%±5%.

The trajectory of the inverted triangular data points, which correspond to the alternating bilateral stimulation therapy for approximately 10 minutes, over time indicate that, in response to the alternating bilateral stimulation, the bladder contraction frequency of the subjects decreased from about 100% of the control to about 65% to about 70% of the control during stimulation period 116, and, during stimulation period 116, began increasing, such that after about 5 minutes after about 5 minutes of stimulation (5 minutes into stimulation period 116), the bladder contraction frequency of the subjects between about 75% to about 80% of the control. During stimulation period 116, the mean reduction in bladder contraction frequency in response to the alternating bilateral stimulation therapy for approximately 10 minutes was about 61.85%±18% (p>0.05) of the control. The reduction in bladder contraction frequency observed during stimulation period 116 in response to the delivery of the alternating bilateral stimulation for approximately 10 minutes is of a magnitude that may provide efficacious bladder dysfunction therapy to patient 12.

Also shown in FIG. 14A is a trajectory of the triangular data points, which correspond to the alternating bilateral stimulation therapy for approximately 20 minutes. The trajectory of the triangular data points over time indicate that, in response to the alternating bilateral stimulation for approximately 20 minutes, the bladder contraction frequency of the subjects decreased from about 100% of the control to about 60% to about 65% of the control during stimulation period 116, and increased to between then to between about 90% to about 100% of the control about 5 minutes after stimulation period 116. During stimulation period 116, the mean reduction in bladder contraction frequency in response to the alternating bilateral stimulation therapy for approximately 20 minutes was about 64.90%±16% (p>0.05) of the control. The reduction in bladder contraction frequency observed during stimulation period 116 in response to the delivery of the alternating bilateral stimulation for approximately 20 minutes is of a magnitude that may provide efficacious bladder dysfunction therapy to patient 12.

Despite the increase in bladder contraction frequency after stimulation period 116 for both durations of the alternating bilateral stimulation therapies, the experimental results shown in FIG. 14A indicate that both alternating bilateral stimulation for approximately 10 minutes and alternating bilateral stimulation for approximately 20 minutes may reduce bladder contraction frequency by a moderate amount while the stimulation is being delivered to the subject, where the moderate amount may still be useful for managing the bladder dysfunction of the patient.

In FIG. 14A, trajectory of the solid circle data points over time indicates that the bladder indicates that the bladder contraction frequency of the subjects decreased in response to the delivery of the second electrical stimulation therapy, which was substantially simultaneous bilateral stimulation therapy in the experiment described with respect to FIG. 14A. The trajectory of the solid circle points indicate that the bladder contraction frequency of the subjects decreased from about 100% of the control to about 25% to about 30% of the control during stimulation period 116, and increased to between then to between about 40% to about 45% of the control about 5 minutes after stimulation period 116. During stimulation period 116, the mean reduction in bladder contraction frequency in response to the substantially simultaneous bilateral stimulation therapy for approximately 10 minutes was about 26.3%±14% (p<0.05) of the control. The reduction in bladder contraction frequency observed during stimulation period 116 in response to the delivery of the alternating bilateral stimulation for approximately 10 minutes and for a period of time (e.g., about 10-20 minutes) immediately after stimulation period 116 is of a magnitude that may provide efficacious bladder dysfunction therapy to patient 12.

The experimental results shown in FIG. 14A indicate that the delivery of bilateral stimulation therapy, whether delivered to the two lateral sides of the subject substantially simultaneously or at different times, elicited a stronger inhibitory physiological response from the subjects, and, in particular, a stronger inhibition of bladder contractions, than the unilateral stimulation (associated with the solid circle data points) alone. In addition, the experimental results shown in FIG. 14A indicate that the delivery of substantially simultaneous bilateral stimulation therapy elicited a stronger inhibitory physiological response from the subjects, and, in particular, a stronger inhibition of bladder contractions, during stimulation period 116 than the bilateral stimulation delivered to the lateral sides of the subject at different times.

FIG. 14B is a bar graph that illustrates the mean response of the subjects during stimulation period 116 for each of the types of stimulation described with respect to FIG. 14A, FIG. 14B further illustrates that the alternating bilateral stimulation for approximately 10 minutes and alternating bilateral stimulation therapy for approximately 20 minutes each elicited a relatively moderate reduction in bladder contraction frequency during stimulation period 116 compared to the substantially simultaneous bilateral stimulation. In particular, in response to the alternating bilateral stimulation for approximately 20 minutes, the mean response of the subjects during stimulation period 116 was a bladder contraction frequency was about 65% of the control and, in response to the alternating bilateral stimulation for approximately 10 minutes, the mean response of the subjects during stimulation period 116 was a bladder contraction frequency was about 61% of the control. The mean response of the subjects during stimulation period 116 to the second type of stimulation therapy, i.e., substantially simultaneous bilateral stimulation therapy in the experiments conducted to generate the data shown in FIG. 14B, was a bladder contraction frequency that was about 20% of the control.

Figure 15A:
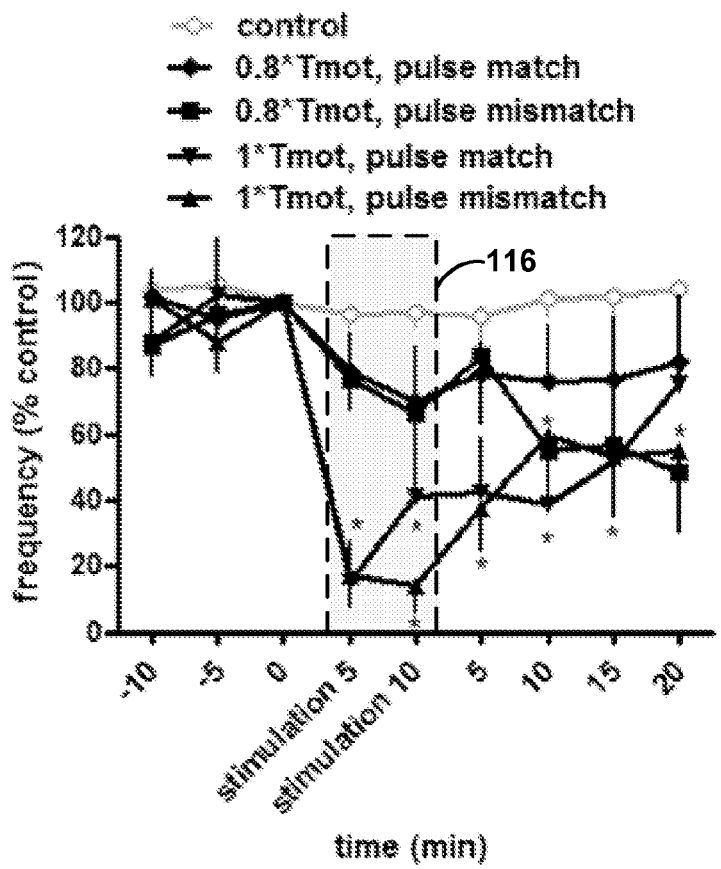
FIGS. 15A and 15B are graphs that illustrate the effect of pulse match and pulse mismatch on bladder contraction frequency during delivery of, substantially simultaneous bilateral stimulation.
Figure 15B:
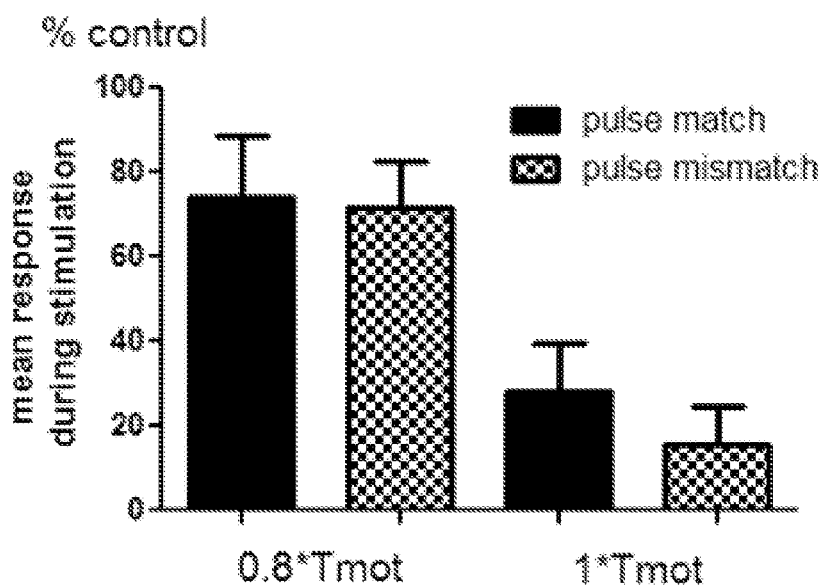

As discussed above, during substantially simultaneous bilateral stimulation therapy, the electrical stimulation signal trains delivered to the lateral sides of patient 12 overlap, such that there is an overlap in stimulation periods for the stimulation delivered to each lateral side of patient 12. Within each signal train, however, the stimulation signals may be delivered at different times or at the same time. For example, as discussed with respect to FIG. 10F, the pulses within the pulse trains may be mismatched such that pulses may not be delivered to the two lateral sides of patient 12 substantially simultaneously. FIGS. 15A and 15B are graphs that illustrate the affect of pulse match and pulse mismatch on bladder contraction frequency during delivery of substantially simultaneous bilateral stimulation.

As with FIGS. 11-14B, the data illustrated in FIGS. 15A and 15B was obtained from a plurality of tests performed on laboratory rats. During the tests, bladder contractions of one or more test subjects were observed during an approximately 40 minute period (i.e., a pre-stimulation period, a 10 minute stimulation period 116, and then a post-stimulation period, which are shown along the time axis in FIG. 15A). During this observation period, electrical stimulation was delivered to an L6 spinal nerve of each subject for about ten minutes, which is indicated by stimulation period 116 in FIG. 15A. For each test run (i.e., each 40 minute observation), a frequency of bladder contractions was determined at approximately 5 minute intervals. The normalized bladder contraction frequencies are graphed in FIG. 15A.

The type of stimulation delivered to the test subjects is indicated by the shape of the data point illustrated in FIG. 15A. As with FIGS. 11-13, each of the data points shown in FIG. 15A include an amount of variation, which is illustrated by a respective variation bar. The open circle data points in FIG. 15A indicate the mean normalized bladder contraction frequencies of 21 subjects that did not receive electrical stimulation (the control group), such that the open circle data points represent a bladder contraction frequency at approximately 100% normalized frequency. The diamond shaped data points in FIG. 15A indicate the mean normalized bladder contraction frequencies of 6 subjects that received substantially simultaneous bilateral stimulation at about 80% of the threshold intensity level (indicated as "0.8*Tmot" in FIGS. 15A and 15B) of the subject for approximately ten minutes, where the pulse trains were delivered to the two lateral sides of the subject such that the pulses of the pulse trains substantially matched in time (e.g., as shown in FIG. 10A). In this example, the electrical stimulator delivered the pulses to the lateral side of the patients with a delay of about 0.05 seconds. The threshold intensity level was a motor threshold and varied by subject and tissue site. The mean threshold intensity level for the subjects used for the substantially simultaneous bilateral stimulation at about 80% of the threshold intensity and with a pulse match was characterized by a current amplitude of about 0.17 mA (with a variation of about 0.01 mA), a frequency of about 10 Hz, and a pulse width of about 100 µs.

The square data points in FIG. 15A indicate the mean normalized bladder contraction frequencies of 6 subjects that received substantially simultaneous bilateral stimulation at about 0.8 percent of the threshold intensity level of the subject for approximately ten minutes, where the pulse trains were delivered to the two lateral sides of the subject such that the pulses of the pulse trains did not match in time (e.g., as shown in FIG. 10F). Again, the threshold intensity level varied by subject and tissue site. The mean threshold intensity level for the subjects used for the substantially simultaneous bilateral stimulation at about 80% of the threshold intensity and with a pulse mismatch was characterized by a current amplitude of about 0.18 mA (with a variation of about 0.02 mA), a frequency of about 10 Hz, and a pulse width of about 100 µs.

The inverted triangular data points, which include two vertices at the top, indicate the mean normalized bladder contraction frequencies of 5 subjects that received substantially simultaneous bilateral stimulation at about 100% of the threshold intensity level of the subject for approximately ten minutes, where the pulse trains were delivered to the two lateral sides of the subject such that the pulses of the pulse trains matched in time. The mean threshold intensity level for the subjects used for the substantially simultaneous bilateral stimulation at about 100% percent of the threshold intensity indicated as "1*Tmot" in FIGS. 15A and 15B) and with a pulse match was characterized by a current amplitude of about 0.15 mA (with a variation of about 0.03 mA), a frequency of about 10 Hz, and a pulse width of about 100 µs.

The triangular data points that include a single vertex at the top indicate the mean normalized bladder contraction frequencies of 8 subjects that received substantially simultaneous bilateral stimulation at about 100% of the threshold intensity level of the subject for approximately ten minutes, where the pulse trains were delivered to the two lateral sides of the subject such that the pulses of the pulse trains did not match in time. The mean threshold intensity level for the subjects used for the substantially simultaneous bilateral stimulation at about 100% of the threshold intensity and with a pulse mismatch was characterized by a current amplitude of about 0.21 mA (with a variation of about 0.03 mA), a frequency of about 10 Hz, and a pulse width of about 100 µs.

The experimental data shown in FIG. 15A is summarized in FIG. 15B, which is a bar graph that illustrates the mean response of the subjects during stimulation period 116 for each of the types of stimulation described with respect to FIG. 15A. The data shown in FIGS. 15A and 15B indicates that, for substantially simultaneous bilateral stimulation in which the pulse trains delivered to both lateral sides of the subjects overlapped, the pulse match and pulse mismatch of the pulses delivered to each of the lateral sides of the patient within the overlapping pulse trains did not appear to have a relatively significant impact on the reduction in bladder contraction frequency.

For example, in response to the substantially simultaneous bilateral stimulation delivered at about 80% of the threshold intensity level for the subjects with a pulse match, the mean response of the subjects during stimulation period 116 was a reduction in bladder contraction frequency of about 74.33%±14% ($p>0.05$) of the control and in response to the substantially simultaneous bilateral stimulation delivered at about 80% of the threshold intensity level for the subjects with a pulse mismatch, the response of the subjects during stimulation period 116 was a reduction in bladder contraction frequency of about 71.54%±11% ($p>0.05$) of the control. In addition, in response to the substantially simultaneous bilateral stimulation delivered at about 100% of the threshold intensity level for the subjects, the mean response of the subjects during stimulation period 116 was a bladder contraction frequency of about 28.24%±11% ($p<0.05$) of the control for the pulse match stimulation and about 15.62%±9% ($p<0.05$) of the control for the pulse mismatch stimulation. The experimental results shown in FIGS. 15A and 15B indicate that inhibition of bladder contractions may not require precise pulse locking on each lateral side of the patient.

Figure 16:
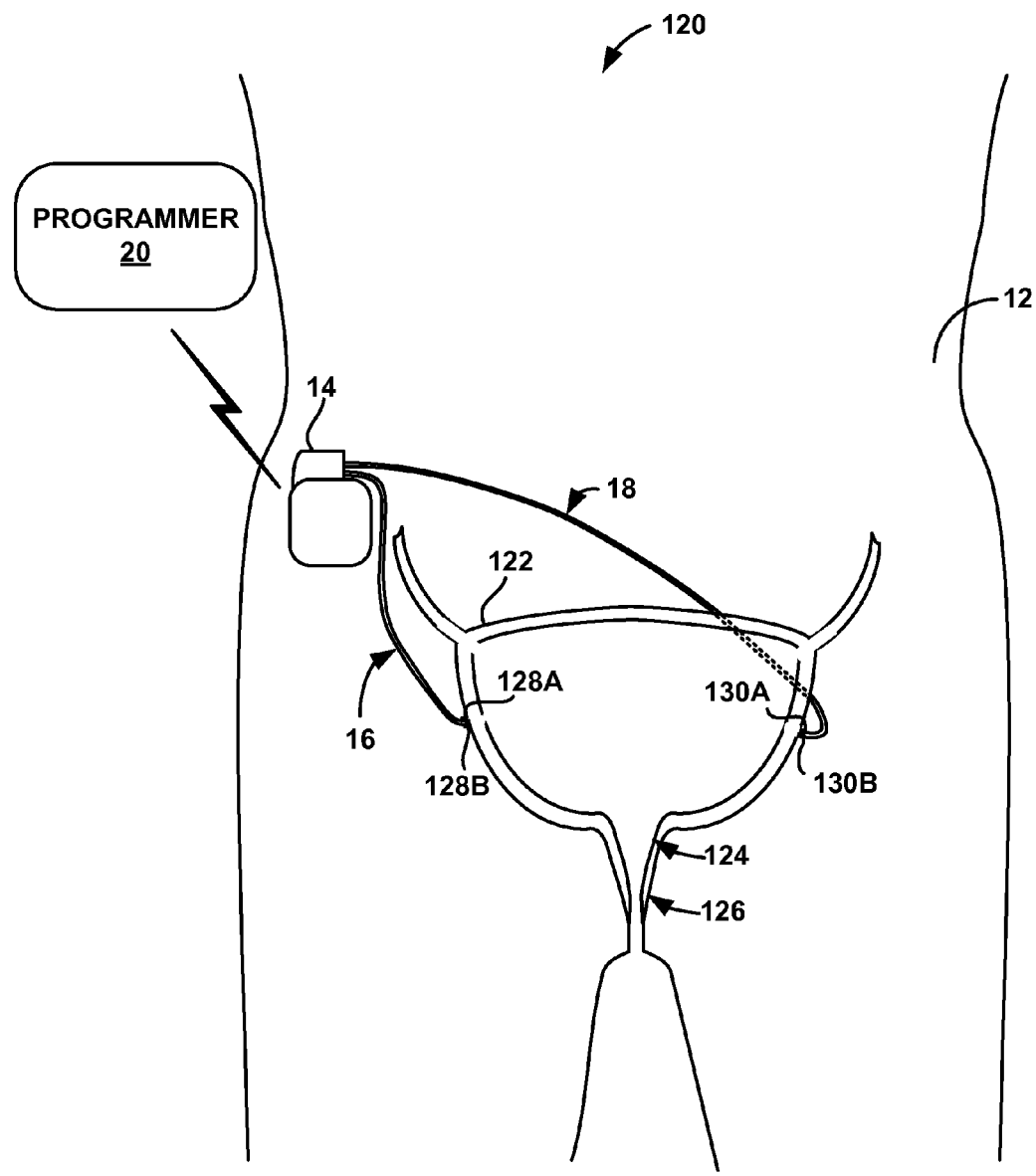
FIG. 16 is a conceptual diagram of a therapy system that is configured to determine an impedance of a bladder of a patient.

FIG. 16 is a conceptual diagram of therapy system 1, which is configured to determine an impedance of bladder 122 of patient 12. FIG. 16 also illustrates internal urinary sphincter 124 and external urinary sphincter 126. Therapy system 120 is similar to therapy system 10 of FIG. 1 and includes IMD 14, which is coupled to leads 16, 18, and programmer 20. In the example shown in FIG. 11, electrodes 128A, 128B of lead 16 and electrodes 130A, 130B of lead 18 are positioned proximate to an exterior surface of the wall of bladder 122. In some examples, electrodes 128A, 128B, 130A, and 130B may be sutured or otherwise affixed to the bladder wall. In other examples, electrodes 128A, 128B, 130A, and 130B may be implanted within the bladder wall. Electrodes 128A, 128B may be separate from electrodes 30 (FIG. 3) or may be a part of the electrodes 30. Similarly, electrodes 130A, 130B may be separate from electrodes 32 or may be a part of electrodes 32. In addition, in other examples, electrodes 128A, 128B, 130A, 130B are carried by other leads.

Processor 40 (FIG. 3) of IMD 14 may determine impedance of bladder 122 using a four-wire (or Kelvin) measurement technique. In other examples, IMD 14 may measure bladder impedance using a two-wire sensing arrangement. In either case, IMD 14 may transmit an electrical measurement signal, such as a current, through bladder 122 via leads 16, 18, and determine impedance of bladder 122 based on the transmitted electrical signal. Such an impedance measurement may be utilized to detect a bladder contraction, determine a fullness (i.e., a bladder fill level) of bladder 122, or the like.

In the example four-wire arrangement shown in FIG. 16, electrodes 128A and 130A and electrodes 12813 and 130B, may be located substantially opposite each other relative to the center of bladder 122. For example electrodes 128A and 130A may be placed on opposing sides of bladder, either anterior and posterior or left and right. To measure the impedance of bladder 122, stimulation generator 42 (FIG. 3) of IMD 14 or a separate impedance module of IMD 14 may source an electrical signal, such as current, to electrode 18A via lead 16, while electrode 130A via lead 18 sinks the electrical signal. In some examples, for collection of impedance measurements, IMD 14 may deliver electrical current signals that do not deliver stimulation therapy to bladder 122.

Voltage measurement circuitry of IMD 14 may measure the voltage between electrode 128B and electrode 12B via leads 16, 18, respectively. The voltage measurement circuitry 62 may include, for example, sample and hold circuitry or other suitable circuitry for measuring voltage amplitudes. Processor 40 determines the impedance of bladder 122 using a known value of the electrical signal sourced the determined voltage.

Although the techniques are primarily described in this disclosure for managing bladder dysfunction, the techniques may also be applied to manage fecal urgency, fecal incontinence, pain, and other conditions. In fecal incontinence examples, an IMD delivers the substantially simultaneous bilateral stimulation at a stimulation intensity greater than or equal to the threshold stimulation intensity when patient input is received, when a patient parameter indicative of an imminent fecal incontinence event is detected, when a patient parameter indicative of an increased probability of an occurrence of a fecal incontinence event is detected (e.g., an increased patient activity level), or when a predetermined period of time has passed. The patient parameter may include, for example, contraction of the anal sphincter, patient activity level or patient posture state. The IMD may use any suitable sensing mechanism to detect contraction of the anal sphincter, such as a pressure sensor or an EMG sensor.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by processor 40 of IMD 14 and/or processor 60 of programmer 14, any one or more parts of the techniques described herein may be implemented by a processor of one of IMD 14, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
   with a processor, controlling a stimulation generator to deliver a first electrical stimulation therapy to a patient, wherein the first electrical stimulation therapy comprises delivery of electrical stimulation to a first lateral side of the patient and a second lateral side of the patient at different times;
   after initiating delivery of the first electrical stimulation therapy, detecting a trigger event; and
   in response to detecting the trigger event, with the processor, controlling the stimulation generator to deliver a second electrical stimulation therapy to the patient, wherein the second electrical stimulation therapy comprises delivery of electrical stimulation substantially simultaneously to the first and second lateral sides of the patient.

2. The method of claim 1, wherein controlling the stimulation generator to deliver the first electrical stimulation therapy comprises controlling the stimulation generator to alternate delivery of electrical stimulation to the first and second lateral sides of the patient.

3. The method of claim 1, wherein controlling the stimulation generator to deliver at least one of the first or second electrical stimulation therapies comprises controlling the stimulation generator to deliver substantially balanced electrical stimulation to the first and second lateral sides of the patient.

4. The method of claim 3, wherein controlling the stimulation generator to deliver the substantially balanced electrical stimulation to the first and second lateral sides of the patient comprises controlling the stimulation generator to deliver electrical stimulation at substantially equal intensity levels to the first and second lateral sides of the patient.

5. The method of claim 3, wherein controlling the stimulation generator to deliver the substantially balanced electrical stimulation to the first and second lateral sides of the patient comprises controlling the stimulation generator to deliver electrical stimulation to the first and second lateral sides of the patient for substantially equal durations of time.

6. The method of claim 1, wherein controlling the stimulation generator to deliver at least one of the first or second electrical stimulation therapies comprises controlling the stimulation generator to deliver imbalanced electrical stimulation to the first and second lateral sides of the patient.

7. The method of claim 6, wherein controlling the stimulation generator to deliver the imbalanced electrical stimulation comprises controlling the stimulation generator to deliver electrical stimulation to the first lateral side of the patient at a first stimulation intensity level and controlling the stimulation generator to deliver electrical stimulation to the second lateral side of the patient at a second stimulation intensity level that is different than the first stimulation intensity level.

8. The method of claim 6, wherein controlling the stimulation generator to deliver the substantially imbalanced electrical stimulation to the first and second lateral sides of the patient comprises controlling the stimulation generator to deliver electrical stimulation to the first and second lateral sides of the patient for substantially different durations of time.

9. The method of claim 1, wherein controlling the stimulation generator to deliver at least one of the first or second electrical stimulation therapies comprises controlling the stimulation generator to deliver electrical stimulation to a first tissue site on the first lateral side of the patient via electrodes positioned on the first lateral side of the patient, and deliver electrical stimulation to a second tissue site on the second lateral side of the patient via electrodes positioned on the second lateral side of the patient, wherein the first and second tissue sites are proximate to branches of a same nerve.

10. The method of claim 1, wherein controlling the stimulation generator to deliver at least one of the first or second electrical stimulation therapies comprises controlling the stimulation generator to deliver electrical stimulation to a first tissue site on the first lateral side of the patient via electrodes positioned on the first lateral side of the patient, and deliver electrical stimulation to a second tissue site on the second lateral side of the patient via electrodes positioned on the second lateral side of the patient, wherein the first and second tissue sites are proximate to branches of different nerves.

11. The method of claim 1, wherein detecting the trigger event comprises detecting the trigger event while the first electrical stimulation therapy is being delivered to the patient.

12. The method of claim 1, wherein detecting the trigger event comprises, with the processor, detecting a bladder condition indicative of at least one of an increased possibility of an involuntary voiding event or an imminent involuntary voiding event.

13. The method of claim 1, wherein detecting the trigger event comprises receiving patient input via a user interface.

14. The method of claim 1, wherein detecting the trigger event comprises, with the processor, at least one of detecting a predetermined time of day or detecting expiration of a timer.

15. The method of claim 14, further comprising, with the processor, starting the timer when the first electrical stimulation therapy is delivered to the patient.

16. The method of claim 1, further comprising:
detecting a voiding event after initiating delivery of the second electrical stimulation therapy; and
after detecting the voiding event, controlling the stimulation generator to terminate delivery of the second electrical stimulation therapy and deliver the first electrical stimulation therapy to the patient.

17. The method of claim 1, wherein controlling the stimulation generator to deliver the second electrical stimulation therapy comprises controlling the stimulation generator to deliver the second electrical stimulation therapy for predetermined period of time.

18. The method of claim 17, further comprising:
after the stimulation generator delivers the second electrical stimulation therapy for the predetermined period of time, determining whether the trigger event is detected again;
controlling the stimulation generator to deliver the second electrical stimulation therapy for the predetermined of time in response to detecting the trigger event again; and
controlling the stimulation generator to deliver the first electrical stimulation therapy in response to not detecting the trigger event again.

19. A system comprising:
a stimulation generator configured to generate and deliver electrical stimulation to a patient; and
a processor configured to control the stimulation generator to deliver a first electrical stimulation therapy to the patient, wherein the first electrical stimulation therapy comprises delivery of electrical stimulation to a first lateral side of the patient and a second lateral side of the patient at different times, and wherein the processor is further configured to detect a trigger event after initiating delivery of the first electrical stimulation therapy and, in response to detecting the trigger event, control the stimulation generator to deliver a second electrical stimulation therapy to the patient, wherein the second electrical stimulation therapy comprises delivery of electrical stimulation substantially simultaneously to the first and second lateral sides of the patient.

20. The system of claim 19, wherein the processor is configured to control the stimulation generator to deliver the first electrical stimulation therapy by at least alternating delivery of electrical stimulation to the first and second lateral sides of the patient.

21. The system of claim 19, wherein at least one of the first or second electrical stimulation therapies comprises delivery of substantially balanced electrical stimulation therapy to the first and second lateral sides of the patient.

22. The system of claim 21, wherein the substantially balanced electrical stimulation therapy comprises delivery of electrical stimulation at substantially equal intensity levels to the first and second lateral sides of the patient.

23. The system of claim 21, wherein the substantially balanced electrical stimulation therapy comprises delivery of electrical stimulation to the first and second lateral sides of the patient for substantially equal durations of time.

24. The system of claim 19, wherein at least one of the first or second stimulation therapies comprises delivery of imbalanced electrical stimulation therapy to the first and second lateral sides of the patient.

25. The system of claim 24, wherein the processor controls the stimulation generator to deliver the imbalanced electrical stimulation therapy by at least delivering electrical stimulation to the first lateral side of the patient at a first stimulation intensity level and delivering electrical stimulation to the second lateral side of the patient at a second stimulation intensity level that is different than the first stimulation intensity level.

26. The system of claim 24, wherein the substantially balanced electrical stimulation therapy to the first and second lateral sides of the patient comprises delivery of electrical stimulation to the first and second lateral sides of the patient for substantially different durations of time.

27. The system of claim 19, further comprising a first set of electrodes configured to be positioned on the first lateral side of the patient and a second set of electrodes configured to be positioned on the second lateral side of the patient, wherein the stimulation generator is configured to deliver at least one of the first or second electrical stimulation therapies by at least delivering electrical stimulation to a first tissue site on the first lateral side of the patient via the first set of electrodes and delivering electrical stimulation to a second tissue site on the second lateral side of the patient via the second set of electrodes.

28. The system of claim 19, further comprising a sensor configured to generate a signal indicative of a physiological parameter of the patient, wherein the processor is configured to detect the trigger event by at least detecting, based on the signal, a bladder condition indicative of at least one of an increased possibility of an involuntary voiding event or an imminent involuntary voiding event.

29. The system of claim 19, further comprising a user interface, wherein the processor is configured to detect the trigger event by at least receiving input via the user interface.

30. The system of claim 19, wherein the processor is configured to detect the trigger event by at least one of detecting a predetermined time of day or detecting expiration of a timer.

31. The system of claim 30, wherein the processor is configured to start the timer when the first stimulation therapy is delivered to the patient.

32. The system of claim 19, wherein the processor is configured to detect a voiding event after initiating delivery of the second stimulation therapy, control the stimulation generator to deliver the second stimulation therapy until the voluntary voiding event is detected, and, after detecting the voiding event, control the stimulation generator to terminate delivery of the second stimulation therapy and deliver the first stimulation therapy to the patient.

33. The system of claim 19, wherein the processor is configured to control the stimulation generator to deliver the second stimulation therapy for predetermined period of time.

34. The system of claim 33, wherein the processor is configured to determine, after the stimulation generator delivers the second stimulation therapy to the patient for the predetermined period of time, whether the trigger event is detected again, and control the stimulation generator to deliver the second stimulation therapy for the predetermined of time in response to determining the trigger event is detected again and control the stimulation generator to deliver the first stimulation therapy in response to determining the trigger event is not detected again.

35. A system comprising:
means for delivering electrical stimulation therapy to a patient;
means for detecting a trigger event after initiating delivery of the first electrical stimulation therapy; and
means for controlling the means for delivering electrical stimulation therapy, wherein the means for controlling is configured to control the means for delivering electrical stimulation therapy to deliver a first electrical stimulation therapy to a patient, wherein the first electrical stimulation therapy comprises delivery of electrical stimulation to a first lateral side of the patient and a second lateral side of the patient at different times, the means for controlling being further configured to, in response to detection of the trigger event, control the means for delivering electrical stimulation therapy to deliver a second electrical stimulation therapy to the patient, wherein the second electrical stimulation therapy comprises delivery of electrical stimulation substantially simultaneously to the first and second lateral sides of the patient.

36. The system of claim 35, wherein at least one of the first or second electrical stimulation therapies comprises delivery of substantially balanced electrical stimulation to the first and second lateral sides of the patient.

37. The system of claim 35, wherein at least one of the first or second electrical stimulation therapies comprises delivery of imbalanced electrical stimulation to the first and second lateral sides of the patient.

38. The system of claim 35, wherein the trigger event comprises at least one of a bladder condition indicative of at least one of an increased possibility of an involuntary voiding event or an imminent involuntary voiding event, patient input, detection of a predetermined time of day, or expiration of a timer.

39. A computer-readable medium comprising instructions that, when executed by a processor, cause the processor to:
control a stimulation generator to deliver a first electrical stimulation therapy to a patient, wherein the first electrical stimulation therapy comprises delivery of electrical stimulation to a first lateral side of the patient and a second lateral side of the patient at different times;
detect a trigger event after the first stimulation therapy is initiated; and
in response to detecting the trigger event, control the stimulation generator to deliver a second electrical stimulation therapy to the patient, wherein the second electrical stimulation therapy comprises delivery of electrical stimulation substantially simultaneously to the first and second lateral sides of the patient.

40. The computer-readable medium of claim 39, wherein at least one of the first or second electrical stimulation therapies comprises delivery of substantially balanced electrical stimulation to the first and second lateral sides of the patient.

41. The computer-readable medium of claim 39, wherein at least one of the first or second electrical stimulation therapies comprises delivery of imbalanced electrical stimulation to the first and second lateral sides of the patient.

42. The computer-readable medium of claim 39, wherein the trigger event comprises at least one of a bladder condition indicative of at least one of an increased possibility of an involuntary voiding event or an imminent involuntary voiding event, patient input, a predetermined time of day, or expiration of a timer.

* * * * *